United States Patent
Barrow et al.

(10) Patent No.: US 7,550,481 B2
(45) Date of Patent: Jun. 23, 2009

(54) PHENYLAMIDE AND PYRIDYLAMIDE BETA-SECRETASE INHIBITORS FOR THE TREATMENT OF ALZHEIMER'S DISEASE

(75) Inventors: James C. Barrow, Harleysville, PA (US); Craig A. Coburn, Royersford, PA (US); Philippe G. Nantermet, Lansdale, PA (US); Harold G. Selnick, Ambler, PA (US); Shawn J. Stachel, Perkasie, PA (US); Matthew G. Stanton, Lansdale, PA (US); Shaun R. Stauffer, Schwenksville, PA (US); Linghang Zhuang, Chalfont, PA (US); Jennifer R. Davis, Richboro, PA (US)

(73) Assignee: Merck & Co., Inc., Rahway, NJ (US)

( * ) Notice: Subject to any disclaimer, the term of this patent is extended or adjusted under 35 U.S.C. 154(b) by 141 days.

(21) Appl. No.: 10/582,856

(22) PCT Filed: Dec. 15, 2004

(86) PCT No.: PCT/US2004/042173

§ 371 (c)(1),
(2), (4) Date: Jun. 14, 2006

(87) PCT Pub. No.: WO2005/065195

PCT Pub. Date: Jul. 21, 2005

(65) Prior Publication Data

US 2007/0142634 A1    Jun. 21, 2007

Related U.S. Application Data

(60) Provisional application No. 60/531,423, filed on Dec. 19, 2003.

(51) Int. Cl.
C07D 401/02 (2006.01)
A61K 31/44 (2006.01)

(52) U.S. Cl. ........................ 514/307; 514/310; 514/313; 514/314; 514/342; 514/343; 514/352; 514/619; 546/143; 546/144; 546/159; 546/276.4; 546/280.4; 546/304; 546/307; 546/312; 564/161

(58) Field of Classification Search ........................ None
See application file for complete search history.

(56) References Cited

U.S. PATENT DOCUMENTS 5,693,815 A    12/1997    Bennett et al.

| | | |
|---|---|---|
| 2005/0038028 A1 | 2/2005 | Faller et al. |
| 2006/0025459 A1* | 2/2006 | Demont et al. ............... 514/372 |
| 2006/0211740 A1* | 9/2006 | Demont et al. ............... 514/352 |

FOREIGN PATENT DOCUMENTS

| | | |
|---|---|---|
| EP | 1 186 305 | 3/2002 |
| WO | WO 02/02512 | 1/2002 |
| WO | WO 03/027068 | 4/2003 |
| WO | WO 03/045903 | 6/2003 |
| WO | WO 03/057721 | 7/2003 |
| WO | WO 03/072535 | 9/2003 |
| WO | WO 03/106405 | 12/2003 |
| WO | WO 2004/024675 | 3/2004 |
| WO | WO 2004/043916 | 5/2004 |
| WO | WO 2004/050619 | 6/2004 |
| WO | WO 2004/062625 | 7/2004 |
| WO | WO 2004/080376 | 9/2004 |
| WO | WO 2005/004802 | 1/2005 |
| WO | WO 2005/004803 | 1/2005 |
| WO | WO 2005/005374 | 1/2005 |
| WO | WO 2005/018545 | 3/2005 |
| WO | WO 2005/032471 | 4/2005 |
| WO | WO 2005/051914 | 6/2005 |

OTHER PUBLICATIONS

C. A. Coburn et al., "Identification of a Small Molecule . . . ," J. Med. Chem., vol. 47, pp. 6117-6119 (2004).
S. J. Stachel et al., "Structure-Based Design of Potent . . . ," J. Med. Chem., vol. 47, pp. 6447-6450 (2004).
S. J. Stachel et al., "Conformationally biased P3 amide replacements of beta-secretase inhibitors," Bioorganic & Medicinal Chemistry Letters, vol. 16, pp. 641-644 (2006).
EP Communication in EPO Appln No. 04 814 367.1, Dec. 21, 2007.

* cited by examiner

Primary Examiner—Zinna N Davis
(74) Attorney, Agent, or Firm—William Krovatin; John C. Todaro

(57) ABSTRACT

The present invention is directed to phenylamide and pyridylamide derivative compounds of which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

21 Claims, No Drawings

PHENYLAMIDE AND PYRIDYLAMIDE BETA-SECRETASE INHIBITORS FOR THE TREATMENT OF ALZHEIMER'S DISEASE

CROSS-REFERENCE TO RELATED APPLICATIONS

This application claims priority under 35 U.S.C. § 119 of U.S. provisional application Ser. No. 60/531,423, filed Dec. 19, 2003.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to compounds useful as inhibitors of the beta secretase enzyme, and useful in the treatment of diseases in which the beta secretase enzyme is involved, such as Alzheimer's Disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to phenylamide and pyridylamide derivative compounds having a terminal or branched amino or hydroxyl group. The compounds are inhibitors of the β-secretase enzyme, and are useful in the treatment of diseases in which the β-secretase enzyme is involved, such as Alzheimer's disease. The invention is also directed to pharmaceutical compositions comprising these compounds, and the use of these compounds and compositions in the treatment of such diseases in which the β-secretase enzyme is involved.

DETAILED DESCRIPTION OF THE INVENTION

The present invention is directed to compounds of formula (I):

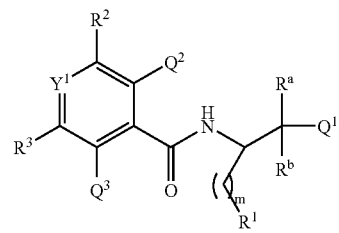

wherein:
$Y^1$ is CH or N;
$Q^1$ is selected from the group consisting of
  (1) —OH, and
  (2) —$NH_2$;
$Q^2$ and $Q^3$ are independently selected from the group consisting of
  (1) hydrogen, and
  (2) halogen;
$R^a$ is selected from the group consisting of
  (1) hydrogen,
  (2) —$C_{1-10}$ alkyl, wherein said alkyl is unsubstituted or substituted with one or more fluoro, and
  (3) —$C_{3-8}$ cycloalkyl;
$R^b$ is selected from the group consisting of
  (1) hydrogen,
  (2) —$C_{1-10}$ alkyl,
  (3) —$C_{1-3}$ alkyl-aryl, wherein said aryl is selected from the group consisting of phenyl and naphthyl,
  (4) —$C_{3-8}$ cycloalkyl,
  wherein said cycloalkykl, alkyl and aryl are unsubstituted or substituted with one or more
    (a) halo,
    (b) —OH,
    (c) —CN,
    (d) —O—$C_{1-10}$ alkyl,
  (5) —$(CH_2)_n$—$NR^cR^d$ wherein $R^c$ and $R^d$ are selected from the group consisting of hydrogen and $C_{1-10}$ alkyl, and n is 2, 3 or 4, and
  (6) —$(CH_2)_{n'}$—O—$R^e$ wherein $R^e$ is selected from the group consisting of
    (a) —$C_{1-10}$ alkyl,
    (b) —$C_{0-3}$ alkyl-aryl, wherein said aryl is selected from the group consisting of phenyl and naphthyl, wherein said alkyl and aryl are unsubstituted or substituted with one or more
- (i) halo,
- (ii) —OH,
- (iii) —CN,
- (iv) —O—$C_{1-10}$ alkyl, and n' is 1, 2, 3 or 4;

m is 1 or 2;

$R^1$ is (1) aryl selected from the group consisting of phenyl and napthyl, or
- (2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
- (3) —$C_{1-10}$ alkyl, and
- (4) —$C_{3-8}$ cycloalkyl, wherein said aryl, heteroaryl, alkyl and cycloalkyl is unsubstituted or substituted with one or more
- (a) halo,
- (b) —OH,
- (c) —CN,
- (d) —O—$C_{1-10}$ alkyl,
- (e) —$C_{1-10}$ alkyl,
- (f) —$C_{3-8}$ cycloalkyl,
- (g) aryl selected from the group consisting of phenyl and napthyl, or
- (h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;

$R^2$ is selected from the group consisting of:
- (1) ($R^4$—$SO_2$)N($R^7$)—, wherein $R^4$ is
  - (a) —$C_{1-10}$ alkyl,
  - (b) —$C_{3-8}$ cycloalkyl, wherein said alkyl and cycloalkyl is unsubstituted or substituted with one or more
  - (i) halo,
  - (ii) —OH,
  - (iii) —CN,
  - (iv) —O—$C_{1-10}$ alkyl,
  - (v) —$C_{1-10}$ alkyl,
  - (vi) —$C_{3-8}$ cycloalkyl,
  - (vii) aryl selected from the group consisting of phenyl and napthyl, or
  - (viii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, and said aryl and heteroaryl is unsubstituted or substituted with one or more
  - (A) halo,
  - (B) —OH,
  - (C) —CN,
  - (D) —O—$C_{1-10}$ alkyl,
  - (E) —$C_{3-8}$ cycloalkyl, or
  - (F) —$C_{1-10}$ alkyl,
- (c) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, wherein said heteroaryl is unsubstituted or substituted with one or more
  - (i) halo,
  - (ii) —OH,
  - (iii) —CN,
  - (iv) —O—$C_{1-10}$ alkyl,
  - (v) —$C_{3-8}$ cycloalkyl, or
  - (vi) —$C_{1-10}$ alkyl,
- (d) —$(CH_2)_x$—$NR^fR^g$ wherein $R^f$ and $R^g$ are selected from the group consisting of hydrogen and $C_{1-10}$ alkyl, and x is 0, 1, 2, 3 or 4 or $R^f$ and $R^g$, together with the nitrogen atom to which they are attached, form the group

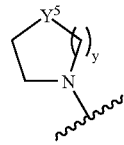

wherein y is 1 or 2, $Y^5$ is —$CHR^{21}$, —O— or $NR^{21}$, wherein $R^{21}$ is selected from the group consisting of;
- (i) hydrogen, and
- (ii) $C_{1-10}$ alkyl, wherein said alkyl is unsubstituted or substituted with one or more
- (A) halo,
- (B) —OH,
- (C) —CN,
- (D) —O—$C_{1-10}$ alkyl, or
- (E) —$C_{3-8}$ cycloalkyl;

$R^7$ is selected from the group consisting of
- (a) hydrogen, and
- (b) —$C_{1-10}$ alkyl,
- (c) aryl selected from the group consisting of phenyl and napthyl, or
- (d) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl wherein said alkyl, aryl or heteroaryl is unsubstituted or substituted with one or more
- (i) halo,
- (ii) —OH,
- (iii) —CN,
- (iv) —O—$C_{1-10}$ alkyl,
- (v) —$C_{3-8}$ cycloalkyl,
- (vi) aryl selected from the group consisting of phenyl and napthyl, or
- (vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, wherein said cycloalkyl, aryl or heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) aryl selected from the group consisting of phenyl and napthyl;
(e) —$(CH_2)_{y'}$—$NR^hR^i$ wherein $R^h$ and $R^i$ are selected from the group consisting of hydrogen and $C_{1-10}$ alkyl, and y' is 1, 2, 3 or 4, or $R^h$ and $R^i$, together with the nitrogen atom to which they are attached, form the group

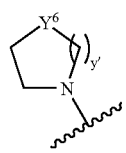

wherein y' is 1 or 2, $Y^6$ is —$CHR^{22}$, —O— or $NR^{22}$, wherein $R^{22}$ is selected from the group consisting of;
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl,
or $R^4$ and $R^7$ are linked together to form the group (a)

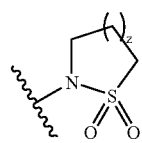

wherein z is 1, 2 or 3; or (b)

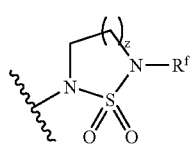

wherein z is 1, 2 or 3

(2)

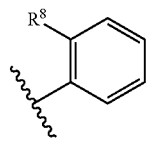

wherein $R^8$ is selected from the group consisting of
(a) —CN,
(b) hydrogen, and
(c) tetrazolyl;

(3)

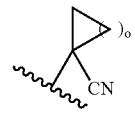

wherein o is 1, 2, 3 or 4; and (4)

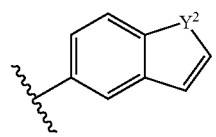

wherein $Y^2$ is —NH═CH— or —CH═NH—;
$R^3$ is selected from the group consisting of (1)

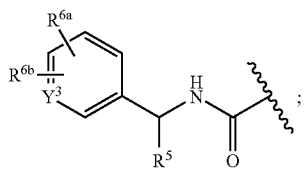

(2)

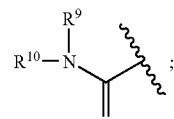

(3)

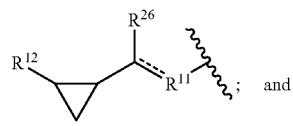; and (4)

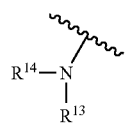

wherein $Y^3$ is $CR^{6c}$ or N;
$R^5$ is $C_{1-10}$ alkyl or $C_{1-2}$ perfluoroalkyl;
$R^{6a}$, $R^{6b}$, and $R^{6c}$ are independently selected from the group consisting of:
(1) hydrogen,
(2) halo,
(3) —$C_{1-10}$ alkyl,
(4) —OH,
(5) —CN,
(6) —$C_{3-8}$ cycloalkyl, and
(7) —O—$C_{1-10}$ alkyl;
$R^9$ and $R^{10}$ are independently selected from the group consisting of
(1) hydrogen, (2) —$C_{1-10}$ alkyl, and
(3) —$C_{3-8}$ cycloalkyl,
wherein said alkyl and cycloalkyl are unsubstituted or substituted with one or more
   (a) halo,
   (b) —OH,
   (c) —CN,
   (d) —O—$C_{1-10}$ alkyl,
   (e) —$C_{3-8}$ cycloalkyl, and
   (f) —NR$^j$R$^k$ wherein R$^j$ and R$^k$ are $C_{1-10}$ alkyl;
or R$^9$ and R$^{10}$ are joined together with the nitrogen atom to which they are attached to form

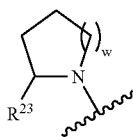

wherein w is 1, 2 or 3, and
R$^{23}$ is selected from the group consisting of
   (a) hydrogen,
   (b) —$C_{1-10}$ alkyl,
   (c) —$C_{3-8}$ cycloalkyl,
   (d) —$C_{2-10}$ alkenyl,
   (e) —$C_{2-10}$ alkynyl,
   (f) —(CH$_2$)$_p$-phenyl,
   (g) —(CH$_2$)$_p$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein p is 0 or 1, and
wherein said alkyl, alkenyl, alkynyl, cycloalkyl, phenyl and heteroaryl is unsubstituted or substituted with one or more
   (i) halo,
   (ii) —$C_{1-10}$ alkyl,
   (iii) —OH,
   (iv) —CN,
   (v) —$C_{3-8}$ cycloalkyl, or
   (vi) —O—$C_{1-10}$ alkyl;
R$^{11}$ is selected from the group consisting of
   (1) —CH—,
   (2) —CH$_2$—,
   (3) —O—, and
   (4) —NR$^{17}$—,
provided that when R$^{11}$ is —CH— the dotted line forms a bond and when R$^{11}$ is —CH$_2$—, —O— or —NR$^{17}$— the dotted line is absent;
R$^{17}$ is hydrogen or $C_{1-10}$ alkyl, wherein said $C_{1-10}$ alkyl is unsubstituted or substituted with one or more
   (a) halo,
   (b) —OH,
   (c) —CN,
   (d) —$C_{3-8}$ cycloalkyl,
   (e) —O—$C_{1-10}$ alkyl,
   (f) —(CH$_2$)$_q$-phenyl, wherein q is 1 or 2, and
   (g) —NR$^{18}$R$^{19}$, and
   wherein R$^{18}$ and R$^{19}$ are independently selected from the group consisting of
      i) hydrogen, or
      ii) $C_{1-10}$ alkyl;

or R$^{18}$ and R$^{19}$, together with the nitrogen atom to which they are attached, form the group

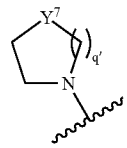

wherein q' is 1 or 2, Y$^7$ is —CHR$^{24}$, —O— or NR$^{24}$, wherein R$^{24}$ is selected from the group consisting of;
   (a) hydrogen, and
   (b) $C_{1-10}$ alkyl,
   wherein said alkyl is unsubstituted or substituted with one or more
      i) halo,
      ii) —OH,
      iii) —CN,
      iv) —O—$C_{1-10}$ alkyl, or
      v) —$C_{3-8}$ cycloalkyl;
R$^{26}$ is selected from the group consisting of
   (1) hydrogen, and
   (2) —$C_{1-3}$ alkyl;
R$^{12}$ is selected from the group consisting of
   (1) hydrogen,
   (2) —$C_{1-10}$ alkyl, wherein said alkyl is unsubstituted or substituted with one or more
      (a) halo,
      (b) —OH,
      (c) —CN,
      (d) —$C_{3-8}$ cycloalkyl,
      (e) —O—$C_{1-10}$ alkyl, or
      (f) —NH$_2$,
   (3) halo,
   (4) —$C_{3-8}$ cycloalkyl,
   (5) aryl selected from the group consisting of phenyl and napthyl, and
   (6) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
   wherein said aryl and heteroaryl is unsubstituted or substituted with one or more
      (a) halo,
      (b) —OH,
      (c) —CN,
      (d) —O—$C_{1-10}$ alkyl,
      (e) —$C_{3-8}$ cycloalkyl, or
      (f) —$C_{1-10}$ alkyl;
R$^{13}$ is selected from the group consisting of
   (1) hydrogen,
   (2) $C_{1-10}$ alkyl, and
   (3) —$C_{3-8}$ cycloalkyl;
   wherein said alkyl and cycloalkyl is unsubstituted or substituted with one or more
      (a) halo,
      (b) —OH,
      (c) —CN,
      (d) —$C_{3-8}$ cycloalkyl,
      (e) —O—$C_{1-10}$ alkyl, and
      (f) —$C_{1-10}$ alkyl;

$R^{14}$ is selected from the group consisting of
(1) —$C_{1-10}$ alkyl, and
(2) —$C_{3-8}$ cycloalkyl;
wherein said alkyl and cycloalkyl is unsubstituted or substituted with one or more
(a) halo,
(b) —OH,
(c) —CN,
(d) —$C_{3-8}$ cycloalkyl,
(e) —O—$C_{1-10}$ alkyl, or
(f) —$C_{1-10}$ alkyl;
(3) —$(CH_2)_v$—$NR^{15}R^{16}$, wherein v is 2, 3 or 4, and
wherein $R^{15}$ and $R^{16}$ are independently selected from the group consisting of
(a) hydrogen, or
(b) $C_{1-10}$ alkyl, wherein said $C_{1-10}$ alkyl is unsubstituted or substituted with one or more
(i) halo,
(ii) —OH,
(iii) —CN,
(iv) —$C_{3-8}$ cycloalkyl, or
(v) —O—$C_{1-10}$ alkyl;
or $R^{15}$ and $R^{16}$, together with the nitrogen atom to which they are attached, form the group

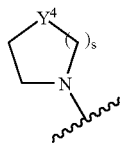

wherein s is 1 or 2, $Y^4$ is —$CHR^{24}$—, —O— or —$NR^{24}$—, wherein $R^{24}$ is selected from the group consisting of
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl,
(4) —$(CH_2)_r$-phenyl, wherein r is 1, 2, 3, or 4, and
wherein said phenyl is unsubstituted or substituted with one or more
(a) halo,
(b) —OH,
(c) —CN,
(d) —O—$C_{1-10}$ alkyl,
(e) —$C_{3-8}$ cycloalkyl, or
(f) —$C_{1-10}$ alkyl;
or $R^{13}$ and $R^{14}$, together with the nitrogen atom to which they are attached, form the group

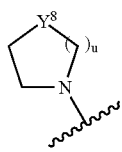

wherein u is 1 or 2, $Y^8$ is —$CHR^{25}$—, —O— or —$NR^{25}$—, wherein $R^{25}$ is selected from the group consisting of
(a) hydrogen,
(b) $C_{1-10}$ alkyl,
(c) —$(CH_2)_t$-phenyl,
(d) —$(CH_2)_t$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein t is 0 or 1, and
wherein said alkyl, phenyl and heteroaryl is unsubstituted or substituted with one or more
(i) halo,
(ii) —$C_{1-10}$ alkyl,
(iii) —OH,
(iv) —CN,
(v) —$C_{3-8}$ cycloalkyl, or
(vi) —O—$C_{1-10}$ alkyl;
and pharmaceutically acceptable salts thereof.

In one embodiment of the compounds of formula (I), $Q^2$ and $Q^3$ are hydrogen. In an alternative embodiment, $Q^3$ is hydrogen and $Q^2$ is halogen, preferably chloro. In another embodiment, $Q^2$ is hydrogen and $Q^3$ is halogen, preferably chloro.

In a preferred embodiment of the compounds of the invention, $R^a$ and $R^b$ are both hydrogen. In another preferred embodiment, $R^a$ is hydrogen and $R^b$ is as defined above. In another preferred embodiment, $R^a$ is hydrogen and $R^b$ is $C_{1-10}$ alkyl, preferably $C_{1-5}$ linear alkyl. In another preferred embodiment, $Q^1$ is OH, $R^a$ is hydrogen and $R^b$ is —$(CH_2)_2$—$NR^cR^d$.

In a preferred embodiment of the compounds of the invention, $R^1$ is selected from the group consisting of
(1) aryl selected from the group consisting of phenyl and napthyl, or
(2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl or heteroaryl is unsubstituted or substituted with one or more
(a) halo,
(b) —$C_{1-6}$ alkyl,
(c) —OH,
(d) —CN, or
(e) —O—$C_{1-6}$ alkyl,
wherein m is 1 or 2.

In a more preferred embodiment, $R^1$ is phenyl, unsubstituted or substituted in one or two positions with halo, preferably with fluoro or chloro, and m is 1.

In another preferred embodiment, $R^1$ is thienyl, unsubstituted or substituted, and m is 1. In a more preferred embodiment, $R^1$ is unsubstituted 3-thienyl, and m is 1.

In a preferred embodiment of the compounds of the invention, $R^2$ is selected from the group consisting of
(1) $(R^4$—$SO_2)N(R^7)$—, wherein $R^4$ is —$C_{1-6}$ alkyl, wherein said alkyl is unsubstituted or substituted with one or more
(i) halo,
(ii) —OH,
(iii) —CN,
(iv) —O—$C_{1-6}$ alkyl, or
(v) —$C_{1-6}$ alkyl, $R^7$ is selected from the group consisting of
(a) hydrogen,
(b) —$C_{1-6}$ alkyl,
wherein said alkyl is unsubstituted or substituted with one or more
(i) halo,
(ii) —OH,
(iii) —CN,
(iv) —O—$C_{1-6}$ alkyl,
(v) —$C_{1-6}$ alkyl; and (2)

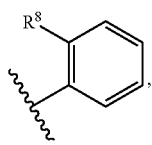

wherein $R^8$ is phenyl or tetrazolyl, preferably 5-tetrazolyl.

In a more preferred embodiment of the compounds of the invention, $R^2$ is $(R^4SO_2)N(R^7)$—, wherein $R^4$ and $R^7$ are each $C_{1-6}$alkyl. Exemplary preferred $R^2$ groups include $(R^4SO_2)N(R^7)$— wherein $R^4$ and $R^7$ are each methyl, or $(R^4SO_2)N(R^7)$—, wherein $R^4$ is methyl and $R^7$ is propyl.

In one embodiment of the compounds of the invention, $R^3$ is (1) as described above, $Y^3$ is $CHR^{6c}$, $R^5$ is methyl, $R^{6a}$ and $R^{6c}$ are hydrogen and $R^{6b}$ is fluoro. In another preferred embodiment, $R^3$ is (1) as described above, $Y^3$ is N, $R^5$ is $C_{1-2}$ perfluoroalkyl, and $R^{6a}$ and $R^{6b}$ are each hydrogen.

In another embodiment of the compounds of the invention, $R^3$ is (2) as described above, and $R^9$ and $R^{10}$ are each unsubstituted $C_{1-10}$ alkyl, preferably unsubstituted $C_{1-5}$ linear alkyl. In another embodiment, $R^3$ is (2) as described above, and $R^9$ and $R^{10}$ are joined together with the nitrogen atom to which they are attached to form a pyrrolidine ring (wherein w is 1) and $R^{23}$ is —$(CH_2)_p$-phenyl or —$(CH_2)_p$-heteroaryl, wherein the phenyl and heteroaryl are unsubstituted or substituted with chloro, and wherein p is preferably 0.

In another embodiment, $R^3$ is (3) as described above, and $R^{11}$ is $NR^{17}$ wherein $R^{17}$ is preferably hydrogen or $C_{1-3}$ alkyl, and $R^{12}$ is preferably hydrogen or methyl.

In another embodiment of the compounds of the invention, $R^3$ is (4) as described above, and $R^{13}$ is hydrogen, $R^{14}$ is —$(CH_2)_v$—$NR^{15}R^{16}$ wherein v is 2 and $R^{15}$ and $R^{16}$ are $C_{1-10}$ alkyl, preferably $C_{1-5}$ alkyl, which is unsubstituted or substituted with —OH, —CN or —$OCH_3$.

In another embodiment, $R^3$ is (4) as described above, $R^{13}$ and $R^{14}$ are joined together with the nitrogen atom to which they are attached to form a pyrrolidine ring (when $Y^8$ is CH and s is 1), which is substituted with —$(CH_2)_t$-phenyl or —$(CH_2)_t$-heteroaryl, wherein the phenyl and heteroaryl are unsubstituted or substituted with chloro, and wherein t is preferably 0.

In another embodiment of the compounds of the invention, $Y^1$ is CH.

In another embodiment of the compounds of the invention, $Y^1$ is N.

One embodiment of the present invention is directed to compounds of formula (II):

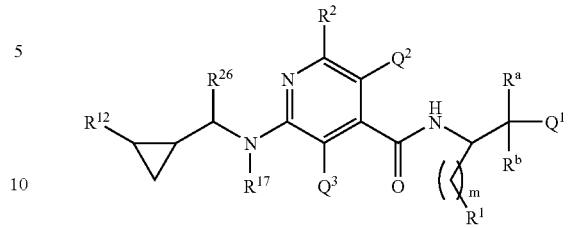

II wherein $Q^1$, $Q^2$, $Q^3$, $R^a$, $R^b$, $R^1$, $R^2$, $R^{12}$, $R^{17}$, $R^{26}$ and m are as defined above, and pharmaceutically acceptable salts thereof.

In one embodiment of the compounds of formula (II), $Q^2$ and $Q^3$ are hydrogen. In an alternative embodiment, $Q^3$ is hydrogen and $Q^2$ is halogen, preferably chloro.

In a preferred embodiment of the compounds of formula (II), $Q^1$ is $NH_2$, and $R^a$ and $R^b$ are each hydrogen.

In another preferred embodiment of the compounds of formula (II), $Q^1$ is $NH_2$, $R^a$ is hydrogen and $R^b$ is $C_{1-5}$ linear alkyl.

In a preferred embodiment of the compounds of formula (II), $Q^1$ is OH, and $R^a$ and $R^b$ are each hydrogen.

In a preferred embodiment of the compounds of formula (II), $Q^1$ is OH, and $R^a$ is hydrogen and $R^b$ is $C_{1-5}$ linear alkyl.

Another embodiment of the present invention is directed to compounds of the formula (III):

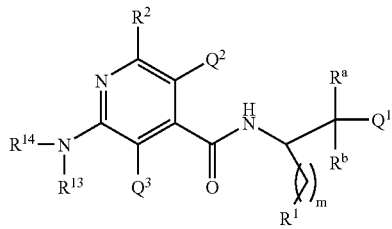

III wherein $Q^1$, $Q^2$, $Q^3$, $R^a$, $R^b$, $R^1$, $R^2$, $R^{13}$, $R^{14}$ and m are as defined above, and pharmaceutically acceptable salts thereof.

In one embodiment of the compounds of formula (III), $Q^2$ and $Q^3$ are hydrogen. In an alternative embodiment, $Q^3$ is hydrogen and $Q^2$ is halogen, preferably chloro.

In another embodiment of the compounds of formula (III), $Q^1$ is OH and $R^a$ and $R^b$ are each hydrogen.

In another embodiment of the compounds of formula (III), $Q^1$ is $NH_2$ and $R^a$ and $R^b$ are each hydrogen.

Another embodiment of the invention is directed to compounds of the formula (IV):

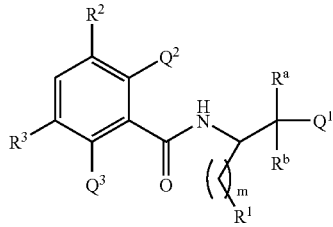

IV wherein $Q^1$, $Q^2$, $Q^3$, $R^a$, $R^b$, $R^1$, $R^2$ and m are as defined above, and $R^3$ is (1) or (2) as defined above, and pharmaceutically acceptable salts thereof. In preferred embodiments, $R^a$ is hydrogen and $R^b$ is $C_{1-5}$ linear alkyl.

In one embodiment of the compounds of formula (IV), $Q^2$ and $Q^3$ are hydrogen. In an alternative embodiment, $Q^3$ is hydrogen and $Q^2$ is halogen, preferably chloro.

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-8}$ cycloalkyl means a cycloalkyl group having from three to eight carbon atoms). Exemplary cycloalkyl groups include cyclopropyl, cyclobutyl, cyclopentyl, cyclohexyl and the like.

The term "halo" or "halogen" includes fluoro, chloro, bromo and iodo.

When a heteroaryl group as defined herein is substituted, the substituent may be bonded to a ring carbon atom of the heteroaryl group, or on a heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

The compounds claimed in this invention can be prepared according to the following general procedures.

Scheme 1 outlines the synthesis of amino alcohols 5 and 40 and amino azides 6. Treatment of commercially available ketone 43 with excess methyl magnesium bromide, followed by Boc deprotection gives amino alcohol 40. Starting from commercially available enantiopure amino esters 1, the amine is Boc protected and the ester hydrolyzed to give acid 2. Alternatively, commercially available enantiopure amino acids may be Boc protected using Schotten-Baumann conditions. EDC coupling of 2 with Weinreb's amine generates the Weinreb amide 3. Treatment of the Weinreb amide with organometallic reagents gives ketones 4. The ketones are then reduced to give a diastereomeric mixture of alcohols 5a. The individual diastereomers of 5a are either treated directly with HCl to give amino alcohol 5b or treated with hydrazoic acid under Mitsunobu conditions to generate the desired azide. Alternatively, the alcohol can be mesylated and displaced with sodium azide. Removal of the Boc group with HCl gives the amino azide 6. Alternatively, the Weinreb amide is reduced with lithium aluminum hydride and then treated with an organometallic to give alcohols with opposite anti diastereoselection. Boc removal as before provides the final amines of formula type 5b. Alternatively, commercially available epoxides can be opened with nucleophiles to give 5a, where $R^a$ or $R^b$=$CH_2Nu$.

Scheme 1

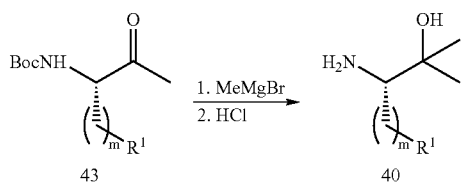

43            40

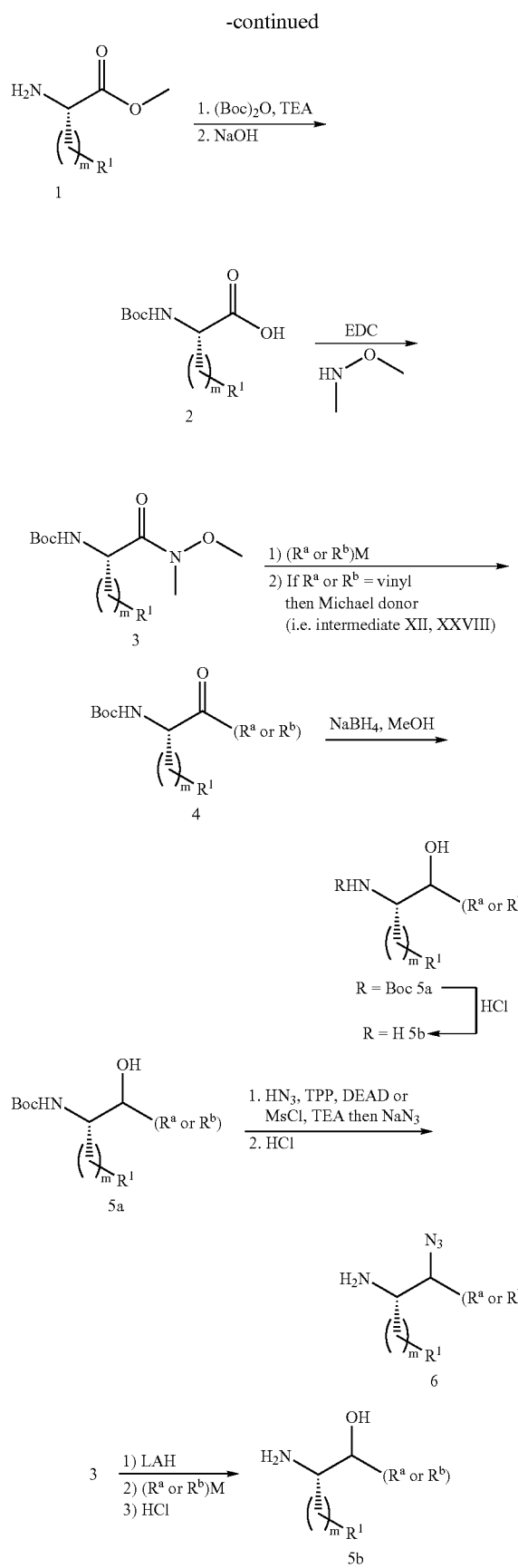

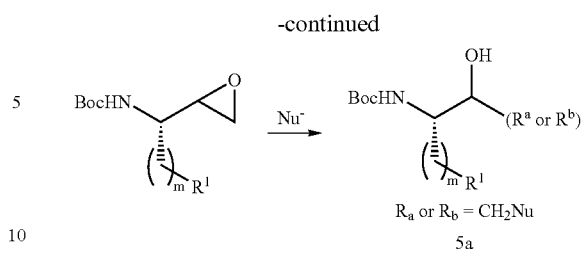

Amino alcohols of type 5b, where $R_a$ and $R_b$=H (Scheme 1), may be obtained directly by reduction of the appropriate α-amino acid or α-amino methylester precursors. Intermediates 5a, where $R^a$ and $R^b$=H obtained after Boc protection and reduction from an appropriate α-amino acid or α-amino methylester precursor, are carried through the Mitsunobu reaction with hydrazoic acid and deprotection as before to give amines of type 6 ($R_a$ and $R_b$=H).

Scheme 2 describes the synthesis of amine 10 which is used in Scheme 4, second step (vide infra). In Scheme 2, propylamine is protected with benzyl chloroformate and subsequently alkylated with crotyl bromide to give 8. Cyclopropanation followed by removal of the protecting group under hydrogenation conditions provides amine of type 10.

Scheme 2

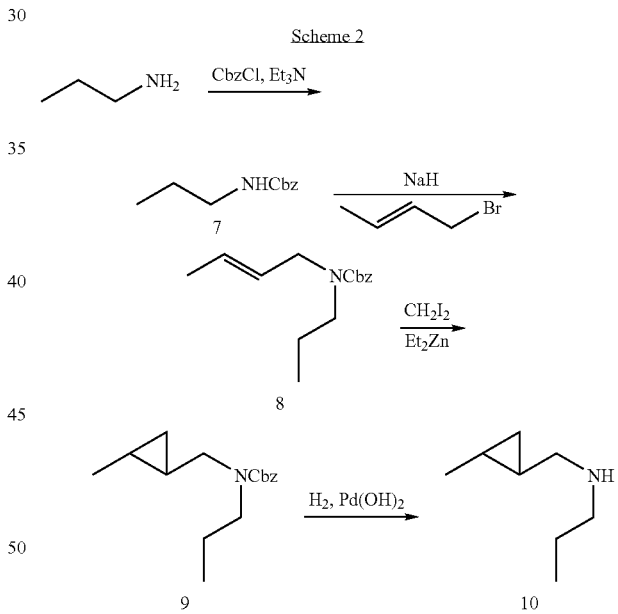

Scheme 3 outlines the synthesis of trans-methyl cyclopropylmethylamine 14. Starting from commercially available trans-crotonoic acid 11 the benzyl amide is generated via EDC coupling. Cyclopropanation using diazomethane and palladium acetate gives the trans-cyclopropane amide 13. Reduction with borane delivers the desired amine 14, which is used as an amine coupling partner in Scheme 4 below. Further elaboration of 14 via amide coupling, borane reduction and hydrogenation of the benzyl group gives substituted amines of type 40 which are also used as coupling partners in Scheme 4. Alternatively, reductive amination of 14 and aldehyde followed by hydrogenation generates amines of type 42.

Scheme 3

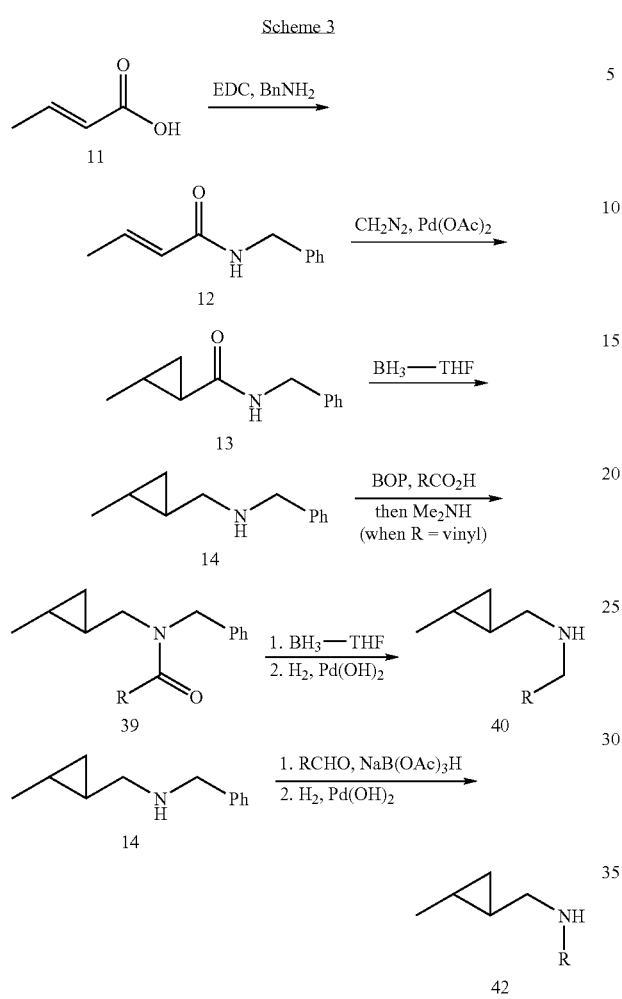

Scheme 4 demonstrates a general route to acids of type 19, 20, 21. The sulfonamide is coupled to methyl dichloroisonicotinate 15 using palladium catalyzed conditions. Ester 16 is then coupled to an amine (which, as an example, can include either 10 or 14) using different palladium catalyzed conditions to give 17. In cases where $R_2$ is a benzyl group, hydrogenation effectively removes the benzyl group to give 18. Saponification of the ester gives acid 19. Alternatively, alkylation of 18 using KHMDS and an alkyl halide introduces a second alkyl group prior to saponifaction to give dialkyl aminopyridine acids of type 19.

Scheme 4

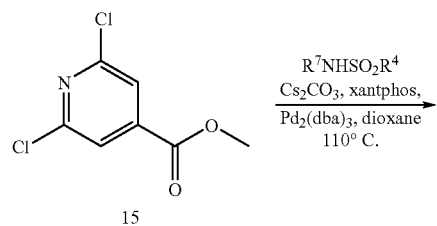

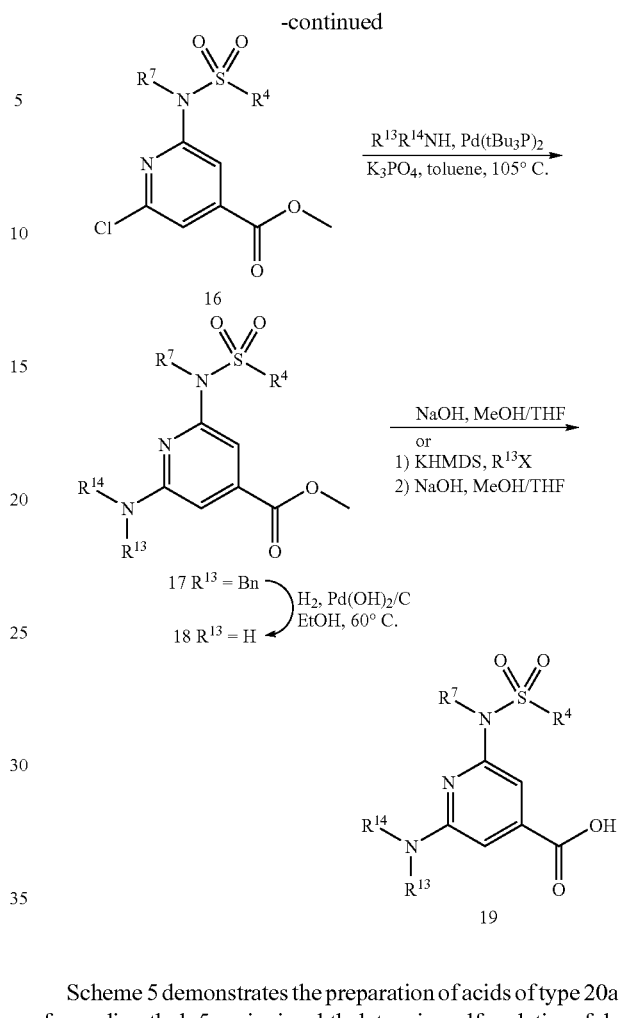

Scheme 5 demonstrates the preparation of acids of type 20a from dimethyl 5-aminoisophthalate via sulfonylation followed by alkylation, hydrolysis, amide coupling and hydrolysis. Alternatively, final example compounds of type 20b can be prepared through incorporation of the $R^2$ group as the final step following a sequence from dimethyl-5-bromoisophthalate involving first mono hydrolysis, followed by amide coupling, hydrolysis, a second amide coupling and a final Pd(0) catalyzed cross-coupling with an appropriate amide. Acid of type 21 is prepared from dimethyl 5-iodoisophthalate via Pd(0) coupling, hydrolysis, amide coupling and a final hydrolysis. Alternatively, final example compounds of the invention of type 22 and 23 can be prepared through installation of the $R^2$ biaryl as the final step following a sequence involving first monohydrolysis, followed by amide coupling, hydrolysis, a second amide coupling and a final Suzuki Pd(0) catalyzed cross-coupling.

Scheme 5

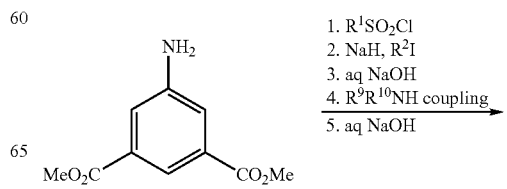

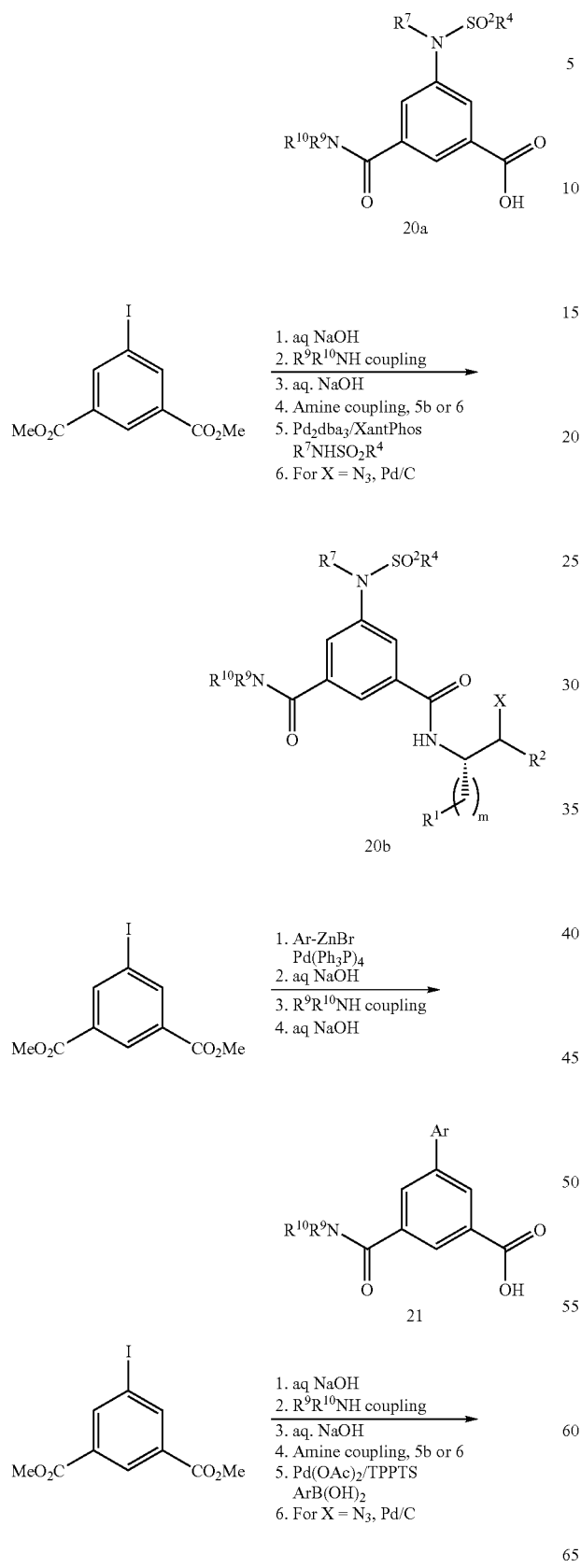

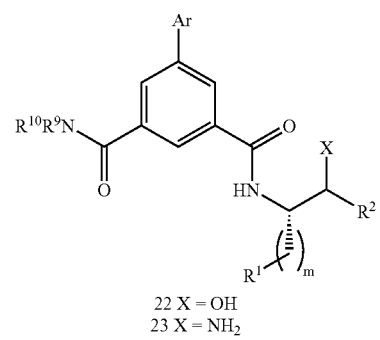

Scheme 6 illustrates the preparation of acids of type 27 and 31. Acid of type 27 may be prepared via first alkylation of phenol 24 followed by conversion of the methyl ester to a bromomethyl functionality to give access to intermediate 25. The cyano-cycloalkyl group is introduced via TMS-CN and the necessary dibromoalkane. Subsequent cyclopropanation followed by hydrolysis provides desired acid 27. The preparation of acid 31 relies on similar methodology regarding the $R^7$-bearing side chain and a Curtius rearrangement for the introduction of $R^7NSO_2R^4$.

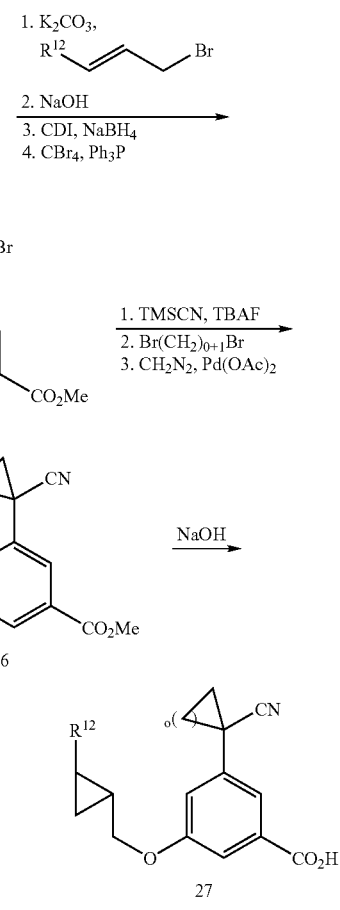

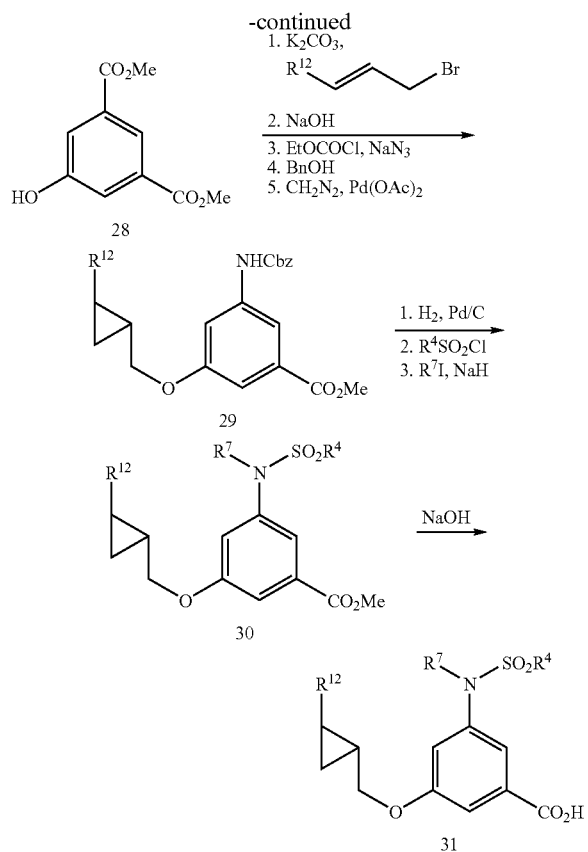

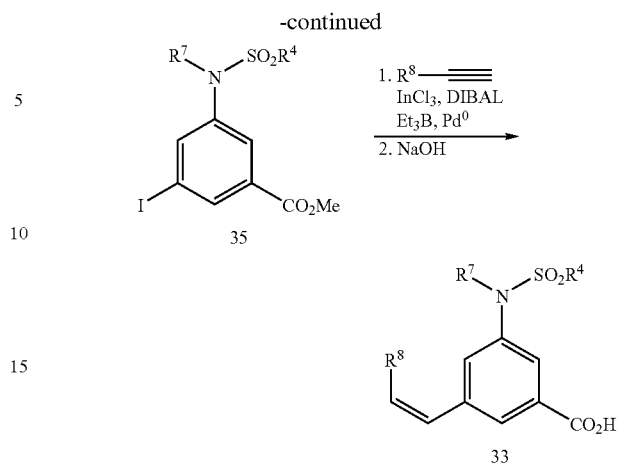

Scheme 8 depicts a final assembly of examples of type 36 and 38. Amide coupling of acids of type 'A-H' with amines of type 5b gives compounds of the general formula 36. Amide coupling of acids of type 'A-H' with amines of type 6 gives the azide 37, which after hydrogenation with palladium on carbon generates amines of the general formula 38. In cases where acid of type Intermediate A (or derivatives thereof) is used, treatment with N-chlorosuccinimide or SelectFluor™ gives the 3-chloro or fluoro pyridine derivative 43 preferentially.

Scheme 7 illustrates two alternative preparations of acid of type 33. The first preparation relies on conversion of the methyl ester to an aldehyde and a Wittig coupling to install the $R^8$-bearing alkene. The second preparation is based on an indeniun/palladium coupling strategy.

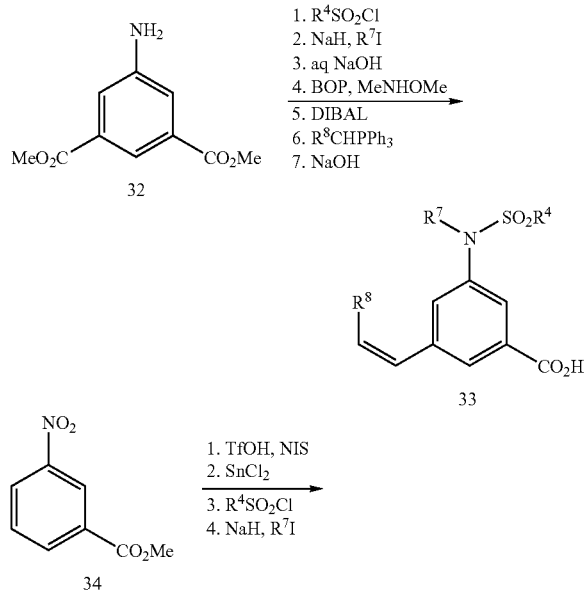

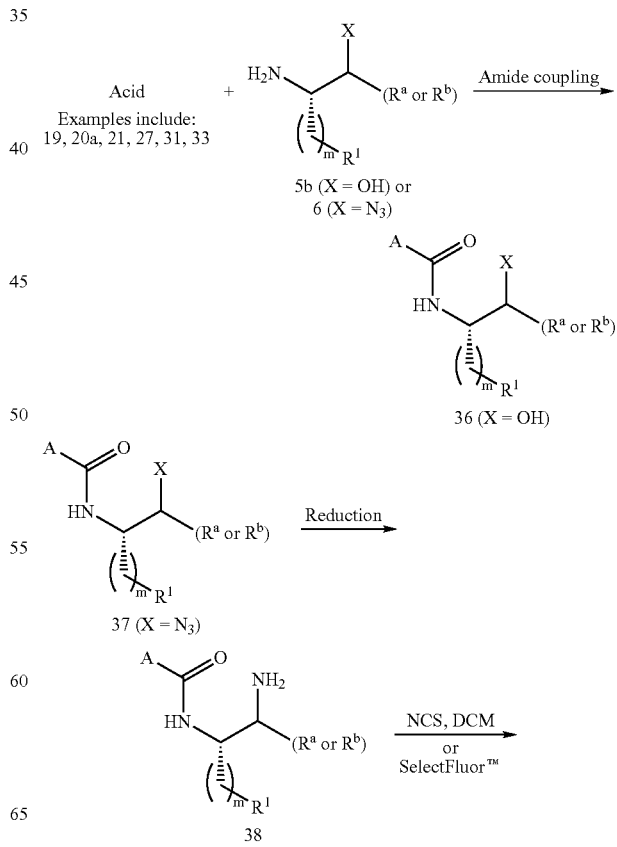

-continued

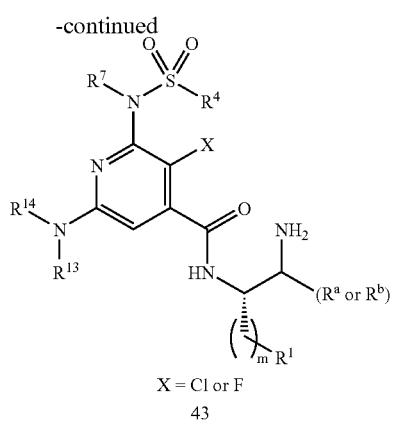

X = Cl or F

43

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; neuronal nicotinic agonists; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing, treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 µM of the substrate, and buffer (50 mM NaOAc, pH 4.5, 0.1 mg/ml BSA, 0.2% CHAPS, 15 mM EDTA and 1 mM deferoxanine) in a total reaction volume of 100 µl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency of compounds, solutions of inhibitor in DMSO (four concentrations of the inhibitors are prepared: 1 mM, 100 µM, 10 µM, 1 µM) are included in the reactions mixture (final DMSO concentration is 0.8%). All experiments are conducted at room temperature using the standard reaction conditions described above. To determine the $IC_{50}$ of the compound, competitive equation V0/Vi=1+[I]/[IC50] are used to predict the inhibitory potency of the compounds. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 µM and can not be determined due to the limit of solubility of the substrate. A typical reaction contains approximately 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the reaction is stopped by the addition of 25 µL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by FRET) are included in the reaction mixture (final DMSO concentration is 10%). All experiments are conducted at room temperature using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assays, generally with an $IC_{50}$ from about 1 nM to 100 µM. Such a result is indicative of the intrinsic activity of the compounds in use as inhibitors of the beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Ar: aryl
Ph: phenyl
Me: methyl
Et: ethyl
Bu: butyl
Ac: acetyl
Bn: benzyl
DMF: N,N'-dimethyl formamide
THF: tetrahydrofuran
DMSO: dimethylsulfoxide
HPLC: high performance liquid chromatography
EDTA: ethylene diamine tetraacetic acid
Boc: tert-butyloxy carbonyl
Cbz: Benzyloxycarbonyl
DIBAL: diisobutylaluminium hydride
BOP: Benzotriazol-1-yloxy-tris(dimethylamino)phosphonium hexafluorophosphate
TMS: trimethylsilyl
BSA: bovine serum albumin
CHAPS: 3-[(3-cholamidopropyl)dimethylammonio]-2-hydroxy-1-propanesulfonate
TEA: triethylamine
EDC: 1-ethyl-3-(3-dimethylaminopropyl)-carbodiimide
LAH: lithium aluminum hydride
TPPTS: triphenylphosphine trisulfonate NIS: N-iodo succinimide
DEAD: diethylazole dicarboxylate
TPP: triphenyl phosphate
KHMDS: potassium bis(trimethylsilyl)amide
dba: di-n-butylamine
DIPEA: diisopropylethylamine
RT: room temperature
DCM: dicholromethane
TfOH: trifluoromethane sulfonic acid
HOAT: 1-hydroxy-7-azabenzotriazole
Nu: nucleophile Intermediate I:
(2S,3S)-3-azido-1-phenylheptan-2-amine (Scheme 1)

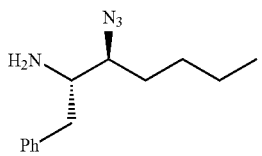

Step A: Ketone Preparation

To a solution of N-Boc-phenylalanine-Weinreb amide (2.19 g, 7.10 mmol) in 50 mL Et$_2$O cooled to −78° C. was added nBuLi (15.5 mL, 24.86 mmol, 1.6 M in hexane) dropwise, via syringe. After stirring at −78° C. for 3 h, an additional 10 mL nBuLi was added and the reaction mixture was stirred at −78° C. for 1 h. The reaction mixture was quenched with water, allowed to warm to room temperature, diluted with water, Et$_2$O and EtOAc, the organic layer was extracted, washed with 10% KHSO$_4$, aq NaHCO$_3$, and brine, dried over sodium sulfate, and concentrated in vacuo to afford crude tert-butyl (1S)-1-benzyl-2-oxohexylcarbamate as a pale yellow oil which was used as is in the following reduction step.

Step B: Reduction

To a solution of tert-butyl (1S)-1-benzyl-2-oxohexylcarbamate (1.81 g, 5.93 mmol) in 65 mL ethanol cooled to −78° C. was added NaBH$_4$ (269 mg, 7.11 mmol). The reaction mixture was stirred at −78° C. for 24 h and allowed to slowly warm to room temperature. The reaction mixture was quenched with 2.5 mL water and concentrated in vacuo. The reaction mixture was partitioned between water and EtOAc, the organic layer was washed with brine, dried over sodium sulfate, and concentrated in vacuo, combined with a previous 440 mg tert-butyl (1S)-1-benzyl-2-oxohexylcarbamate probe reaction, and purified by flash chromatography (300 g silica, 0−>30% EtOAc/hexanes, then repeat on mix: 165 g silica, 10−>40% EtOAc/hexanes) to afford the anti diastereoisomer and the desired syn isomer tert-butyl (1S,2R)-1-benzyl-2-hydroxyhexylcarbamate as a white solid. $^1$H NMR (400 MHz, CDCl$_3$) δ 7.32-7.06 (m, 5H), 4.68-4.48 (m, 1H), 3.88-3.75 (m, 1H), 3.75-3.64 (m, 1H), 2.89 (A of ABX, dd, J=14.0, 4.4 Hz, 1H), 2.80-2.75 (m, B of ABX, 1H), 2.50 (br s, 1H), 1.60-1.20 (m, 6H), 1.35 (s, 9H), 0.52 (t, J=7.0 Hz, 3H).

Step C: Azide Introduction

To a solution of tert-butyl (1S,2R)-1-benzyl-2-hydroxyhexylcarbamate (1.24 g, 4.03 mmol), triphenylphosphine (1.06 g, 4.03 mmol) in 40 mL THF was added hydrozoic acid HN$_3$ (4 mL, 8.07 mmol, 2M in benzene) followed by dropwise addition of diethylazodicarboxylate (0.7 mL, 4.44 mmol) in 10 mL THF. The reaction mixture was stirred at room temperature for 8 h, combined with a previous 250 mg tert-butyl (1S,2R)-1-benzyl-2-hydroxyhexylcarbamate probe reaction, concentrated in vacuo, and purified by flash chromatography (120 g silica, 0−>50% EtOAc/hexanes) to afford tert-butyl (1S,2R)-1-benzyl-2-hydroxyhexylcarbamate and tert-butyl (1S,2S)-2-azido-1-benzylhexylcarbamate as a white solid. $^1$H NMR (400 MHz, CDCl$_3$) δ 7.36-7.16 (m, 5H), 4.63 (d, J=10.1 Hz, 1H), 4.00-3.88 (m, 1H), 3.40-3.28 (m, 1H), 2.91 (A of ABX, dd, J=13.6, 6.8 Hz, 1H), 2.76 (B of ABX, dd, J=13.6, 9.1 Hz, 1H), 1.70-1.48 (m, 2H), 1.42-1.20 (m, 4H), 1.39 (s, 9H), 0.52 (t, J=7.1 Hz, 3H).

Step D: Boc Removal

Through a solution of tert-butyl (1S,2S)-2-azido-1-benzylhexylcarbamate (478 mg, 1.44 mmol) in 50 mL EtOAc cooled to 0° C. was bubbled HCl(g) for 5 min. The reaction mixture was allowed to warm to room temperature, concentrated in vacuo to afford (2S,3S)-3-azido-1-phenylheptan-2-amine hydrochloride I as a white solid. $^1$H NMR (400 MHz, CD$_3$OD) δ 7.42-7.35 (m, 2H), 7.26-7.35 (m, 3H), 3.60-3.51 (m, 2H), 3.08-2.95 (m, 2H), 1.80-1.61 (m, 2H), 1.45-1.26 (m, 4H), 0.92 (t, J=7.7 Hz, 3H).

Intermediate II:
(2S,3R)-3-azido-1-phenylheptan-2-amine (Scheme 1)

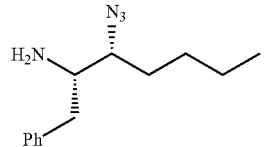

Prepared from the anti diastereoisomer tert-butyl (1S,2S)-1-benzyl-2-hydroxyhexylcarbamate (intermediate I, step B) using a similar procedure as described in intermediate I steps C and D. ES MS (M+H)=233.

Intermediate III:
(2S,3S)-3-hydroxy-1-phenylheptan-2-amine (Scheme 1)

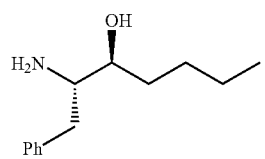

Prepared from the Boc removal of the anti diastereoisomer tert-butyl (1S,2S)-1-benzyl-2-hydroxyhexylcarbamate (intermediate I, step B) using a similar procedure as described in intermediate I step D. ES MS (M+H)=208.

Intermediate IV:
(2S,3R)-3-hydroxy-1-phenylheptan-2-amine
(Scheme 1)

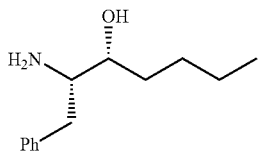

Prepared from the Boc removal of the syn diastereoisomer tert-butyl (1S,2R)-1-benzyl-2-hydroxyhexylcarbamate (intermediate I, step B) using a similar procedure as described in intermediate I step D. ES MS (M+H)=208.

Intermediate V: (2R,3S)-3-azido-1-thien-3-ylheptan-2-amine (Scheme 1)

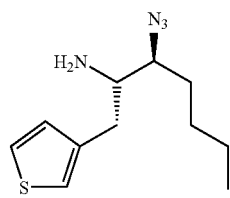

Prepared from Boc aminoacid in manner similar to that used to prepare Intermediate I: ES MS (M+H)=239.

Intermediate VI: (2R,3S)-3-azido-1-thien-3-ylbutan-2-amine (Scheme 1)

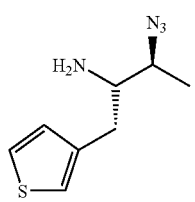

Prepared from Boc aminoacid in a manner similar to that used to prepare Intermediate I: ES MS (M+H)=197.

Intermediate VII: (2R,3S)-2-amino-1-thien-3-ylheptan-3-ol (Scheme 1)

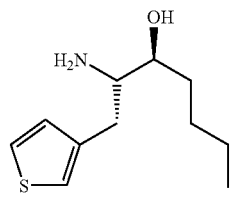

Prepared from the Boc removal of the anti diastereoisomer tert-butyl (1R,2S)-2-hydroxy-1-(thien-3-ylmethyl)hexylcarbamate using a similar procedure as described in intermediate I step D. ES MS (M+H)=214.

Intermediate VIII: (1R,2S)-2-azido-1-(3,5-difluorobenzyl)hexylamine (Scheme 1)

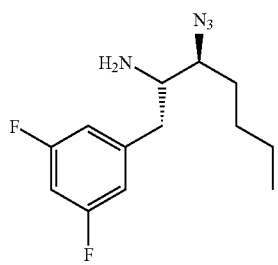

Prepared from Boc aminoacid in manner similar to that used to prepare Intermediate I: ES MS (M+H)=269.

Intermediate IX: (2R,3S)-2-amino-1-(3,5-difluorophenyl)heptan-3-ol (Scheme 1)

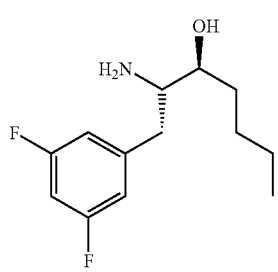

Prepared from the Boc removal of the anti diastereoisomer tert-butyl (1R,2S)-1-(3,5-difluorobenzyl)-2-hydroxyhexylcarbamate using a similar procedure as described in intermediate I step D. ES MS (M+H)=244.

Intermediate X:
N-[(2-methylcyclopropyl)methyl]propan-1-amine
(Scheme 2)

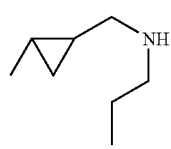

Step A: Cbz Protection

A solution of propylamine (9.0 g, 152.4 mmol) and triethylamine (15.4 g, 152.4 mmol) in methylene chloride (350 mL) was cooled to 0° C. and treated with benzyl chloroformate (20.0 g, 117.2 mmol). Upon stirring at 0° C. for 1 hour the reaction was warmed to ambient temperature and quenched with 1N HCl. The reaction was partitioned between 1N HCl and methylene chloride. The organics were washed with 1N HCl, water and brine. The combined organics were dried over sodium sulfate, filtered and evaporated in vacuo to give benzyl propylcarbamate as a clear oil. $^1$H NMR (400 MHz, CDCl$_3$) δ 7.37 (m, 5H), 5.10 (s, 2H), 4.77 (bs, 1H), 3.16 (q, J=6.5 Hz, 2H), 1.52 (m, 2H), 0.92 (t, J=7.5 Hz, 3H).

Step B: Alkylation

A solution of benzyl propylcarbamate (20.8 g, 107.9 mmol) in DMF (200 mL) was cooled to 0° C. and treated with sodium hydride (4.6 g, 194.2 mmol). The reaction was stirred to 0° C. for 15 minutes and subsequently treated with crotyl bromide (17.5 g, 129.5 mmol). The reaction was warmed to ambient temperature and stirred for 16 hours. The reaction was quenched with ammonium chloride solution and partitioned between water and ether. The organics were washed with water (4×) and brine, dried over sodium sulfate, filtered and evaporated in vacuo. Flash chromatography (silica, 0-10% EtOAc/hexanes) gave benzyl (2E)-but-2-enyl(propyl)carbamate as a clear oil. $^1$H NMR (400 MHz, CDCl$_3$) δ 7.35 (m, 5H), 5.57 (bt, 1H), 5.42 (bs, 1H), 5.13 (s, 2H), 3.82 (bm, 2H), 3.19 (bs, 2H), 1.68 (bs, 3H), 1.54 (bs, 2H), 0.87 (bs, 3H).

Step C: Cyclopropanation

A solution of benzyl (2E)-but-2-enyl(propyl)carbamate (5.0 g, 20.2 mmol) in methylene chloride (120 mL) was cooled to 0° C. and treated with diethylzinc (12.48 g, 101 mmol) followed by diiodomethane (54.1 g, 202 mmol). The reaction was warmed to ambient temperature and stirred for 16 hours. The reaction was quenched with saturated ammonium chloride solution and partitioned between methylene chloride and saturated sodium bicarbonate solution. The organics were dried over sodium sulfate, filtered and evaporated in vacuo. Flash chromatography (10% EtOAc/hexanes) gave 5.16 g (96%) of benzyl (2-methylcyclopropyl)methyl(propyl)carbamate as a yellow oil. $^1$H NMR (400 MHz, CDCl$_3$) δ 7.35 (m, 5H), 5.13 (s, 2H), 3.16 (bm, 4H), 1.59 (bm, 2H), 1.01 (bs, 3H), 0.88 (bs, 3H), 0.68 (bs, 2H), 0.34 (bd, 1H), 0.22 (bs, 2H).

Step D: Hydrogenation

A solution of benzyl (2-methylcyclopropyl)methyl(propyl)carbamate (5.5 g, 21.0 mmol), 10% palladium on carbon (0.25 g) and 12M HCl (3.0 mL) in degassed methanol (100 mL) was placed under a hydrogen atmosphere for 16 hours. The reaction was degassed with nitrogen, filtered through celite, rinsed with methanol and evaporated in vacuo to give 2.61 g (97%) of N-[(2-methylcyclopropyl)methyl propan-1-amine hydrochloride. The salt was partitioned between 1M NaOH and ether. The organics were dried over sodium sulfate, filtered and evaporated in vacuo to give N-[(2-methylcyclopropyl)methyl propan-1-amine. $^1$H NMR (400 MHz, CD$_3$OD) δ 2.50 (m, 4H), 1.54 (m, 2H), 1.05 (m, 3H), 0.93 (m, 3H), 0.62 (m, 2H), 0.33 (m, 1H), 0.24 (m, 1H).

Intermediate XI:
N-benzyl-1-(2-trans-methylcyclopropyl)methanamine
(Scheme 3)

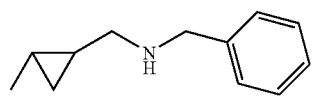

Step A: Coupling

In a 2 L flask trans-crotonoic acid (15.0 g, 174 mmol), benzyl amine (20.5 g, 192 mmol) and DIPEA (36.7 g, 192 mmol) were dissolved in 700 mL of dichloromethane. To this solution at room temperature EDC-HCl (36.7 g, 192 mmol) was added as a solid portionwise and stirred overnight. The reaction mixture was poured onto 10% aq. KHSO$_4$ (250 mL). The layers were separated and washed once again with 10% aq. KHSO$_4$. The organic layer was subsequently washed with H$_2$O (200 mL) followed by brine (150 mL), dried over Na$_2$SO$_4$ and concentrated to dryness to white crystals of (2E)-N-benzylbut-2-enamide: $^1$H NMR (400 MHz, CDCl$_3$) δ 7.28 (m, 5H), 6.85 (sext, J=6.8 Hz, 1H), 5.78 (dd, J=15.2, 1.6 Hz, 2H), 4.47 (d, J=5.6 Hz, 2H), 1.82 (dd, J=7.2, 1.6 Hz, 3H).

Step B: Cyclopropanation

In an Erlenmeyer flask containing Et$_2$O (300 mL) and aq. 40% KOH (111 mL) with vigorous stirring was added 1-methyl-3-nitro-1-nitrosoguanidine (11.1 g, 67 mmol) portionwise over 5 min. at room temperature. Upon complete addition stirring was ceased and the aq. layer frozen in a −78 deg bath. The ether layer was decanted into an Erlenmeyer with KOH pellets. The contents allowed to stand for 5 min., decanted into a third flask with KOH pellets and then poured onto a Et$_2$O/THF solution (200 mL/50 mL) containing (2E)-N-benzylbut-2-enamide (3.0 g, 17.1 mmol from step A). Pd(OAc)$_2$ (180 mg, 0.9 mmol) was subsequently added and the reaction allowed to warm to rt and stir for 1 h. Nitrogen was bubbled through the reaction for 10 min. The mixture was washed with H$_2$O (150 mL). The organic layer was isolated and subsequently dried over Na$_2$SO$_4$. Solvent removal and purification by flash chromatography on SiO$_2$ (EtOAc/hexanes) gave N-benzyl-trayis-2-methylcyclopropanecarboxamide (83%): $^1$H NMR (400 MHz, CDCl$_3$) δ 7.28 (m, 5H), 5.81 (br s, 1H), 4.43 (dd, J=5.6, 2.4 Hz, 2H), 1.37 (m, 1H), 1.17 (m, 1H), 1.07 (d, J=6.0 Hz, 3H), 1.04 (overlapping m, 1H), 0.56 (m, 1H).

Step C: Reduction

A 500 mL flask charged with N-benzyl-trans-2-methylcyclopropanecarboxamide (from step B, 3.9 g, 20.6 mmol) in THF (80 mL) was added BH$_3$-THF (1.0 M, 105 mL, 105 mmol) dropwise via an addition funnel. Upon complete addition (10 min.) the mixture was refluxed for 5 h. The mixture was allowed to cool to room temperature and quenched carefully with MeOH (15 mL).

The mixture was concentrated to dryness, dissolved in dichloromethane and washed with 3M KOH. The organic layer was isolated, washed with brine, then dried over Na$_2$SO$_4$ and concentrated to dryness. The crude material was treated with 1N HCl in dioxane for 1 h at 50° C. The mixture was concentrated to give hydrochloride salt as a white solid. The solid was dissolved in sat. aq. NaHCO$_3$ (80 mL) and extracted with CHCl$_3$ (2×150 mL). The combined organic layers were washed with brine, dried over Na$_2$SO$_4$ and the solvent removed via rotorary evaporation to give after drying in vacuo N-benzyl-1-(2-trans-methylcyclopropyl)methanamine as an off-white semi-solid (quant.): $^1$H NMR (400 MHz, CDCl$_3$) δ 7.28 (m, 5H), 3.80 (s, 2H), 2.50 (d, J=6.8 Hz, 2H), 2.4 (br s, 1H), 1.02 (d, J=6.0 Hz, 3H), 0.69 (m, 1H), 0.52 (m, 1H), 0.23 (m, 2H).

Intermediate XII: N-(2S,3RS)-2-amino-5-(dimethylamino)-1-phenylpentan-3-ol (Scheme 1)

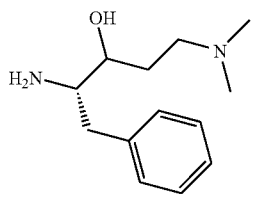

Prepared according to Scheme 1 in an analogous manner as intermediate III with the one additional step; step B involving Michael addition using dimethyl amine (vida infra).

Step A: To a solution of N-Boc-phenylalanine-Weinreb amide (10.0 g, 32.4 mmol) in 200 mL THF cooled to −40° C. was added vinyl magnesium bromide (97.0 mL, 97.0 mmol, 1.0 M in THF) dropwise. After stirring at −40 to −20° C. for 5 h. The reaction mixture was poured onto cold 3N HCl (600 mL), extracted with EtOAc (3×200 mL), the organic layers combined and washed with brine, dried over sodium sulfate, and concentrated in vacuo to afford crude tert-butyl (1S)-1-benzyl-2-oxobut-3-enylcarbamate which was used as is in the following Michael addition reaction.

Step B: In a flask containing tert-butyl (1S)-1-benzyl-2-oxobut-3-enylcarbamate (0.75 g, 2.72 mmol) in MeOH (10 mL) was added dimethyl amine (2.73 mL, 2.0 M MeOH, 5.45 mmol). The mixture was stirred at rt for 1 h. The mixture was concentrated to dryness to give tert-butyl (1S)-1-benzyl-4-(dimethylamino)-2-oxobutylcarbamate which was used in the next reaction without further purification.

Step C: In a 50 mL flask containing ketone (825 mg, 2.57 mmol) from step B in 25 mL of EtOH at room temperature was added NaBH$_4$ (92 mg, 2.57 mmol) in two portions. The mixture was stirred overnight and 1mL of H$_2$O added. The reaction was concentrated to dryness and partitioned between EtOAc and H$_2$O. The layers were separated and the aqueous layer extracted once again. The combined organic layers were washed with brine, dried over Na$_4$SO$_4$ and concentrated to dryness to give crude tert-butyl (1S,2RS)-1-benzyl-4-(dimethylamino)-2-hydroxybutylcarbamate. $^1$H NMR indicated a mixture of alpha and beta diastereomers. The crude material was deprotected in step D below without further purification.

Step D: A scintillation vial containing tert-butyl (1S,2RS)-1-benzyl-4-(dimethylamino)-2-hydroxybutylcarbamate (250 mg, 0.78 mmol) in EtOAc was cooled to 0° C. HCl (g) was gently bubbled into the mixture for ca. 1 min. The vial was sealed with a cap and allowed to warm to rt. After 30 min. the mixture was concentrated with N$_2$ and then concentrated further via rotorary evaporation to give an off-white solid intermediate XII, N-(2S,3RS)-2-amino-5-(dimethylamino)-1-phenylpentan-3-ol as hydrochloride salt: (2:1 ratio of diastereomers, major isomer reported) $^1$H NMR (400 MHz, MeOD) δ 7.28 (m, 5H), 3.91 (dt, J=6.9 Hz, 3.6 Hz, 1H), 3.61 (m, 1H), 3.35 (m, 2H) 3.22 (m, 2H), 2.9-3.0 (overlapping m, 2H), 2.89 (s, 6H); ES MS (M+H)=223.3.

Intermediate XIII: (2S,3R)-3-azido-1-phenylbutan-2-amine (Scheme 1)

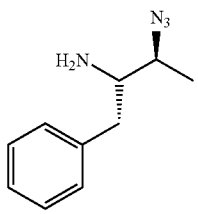

Prepared from Boc aminoacid in manner similar to that used to prepare Intermediate I: ES MS (M+H)=191.

Intermediate XIV: (2S,3R)-3-azido-4-fluoro-1-phenylbutan-2-amine (Scheme 1)

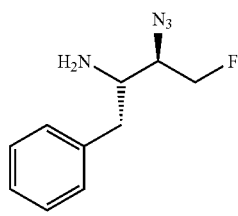

Step A: Epoxide Opening tert-Butyl[(1S)-1-oxiran-2-yl-2-phenylethyl]carbamate (1.0 g, 3.8 mmol), potassium fluoride hydrogen fluoride (0.59 g, 7.6 mmol) and N,N,N-tributylbutan-1-aminium fluoride dihydrofluoride (0.06 g, 0.19 mmol) in chlorobenzene (2.0 mL) was heated to 120° C. for 16 hours. The reaction was cooled to ambient temperature, diluted with methylene chloride, filtered through celite and evaporated in vacuo. Flash column chromatography (silica, 25% ethyl acetate/hexanes) generated 0.29 g (27%) of desired alcohol as a white solid. $^1$H NMR (400 MHz, CDCl$_3$) δ 7.28 (m, 5H), 4.61 (bs, 1H), 4.54 (m, 1H), 4.43 (m, 1H) 3.93 (bm, 2H), 3.24 (bs, 1H), 2.93 (bm, 2H), 1.38 (s, 9H); ES MS (M+H−tBu)=228.3.

Prepared by analogous steps C and D in intermediate I: ES MS (M+H)=209.3.

Intermediate XV: (2-methoxyethlyl)[(2-methylcyclopropyl)methyl]amine (Scheme 3)

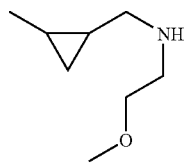

Step A: Coupling

In a 500 mL flask methoxyacetic acid (2.24 g, 24.8 mmol), N-benzyl-1-(2-trans-methylcyclopropyl)methanamine hydrochloride (5.0 g, 23.6 mmol) and DIPEA (13.4 g, 104 mmol) were dissolved in 300 mL of dichloromethane. To this solution at rt BOP (11.0 g, 24.8 mmol) was added as a solid portionwise and stirred 15 minutes. The reaction mixture was evaporated ini vacuo. Purification by flash chromatography (25-35% ethyl acetate:hexanes) provided a mixture of cis and trans amides as a clear oil: ES MS (M+H)=248.1.

Step B: Reduction

A 500 mL flask charged with N-benzyl-2-methoxy-N-(2-methoxycyclopropyl)methyl acetamide (from step A, 7.75 g, 31.3 mmol) in THF (100 mL) was added BH$_3$-THF (1.0 M, 94 mL, 94 mmol) dropwise via an addition funnel. Upon complete addition (10 min.) the mixture was refluxed for 14 h. The mixture was allowed to cool to rt and quenched carefully with MeOH (15 mL). The mixture was then treated with 15 mL concentrated HCl and heated to reflux for 5 h. The reaction was evaporated in vacuo and partitioned between ethyl acetate and 20% NaOH solution. The aqueous layer was washed with ethyl acetate (3×). The combined organics were dried over sodium sulfate, filtered and evaporated in vacuo. Purification by reverse phase LC gave N-benzyl-2-methoxy-N-(2-methylcyclopropyl)methylethanamine as a clear oil: $^1$H NMR (400 MHz, CDCl$_3$) δ 7.28 (m, 5H), 3.70 (bq, J=13.5 Hz, 2H), 3.49 (bs, 2H), 3.31 (s, 3H), 2.75 (bm, 2H), 2.51 (m, 1H), 2.31 (m, 1H), 1.03 (d, J=5.86, 3H), 0.59 (m, 1H), 0.48 (m, 1H), 0.22 (m, 2H). ES MS (M+H)=234.2.

Step C: Hydrogenation

A degassed solution of N-benzyl-2-methoxy-N-(2-methylcyclopropyl)methylethanamine (4.89 g, 20.9 mmol) in 150 mL ethyl alcohol was treated with palladium hydroxide (20% on carbon, 0.29 g) and hydrogen chloride (5.24 mL of a 4M solution in dioxane, 21 mmol) then placed under a hydrogen atmosphere for 16 hours. The reaction mixture was degassed with nitrogen, filtered through celite, washed with methanol and evaporated in vacuo to give (2-methoxyethyl)[(2-methylcyclopropyl)methyl]amine hydrochloride as a pale yellow oil: $^1$H NMR (400 MHz, CD$_3$OD) δ 3.65 (m, 2H), 3.41 (s, 3H), 3.21 (m, 2H), 2.92 (m, 2H), 1.09 (d, J=5.68 Hz, 3H), 0.80 (m, 2H), 0.57 (m, 1H), 0.46 (m, 1H).

Intermediate XVI: (2-fluoroethyl)[(2-methylcyclopropyl)methyl]amine (Scheme 3)

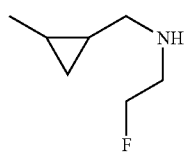

Prepared from fluoroacetic acid in a manner analogous to that used in the preparation of intermediate XV. $^1$H NMR (400 MHz, CDCl$_3$) δ 4.98 (bd, J=46.3 Hz, 2H), 3.42 (bm, 2H), 3.02 (bs, 2H), 1.12 (bs, 3H), 1.01 (bs, 1H), 0.88 (bs, 1H), 0.66 (bs, 1H), 0.51 (bs, 1H).

Intermediate XVII: (2,2-difluoroethyl)[(2-methylcyclopropyl)methyl]amine (Scheme 3)

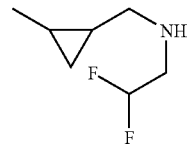

Prepared from difluoroacetic acid in a manner analogous to that used in the preparation of intermediate XV. $^1$H NMR (400 MHz, CD$_3$OD) δ 6.31 (t, J=48 Hz, 1H), 3.56 (td, J=15.6, 3.1 Hz, 2H), 3.31 (m, 2H), 1.11 (d, J=5.9 Hz, 3H), 0.83 (m, 2H), 0.60 (m, 1H), 0.49 (m, 1H).

Intermediate XVIII: N,N-dimethyl-N'-[(2-methylcyclopropyl)methyl]ethane-1,2-diamine (Scheme 3)

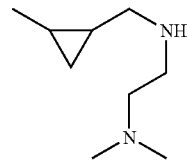

Prepared from N,N-dimethylglycine in a manner analogous to that used in the preparation of intermediate XV. $^1$H NMR (400 MHz, CD$_3$OD) δ 3.49 (m, 4H), 2.98 (m, 2H), 2.96 (s, 6H), 1.09 (d, J=5.8 Hz, 3H), 0.83 (m, 2H), 0.61 (m, 1H), 0.49 (m, 1H).

Intermediate XIX: N,N-dimethyl-N'-[(2-methylcyclopropyl)methyl]propane-1,3-diamine (Scheme 3)

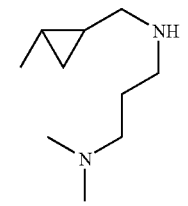

Step A: Coupling

In a 100-mL flask acrylic acid (0.17 g, 2.4 mmol), N-benzyl-1-(2-trans-methylcyclopropyl)methanamine (0.5 g, 2.4 mmol) and DIPEA (0.64 g, 4.9 mmol) were dissolved in 20 mL of dichloromethane. To this solution at room temperature EDC (0.68 g, 3.5 mmol) was added as a solid portionwise and stirred 15 hours. The reaction was partitioned between 1M HCl and methylene chloride. The organics were dried over sodium sulfate, filtered, concentrated in vacuo and carried into next reaction crude.

Step B: Michael Addition.

In a 50-mL flask acrylamide (crude from step A) in methanol (10 mL) was treated with dimethylamine (4.5 mmol, 2.2 mL of a 2M solution in methanol). The reaction was stirred for 1 hour at ambient temperature then concentrated in vacuo. The residue was purified by flash column chromatography (2.5-15% MeOH/methylene chloride) to provide $N^1$-benzyl-$N^3$,$N^3$-dimethyl-$N^1$-[(2-methylcyclopropyl)-methyl]-β-alaninamide as a clear oil: $^1$H NMR (400 MHz, CDCl$_3$) δ 7.24 (m, 5H), 4.68 (m, 2H), 3.21 (m, 2H), 2.67 (m, 4H), 2.34 (s, 3H), 2.24 (s, 3H), 0.97 (m, 3H), 0.58 (m, 2H), 0.29 m, 2H). LCMS [M+H]$^+$=275.4.

Step C: Reduction

In a round-bottom flask $N^1$-benzyl-$N_3$,$N_3$-dimethyl-$N^1$-[(2-methylcyclopropyl)-methyl]-β-alaninamide (0.47 g, 1.7 mmol) was dissolved in 10 mL anhydrous THF. To this solution was added BH$_3$-THF (5.1 mmol, 5.1 mL of a 1M solution in THF). The reaction was equipped with a reflux condenser and heated to reflux for 16 hours. The reaction was cooled to 0° C. and quenched with methanol followed by concentrated HCl (5 mL). The resulting mixture was heated to reflux for 16 hours. The crude mixture was then concentrated in vacuo and partitioned between 10% NaOH/ethyl acetate. The organics were dried over sodium sulfate, filtered and evaporated in vacuo. Purification by reverse phase chromatography gave $N^1$-benzyl-$N^3$,$N^3$-dimethyl-$N^1$-[(2-methylcyclopropyl)methyl]propane-1,3-diaminium bis(trifluoroacetate) as a clear oil: LCMS [M+H]$^+$=261.5.

Step D: Hydrogenation

A solution of $N^1$-benzyl-$N^3$,$N^3$-dimethyl-$N^1$-[(2-methylcyclopropyl)methyl]propane-1,3-diaminium bis(trifluoroacetate) (0.42 g, 0.86 mmol) in ethanol (50 mL) was degassed with nitrogen and treated with palladium hydroxide (75 mg). The reaction was placed under a hydrogen atmosphere and stirred vigorously for 1 hour. The reaction was filtered through celite, washed with methanol and concentrated in vacuo to give N,N-dimethyl-N'-[(2-methylcyclopropyl)methyl]propane-1,3-diaminium bis(trifluoroacetate) as a pale yellow oil.

Intermediate XX:
3-amino-2-methyl-4-phenylbutan-2-ol (Scheme 1)

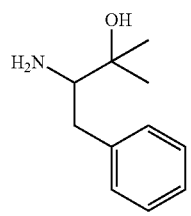

Step A: Grignard Addition

A solution of Boc-3-amino-4-phenyl-2-butanone (0.5 g, 1.9 mmol) in 100 mL methylene chloride was cooled to −78° C. and treated with methyl magnesium bromide (1.39 mL of a 3.0M solution, 4.2 mmol). The reaction was warmed to ambient temperature and stirred for 14 hours. The reaction was charged with additional methyl magnesium bromide (1.39 mL of a 3.0 M solution, 4.2 mmol) and stirred at ambient temperature for 5 hours. The reaction was quenched with ammonium chloride solution and partitioned between water and ethyl acetate. The organics were washed with water (3×), brine, dried over sodium sulfate, filtered and evaporated in vactio. Purification by flash column chromatography (20-35% ethyl acetate/hexanes) gave Boc-3-amino-2-methyl-4-phenylbutan-2-ol as a white solid: $^1$H NMR (400 MHz, CDCl$_3$) δ 7.25 (m, 5H), 4.52 (m, 1H), 3.69 (m, 1H), 3.09 (dd, J=14.1, 3.3 Hz, 1H), 2.61 (t, J=12.0 Hz, 1H), 2.39 (s, 1H), 1.30 (m, 15H).

Step B: Deprotection

A solution of Boc-3-amino-2-methyl-4-phenylbutan-2-ol (0.34 g, 1.2 mmol) in 100 mL ethyl acetate was saturated with HCl gas and stirred at ambient temperature for 1 hour. The reaction was evaporated in vacuo to give 3-amino-2-methyl-4-phenylbutan-2-ol hydrochloride as a white solid: $^1$H NMR (400 MHz, CDCl$_3$) δ 8.05 (bs, 2H), 7.33 (m, 5H), 3.34 (m, 1H), 3.02 (m, 2H), 1.37 (s, 3H), 1.33 (s, 3H).

Intermediate XXI:
methyl[(2-methylcyclopropyl)methyl]amine
(Scheme 3)

Step A: Reductive Amination

A solution of N-benzyl-1-(2-trans-methylcyclopropyl)methanamine hydrochloride (5.0 g, 23.6 mmol) and formaldehyde (19.0 g, 640 mmol) in 60 mL dichloroethane and 30 mL methanol was treated with sodium triacetoxyborohydride (10.0 g, 47.3 mmol). The reaction was stirred at ambient temperature for 1 hour. The reaction was evaporated in vacuo, taken up in ethyl acetate and treated with sodium bicarbonate solution. This mixture was partitioned and the organics washed with brine, dried over sodium sulfate, filtered, treated with HCl in ether (26.0 ml of a 1M solution, 26 mmol) and evaporated in vacuo to give N-benzyl-N-methyl-1-(2-methylcyclopropyl)methanamine hydrochloride as a white solid: ES MS (M+H)=190.1.

Step B: Hydrogenation

Prepared by analogous step C in intermediate XV: $^1$H NMR (400 MHz, CD$_3$OD) δ 2.88 (d, J=7.3 Hz, 2H), 2.68 (s, 3H), 1.10 (d, J=5.7 Hz, 3H), 0.79 (m, 2H), 0.57 (m, 1H), 0.47 (m, 1H).

Intermediate XXII:
(2S,3R)-3-azido-4-ethoxy-1-phenylbutan-2-amine

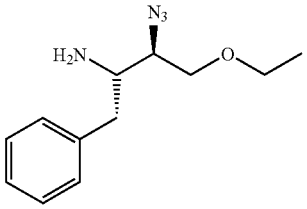

Step A: Epoxide Opening

In a flask charged with NaH (60% dispersion, 0.26 g, 34.1 mmol) in EtOH at 0° C. was added tert-Butyl[(1S)-1-oxiran-2-yl-2-phenylethyl]carbamate (3.0 g, 11.3 mmol) and the reaction allowed to warm to rt and stir overnight. Aqueous NH$_4$Cl (3-5 mL) was added slowly, the reaction stirred for 30 min. and then concentrated to dryness. The crude product was partitioned between EtOAc and water. The organic layer was isolated and washed with brine and dried over Na₂SO₄. Upon solvent removal further drying in vacuo 3.4 g of alcohol tert-butyl [(1S,2S)-1-benzyl-3-ethoxy-2-hydroxypropyl]carbamate was isolated: $^1$H NMR (400 MHz, CDCl₃) δ 7.28 (m, 5H), 4.70 (d, J=8.0 Hz, 1H), 3.89 (m, 1H), 3.71 (m, 1H), 3.51 (m, 3H), 2.89 (d, J=6.0 Hz, 2H), 1.35 (s, 9H), 1.20 (t, J=7.2 Hz, 3H); ES MS (M+H)=310.3.

Step B: Mesylate Formation

To a 10 mL flask containing a CH₂Cl₂ (60 mL) solution of tert-butyl [(1S,2S)-1-benzyl-3-ethoxy-2-hydroxypropyl]carbamate (3.0 g, 9.7 mmol) and mesyl chloride (0.75 mL, 9.7 mmol) was added TEA (1.48 mL, 10.6 mmol) dropwise at rt. The resulting mixture was stirred for 30 min. and then poured onto water. The organic phase was separated and washed again with water followed by brine and concentrated to give 4.0 grams crude (1S,2S)-2-[(tert-butoxycarbonyl)aamino]-1-(ethoxymethyl)-3-phenylpropyl methanesulfonate as a white solid which was used directly without further purification: ES MS (M+H)=388.0.

Step C: Azide Displacement

Crude mesylate (4.0 g, 10.3 mmol) from above and NaN₃ (0.87 g, 13.4 mmol) were dissolved in DMF (15 mL) and the mixture heated at 90° C. for 48 h. The reaction was cooled to rt, quenched with aq. NH₄Cl and extracted repeatedly with EtOAc (3×100 mL). The combined layers were washed with aq. LiCl (2×80 mL), followed by brine and dried over Na₂SO₄. Upon solvent evaporation 3.3 g of an orange oil was obtained containing tert-butyl [(1S,2R)-2-azido-1-benzyl-3-ethoxypropyl]carbamate: ES MS (M+H–tBu)=235.2.

Step D: Boc Deprotection

Crude azide (3.3 g, 9.8 mmol) was dissolved in dioxane (40 mL) and treated with HCl (4.0 N dioxane, 12 mL, 49 mmol). After stirring overnight the mixture was concentrated to dryness. The crude was re-dissolved in CH₂Cl₂ and extracted with 1N HCl (3×100 mL). The combined aqueous layers were treated with 3 M KOH till pH 9.0 and then extracted once again with EtOAc (3×100 mL). The combined organic layers were washed with brine and dried over Na₂SO₄ to give after solvent evaporation 0.8 g of Intermediate XXII as free base: $^1$H NMR (400 MHz, CDCl₃) δ 7.28 (m, 5H), 3.67 (d, J=6.4 Hz, 2H), 3.50 (m, 3H), 3.07 (m, 1H), 2.72 (ABq, $J_{AB}$=13.5 Hz, $J_{AX}$=6.4 Hz, $J_{BX}$=8.0 Hz, 2H), 1.45 (br s, 2H), 1.19 (t, J=6.8 Hz, 3H); ES MS (M+H)=236.2.

Intermediate XXIII:
(2S,3R)-3-azido-4-methoxy-1-phenylbutan-2-amine

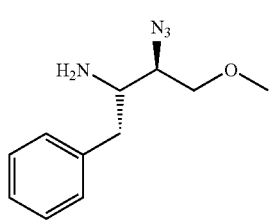

Prepared in a manner to similar to intermediate XXII with steps B and C substituted with an alternative Mitsunobu hydrazoic acid displacement (see Intermediate I step C): ES MS (M+H)=235.3.

Intermediate XXIV:
(2S,3R)-3-azido-4-propoxy-1-phenylbutan-2-amine

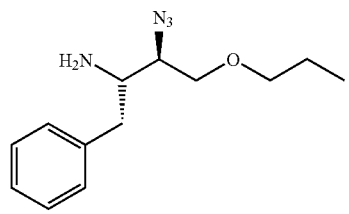

Prepared in a manner to similar to intermediate XXII with steps B and C substituted with an alternative Mitsunobu hydrazoic acid displacement (see Intermediate I step C): ES MS (M+H)=249.6.

Intermediate XXV:
(2S,3R)-3-azido-4-phenoxy-1-phenylbutan-2-amine

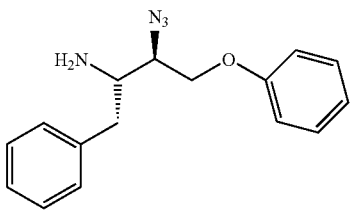

Prepared in a manner to similar to intermediate XXII. Step A employed DMF as solvent and 3 equiv of phenol as nucleophile. Steps B and C were substituted with Mitsunobu hydrazoic acid inversion (see Intermediate I step C): ES MS (M+H) =283.6.

Intermediate XXVI: ((1S,2R)-2-azido-1-benzyl-3-{ [3-(trifluoromethoxy)benzyl]oxy}propyl)amine

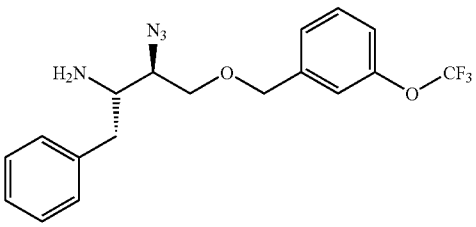

Prepared in a manner similar to intermediate XXII. Step A employed DMF as solvent and 3 equiv of alcohol as nucleophile. Steps B and C were substituted with a Mitsunobu hydrazoic acid inversion (see Intermediate I step C): ES MS (M+H)=381.5.

Intermediate XXVII: [(1S,2S)-2-azido-1-benzyl-5,5,5-trifluoropentyl]amine

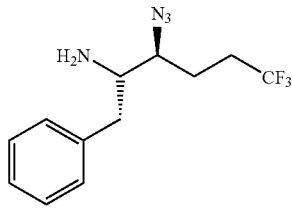

Prepared in a manner similar to intermediate I using freshly prepared Grignard reagent derived from 3,3,3-trifluoropropyl-iodide: ES MS (M+H)=273.1

Intermediate XXVIII: [(1S,2S)-2-azido-1-benzyl-4-(3-chlorophenyl)butyl]amine

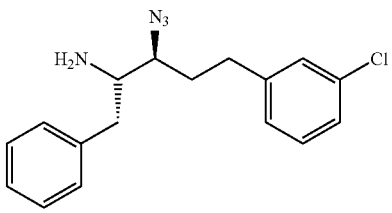

Step A: Ketone Preparation

Performed in a manner similar to Intermediate I step A. Preparation of Weinreb amide followed by vinyl Grignard addition dropwise in THF at −40° C. After stirring for 5 h at −40° C. to −10° C. the reaction was poured gradually onto ice-cold 3N HCl and extracted repeatedly with EtOAc. The organic layers were washed with brine, dried over $Na_2SO_4$ and concentrated to give crude vinyl ketone.

Step B: Rh(I) Catalyzed Michael Addition

A 20 mL Personal chemistry microwave vial charged with 3-chlorophenyl boronic acid (1.13 g, 7.26 mmol), vinyl ketone from step A (1.00 g, 3.63 mmol), rac-BINAP (203 mg, 0.33 mmol) and $Rh(acac)_2(CH_2CH_2)_2$ (56 mg, 0.22 mmol) were sealed and put under an argon atmosphere. To this mixture 16.0 mL degassed dioxane was added. After 15 min. 4.0 mL $H_2O$ was added and the contents heated in microwave at 110° C. for 120 min. The reaction was filtered over Celite, rinsed with EtOAc, and the filtrate extracted with EtOAc. The combined organic layers were washed with brine, dried over $Na_2SO_4$ and concentrated to dryness. The crude material was subsequently purified by automated $SiO_2$ chromatography (EtOAc/hexanes) to give 1.1 grams of tert-butyl [(1S)-1-benzyl-2-oxobut-3-en-1-yl]carbamate: ES MS (M+H−tBu)=288.1

Step C-E: Reduction, Mitsunobu $HN_3$ Inversion and Boc Removal

Performed in a manner similar to Intermediate I steps B-D to give title compound as a white solid ([(1S,2S)-2-azido-1-benzyl-4-(3-chlorophenyl)butyl]aamine): $^1$H NMR (400 MHz, $CD_3OD$) δ 7.14-7.40 (m, 8H), 7.19 (d, J=1.4 Hz, 1H), 3.60 (sext, J=3.6 Hz, 1H), 3.54 (m, 1H), 3.07 (d, J=7.3, 2H), 2.72 (m, 2H), 2.01 (m, 2H); ES MS (M+H)=315.2

Intermediate XXIX: {(1S)-[(1S,2S)-2-methylcyclopropyl]ethyl}amine

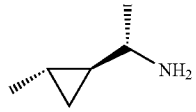

Step A. (2E)-1,1-diethoxybut-2-ene

Crotonaldehyde (23.64 mL, 285.35 mmol), triethyl orthoformate (57.02 mL, 342.42 mmol) and ammonium nitrate (2.28 g, 28.54 mmol) were combined in 60 mL EtOH. After 22 h at ambient temperature, the reaction was diluted with EtOAc (60 mL) and washed with saturated sodium bicarbonate solution (40 mL). The aqueous layer was back extracted with EtOAc (20 mL). The combined organics were washed with brine (40 mL), dried over $Na_2SO_4$, filtered and concentrated in vacuo to give 36.5 g (89%) of 1,1-diethoxybut-2-ene. 1H NMR ($CDCl_3$, 400 MHz) 5.84 (m, 1H); 5.54 (m, 1H); 4.82 (d, J=5.7 Hz, 1H); 3.64 (m, 2H); 3.49 (m, 2H); 1.73 (m, 3H); 1.21 (m, 6H).

Step B. diisopropyl (4S,5S)-2-[(1E)-prop-1-enyl]-1,3-dioxolane-4,5-dicarboxylate A solution of (2E)-1,1-diethoxybut-2-ene (32.20 g, 223.27 mmol), (−)-diisopropyl D-tartrate (64.64 mL, 245.60 mmol) and pyridinium tosylate (2.24 g, 8.93 mmol) in 100 mL benzene was heated to 95° C. to distill off the solvent and EtOH produced. After 7 h at 95° C., the reaction was cooled to rt and concentrated in vacuo. Purification by normal phase chromatography (10−>30% EtOAc/hexanes) yielded 35.37 g (55%) of diisopropyl (4S,5S)-2-[(1E)-prop-1-enyl]-1,3-dioxolane-4,5-dicarboxylate as an orange oil. 1H NMR ($CDCl_3$, 400 MHz) 6.03 (m, 1H); 5.86 (m, 2H); 5.12 (m, 2H); 4.71 (d, J=3.84 Hz, 1H); 4.63 (d, J=3.84 Hz, 1H); 1.78 (m, 3H); 1.30 (d, J=6.23 Hz, 12H); LC/MS [M+H]$^+$=287.

Step C. diisopropyl (4S,5S)-2-[(1S,2S)-2-methylcyclopropyl]-1,3-dioxolane-4,5-dicarboxylate To a −20° C. solution of intermediate diisopropyl (4S,5S)-2-[(1E)-prop-1-enyl]-1,3-dioxolane-4,5-dicarboxylate (4.10 g, 14.32 mmol) in 60 mL hexanes was added 1M diethylzinc in hexanes (42.96 mL, 42.96 mmol). Diiodomethane (6.92 mL, 85.92 mmol) was added dropwise with vigorous stirring. After 1 h at −20° C., the reaction was refrigerated at −5° C. After 17 h at −5° C., the reaction was stirred at 0° C. for an additional 5 h and then quenched with cold saturated ammonium chloride solution (100 mL) and extracted with $Et_2O$ (100 mL×3). The combined organics were washed w/aqueous sodium thiosulfate (100 mL) and brine (100 mL), filtered, dried over $Na_2SO_4$, filtered again and concentrated in vacuo. Purification by normal phase chromatography (10−>30% EtOAc/hexanes) yielded 3.85 g (89%) of diisopropyl (4S,5S)-2-[(1S,2S)-2-methylcyclopropyl]-1,3-dioxolane-4,5-dicarboxylate as a yellow oil. 1H NMR ($CDCl_3$, 400 MHz) 5.12 (m, 2H); 4.78 (d, J=6.41 Hz, 1H); 4.66 (d, J=4.21 Hz, 1H); 4.57 (d, J=4.22 Hz, 1H); 1.30 (m, 12H); 1.09 (d, J=5.68 Hz, 3H); 0.94 (m, 2H); 0.67 (m, 1H); 0.39 (m, 1H); LC/MS [M+H]$^+$=301.

Step D. 2-methyl-N-{(1E)-[(1S,2S)-2-methylcyclopropyl]methylidene}propane-2-sulfinamide To a solution of diisopropyl (4S,5S)-2-[(1S,2S)-2-methylcyclopropyl]-1,3-dioxolane-4,5-dicarboxylate (0.450 g, 1.50 mmol) in 5 mL CH$_2$Cl$_2$/200 uL H$_2$O was added p-toluenesulfonic acid (0.071 g, 0.38 mmol). Reaction heated to reflux at 50° C. After 16 h at 50° C., the reaction was cooled to rt. Water droplets sitting at the top of the reaction were removed. Copper (II) sulfate (0.507 g, 2.85 mmol) and R-(+)-tert-butanesulfinamide (0.173 g, 1.43 mmol) were added. After 5.5 h at ambient temperature, the reaction was filtered over a pad of celite. The celite was washed with CH$_2$Cl$_2$ (200 mL) and the filtrate concentrated in vacuo. Purification by normal phase chromatography (0->50% EtOAc/hexanes) yielded 0.245 g (92%) of 2-methyl-N-{(1E)-[(1S,2S)-2-methylcyclopropyl]methylidene}propane-2-sulfinamide as a clear, colorless residue. 1H NMR (CDCl$_3$, 400 MHz) 7.46 (d, J=7.69 Hz, 1H); 1.62 (m, 1H); 1.25 (m, 2H); 1.10 (m, 12H); 0.82 (m, 1H); LC/MS [M+H]$^+$=188.

Step E. 2-methyl-N-{(1S)-1-[(1S,2S)-2-methylcyclopropyl]ethyl}propane-2-sulfinamide To a −78° C. solution of 2-methyl-N-{(1E)-[(1S,2S)-2-methylcyclopropyl]methylidene}propane-2-sulfinamide (0.300 g, 1.60 mmol) in 5 mL CH$_2$Cl$_2$ was added 3M methylmagnesium bromide in Et$_2$O (1.07 mL, 3.20 mmol). After 2 h at −78° C., the reaction was warmed to rt. After 1 h at ambient temperature, the reaction was quenched with saturated ammonium chloride solution (15 mL) and extracted with EtOAc (30 mL×2). The combined organics were washed with brine (15 mL), dried over Na$_2$SO$_4$, filtered and concentrated in vacuo. Purification by normal phase chromatography (0->80% EtOAc/hexanes) yielded 0.224 g (69%) of -methyl-N-{(1S)-1-[(1S,2S)-2-methylcyclopropyl]ethyl}propane-2-sulfinamide as a clear, colorless residue. 1H NMR (CDCl$_3$, 400 MHz) 2.77 (m, 1H); 1.31 (d, J=6.50 Hz, 3H); 1.21 (s, 9H); 1.03 (d, J=5.77 Hz, 3H); 0.54 (m, 3H); 0.30 (m, 1H); LC/MS [M+H]$^+$=204.

Step F. (1S)-1-[(1S,2S)-2-methylcyclopropyl]ethanaminium chloride

To a 0° C. solution of 2-methyl-N-{(1S)-1-[(1S,2S)-2-methylcyclopropyl]ethyl}propane-2-sulfinamide (0.210 g, 1.03 mmol) in 4 mL MeOH was added 2M HCl in Et$_2$O (0.52 mL, 1.03 mmol). Reaction stirred from 0° C. to rt over 18 h and then concentrated in vacuo. The resulting material was taken up in Et$_2$O (4 mL) and concentrated in vacuo twice to give (1S)-1-[(1S,2S)-2-methylcyclopropyl]ethanaminium chloride as a white solid. 1H NMR (CDCl$_3$, 400 MHz) 2.60 (m, 1H); 1.37 (d, J=6.59 Hz, 3H); 1.08 (d, J=6.04 Hz, 3H); 0.77 (m, 1H); 0.64 (m, 2H); 0.42 (m, 1H); LC/MS [M+H]$^+$=100.

Intermediate XXX: [(1S,2S)-2-azido-1-benzyl-5,5,5-trifluorohexyl]amine

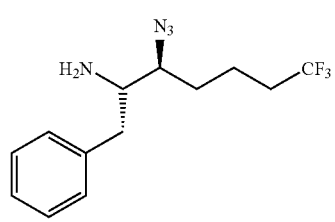

Prepared in a manner similar to intermediate I using freshly prepared Grignard reagent derived from 3,3,3-trifluorobutyliodide: ES MS (M+H)=287.1.

Intermediate A: 2-{[(2-methylcyclopropyl)methyl]amino}-6-[methyl(methylsulfonyl)amino]isonicotinic acid (Scheme 4)

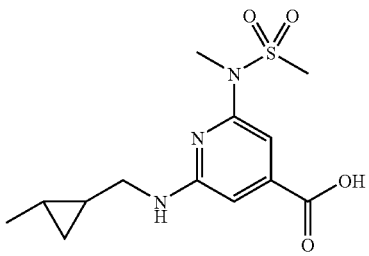

Step A: Sulfonamide Incorporation

Methyl 2,6-dichloroisonicotinate (5.0 g, 24.3 mmol), methyl (methylsulfonyl)amine (3.18 g, 29.12 mmol), potassium phosphate (7.22 g, 34.0 mmol), Xantphos (0.87 g, 1.50 mmol) and tris(dibenzylideneacetone)dipalladium (0.68 g, 0.51 mmol) were added to a dry, argon flushed flask. Dioxane (195 mL) was added, the solution degassed with argon and the reaction was heated to 100° C. for 16 hours. The reaction was cooled to rt, filtered through celite and evaporated in vacuo. Flash chromatography (silica, 0-50% EtOAc/CH$_2$Cl$_2$) gave methyl 2-chloro-6-[methyl(methylsulfonyl)amino]isonicotinate as a yellow oil: $^1$H NMR (400 MHz, CDCl$_3$) δ 7.88 (s, 1H), 7.68 (s, 1H), 3.96 (s, 3H), 3.44 (s, 3H), 3.11 (s, 3H).

Step B: Amination

A solution of methyl 2-chloro-6-[methyl(methylsulfonyl)amino]isonicotinate (1.2 g, 4.30 mmol), amine XI (1.0 g, 5.60 mmol), potassium phosphate (2.74 g, 12.9 mmol), and palladium bis(tri-t-butylphosphine) (0.11 g, 0.22 mmol) in degassed toluene (15 mL) was sealed in a glass tube and heated to 110° C. for 16 hours. The reaction was filtered through celite, rinsed with ethyl acetate and concentrated in vacuo. Flash chromatography (silica, 20% EtOAc/hexanes) gave methyl 2-{benzyl[(2-trans-methylcyclopropyl)methyl]amino}-6-[methyl(methylsulfonyl)amino]isonicotinate: $^1$H NMR (400 MHz, MeOD) δ 7.28 (m, 5H), 7.01 (d, J=0.8 Hz, 1H), 6.98 (d, J=0.8 Hz, 1H), 4.83 (s, 2H), 3.87 (s, 3H), 3.62 (dd, J=6.0, 14.8 Hz, 1H), 3.30 (dd, J=7.2, 14.8 Hz, 1H), 3.23 (s, 3H), 2.88 (s, 3H), 0.93 (d, J=6.0 Hz, 3H), 0.81 (m, 1H), 0.62 (m, 1H), 0.39 (m, 1H), 0.22 (m, 1H)

Step C: Hydrogenation

A solution of 2-{benzyl[(2-methylcyclopropyl)methyl]amino}-6-[methyl(methylsulfonyl)amino]isonicotinate (0.93 g, 2.23 mmol), 20% palladium hydroxide on carbon (0.042 g, 0.06 mmol) and trifluoroacetic acid (0.13 g, 1.11 mmol) in ethanol (10 mL) was placed under a hydrogen atmosphere and heated to 60° C. for 3 hours. The reaction was cooled to ambient emperature, filtered over celite, rinsed with methanol and evaporated in vacuo to give methyl 2-{[(2-trans-methylcyclopropyl)methyl]amino}-6-[methyl(methylsulfonyl)amino]isonicotinate: LCMS [M+H]=328.1

Step D: Saponification

A solution of methyl 2-{[(2-trans-methylcyclopropyl)methyl]amino}-6-[methyl(methylsulfonyl)amino]isonicotinate (0.8 g, 2.44 mmol) in methanol (5 mL) and tetrahydrofuran (5 mL) was treated with 1N NaOH (4.9 mL, 4.9 mmol) and the reaction was heated to 50° C. for 1 hour. The reaction was evaporated in vacuo and partitioned between 1M HCl and ethyl acetate. The combined organics were dried over sodium sulfate, filtered and evaporated in vacuo to give 2-{[(2-trans-methylcyclopropyl)methyl]amino}-6-[methyl(methylsulfonyl)amino]isonicotinic acid (A) as a white solid: $^1$H NMR (400 MHz, CD$_3$OD) δ 6.89 (s, 1H), 6.83 (s, 1H), 3.30 (s, 3H), 3.17 (d, J=6.8 Hz, 2H), 3.15 (s, 3H), 1.03 (d, J=6.0 Hz, 3H), 0.81 (m, 1H), 0.64 (m, 1H), 0.39 (m, 1H), 0.22 (m, 2H); HRMS (ES, M+H) calcd. for C$_{13}$H$_{19}$N$_3$O$_4$S: 314.1169, found: 314.1171.

Intermediate B: 2-[(cyclopropylmethyl)(propyl)amino]-6-[methyl(methylsulfonyl)amino]isonicotinic acid (Scheme 4)

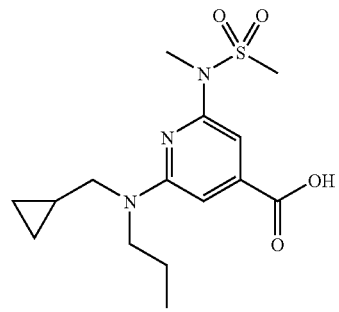

Prepared from methyl 2,6-dichloroisonicotinate using a procedure similar to that described for the preparation of Intermediate A: ES MS (M+H)=342.

Intermediate C: 2-[methyl(methylsulfonyl)amino]-6-(3-phenylpyrrolidin-1-yl)isonicotinic acid (Scheme 4)

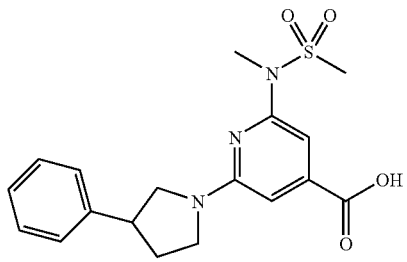

Prepared from methyl 2,6-dichloroisonicotinate using a procedure similar to that described for the preparation of Intermediate A: ES MS (M+H)=376.

Intermediate D: 2-{[2-(4-fluorophenyl)ethyl]amino}-6[methyl(methylsulfonyl)amino]isonicotinic acid (Scheme 4)

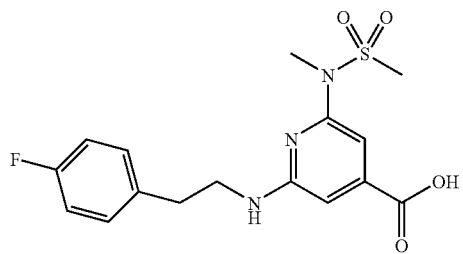

Prepared from methyl 2,6-dichloroisonicotinate using a procedure similar to that described for the preparation of Intermediate A: ES MS (M+H)=368.

Intermediate E: 3-({[(1R)-1-(4-fluorophenyl)ethyl]amino}carbonyl)-5-[methyl(methylsulfonyl)amino]benzoic acid (Scheme 5)

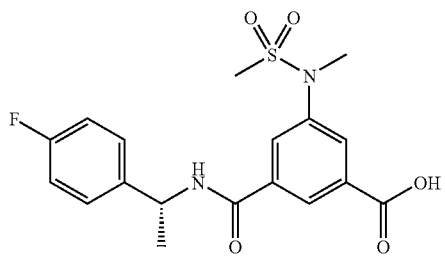

Step A: Sulfonylation

To a stirred slurry of dimethyl 5-aminoisophthalate (5.0 g, 23.90 mmol) in 100 mL CH$_2$Cl$_2$/pyridine (3:1) at 0° C. was added methanesulfonyl chloride (1.85 mL, 23.90 mmol). The resulting mixture was stirred for 4 h at room temperature. The solvent was removed in vacuo and ethylacetate (100 mL) was added resulting in precipitate formation. The product was collected by filtration to give the sulfonamide as a white solid. 1H NMR (400 MHz, DMSO-d6) δ 8.15 (s, 1H), 8.02 (s, 2H), 3.89 (s, 6H), 3.02 (s, 3H) LCMS [M−OCH3]+=256.16.

Step B: Methylation

To a solution of sodium hydride (0153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with H$_2$O (100 mL) and extracted with EtOAc (3×50 mL). The organic extracts were dried over MgSO$_4$ and evaporated to give the product. 1H NMR (400 MHz, DMSO-d6) δ 8.40 (s, 1H), 8.19 (s, 2H), 3.91 (s, 6H), 3.34 (s, 3H), 3.01 (s, 3H). LCMS [M+H]=302.15.

Step C: Hydrolysis

Diester (1.03 g, 3.38 mmol) from step B was dissolved in 50 mL THF:MeOH (1:1) and cooled to 1° C. 1N NaOH (3.38 mL, 3.38 mmol) was added and the reaction was allowed to warm to RT over 8 hours. The solution was acidified with 1N HCl (30 mL) and extracted with EtOAc (3×50 mL). The combined organic extracts were washed with brine and dried over MgSO$_4$, filtered and concentrated in vacuo. Purification on silica gel (5% MeOH/CHCl$_3$ containing 1% HOAc) gave the mono acid. 1H NMR (400 MHz, DMSO-d6) δ 8.30 (s, 1H), 8.10 (s, 2H), 3.84 (s, 3H), 3.27 (s, 3H), 2.94 (s, 3H). LCMS (M+H)=288.16.

Step D: Amine Coupling

A solution containing 6.99 g (24.1 mmol) of monoacid from step C in 50 mL DMF, EDC-HCl reagent (6.95 g, 36.2 mmol), (R)-1-(4-fluorophenyl)ethylamine (3.37 mL, 24.9 mmol), and 1-hydroxy-7-azabenzotriazole (3.28 g, 24.1 mmol) was stirred at ambient temperature for 1 h. The reaction was diluted with 125 mL EtOAc, washed with aq. 3M LiCl (2×75 mL), followed by 1N HCl (2×75 mL) and dried over Na$_2$SO$_4$. Upon solvent removal the product was obtained as a white solid (M+H)=409.5; 1H NMR (400 MHz, CDCl3) δ 8.26 (s, 1H), 8.17 (s, 1H), 8.05 (s, 1H), 7.37 (dd, J=5.3, 8.6 Hz, 2H), 7.05 (app. t, J=8.6 Hz, 2H) 6.40 (d, J=7.1 Hz, 1H), 5.33 (q, J=7.1 Hz, 1H), 3.96 (s, 3H), 3.37 (s, 3H), 2.88 (s, 3H), 1.64 (d, J=7.0 Hz, 3H).

Step E: Hydrolysis

To 9.32 g (22.8 mmol) of the benzyl amide from step D in 150 mL THF:MeOH (1:1) was added 3 N NaOH (22.8 mL, 68.4 mmol). The solution was heated to 50° C. for 1 h. After cooling the solution was concentrated to remove MeOH/THF under reduced pressure. The concentrated solution was acidified by the addition of 6 N HCl till pH 2-3 and extracted with EtOAc (2×100 mL). The combined organic extracts were washed with brine, dried over Na$_4$SO$_4$, filtered, and concentrated in vacuo the give the desired carboxylic acid as a white solid: 1H NMR (400 MHz, DMSO-d6) δ 9.11 (d, J=8.1, 1H), 8.41 (s, 1H), 8.09 (d, J=9.3 Hz, 2H), 7.44 (m, 2H), 7.16 (t, J=8.8 Hz, 2H), 5.20 (t, J=5, 1H), 3.32 (s, 3H) 3.00 (s, 3H), 1.50 (d, J=7.1 Hz, 3H); LCMS (M+H)=395.0.

Intermediate F: 5-{[Butyl(methyl)amino]carbonyl}-2'-cyano-1,1'-biphenyl-3-carboxylic acid (Scheme 5)

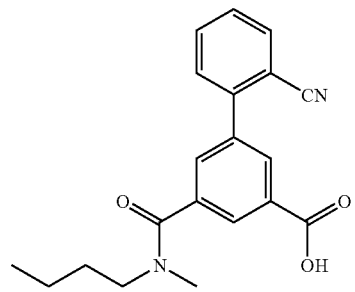

Step A and B: Cross-coupling and Saponification.

To a solution of dimethyl 5-iodoisophthalate (13 g, 40.6 mmol) in 100 mL THF was added 2-cyano-phenyl zinc bromide (97.5 mL, 48.7 mmol, 0.5 M THF) and tetrakis(triphenylphosphine) palladium (214 mg, 0.2 mmol) and the reaction mixture was stirred at room temperature for 2 h. The precipitated solid was filtered, the filtrate was diluted with MeOH to provide after filtration a second crop for a total of 10.1 g of dimethyl 5-(2-cyanophenyl)isophthalate which was hydrolyzed to the corresponding monoacid 2'-cyano-5-(methoxycarbonyl)-1,1'-biphenyl-3-carboxylic acid following a similar procedure as described in intermediate B preparation, step C: $^1$H NMR (400 MHz, d$_6$-DMSO) δ 13.55 (br s, 1H), 8.60-8.55 (m, 1H), 8.38-8.31 (m, 2H), 8.02 (d, J=8.3 Hz, 1H), 7.85 (td, J=8.3 Hz, 1.5 Hz 1H), 7.75 (d, J=8.3 Hz, 1H), 7.66 (td, J=8.3 Hz, 1.5 Hz 1H), 3.93 (s, 3H).

Step C: Amide Coupling.

In a 500 mL flask containing 2'-cyano-5-(methoxycarbonyl)-1,1'-biphenyl-3-carboxylic acid (3.0 g, 10.6 mmol) from step B, N-methyl-butylamine (1.39 g, 16.0 mmol), HOAt (1.45 g, 10.6 mamol) in CH$_2$Cl$_2$ was added EDC-HCl (3.06 g, 16.0 mmol) at rt. After stirring overnight the reaction was poured onto 0.1 N HCl, extracted with CH$_2$Cl$_2$ (3×75 mL) and the combined extracts washed with brine, dried over Na$_2$SO$_4$ and concentrated in vacuo. Purification by flash chromatography (30-40% ethyl acetate/hexanes) gave methyl 5-{[butyl(methyl)amino]carbonyl}-2'-cyano-1,1'-biphenyl-3-carboxylate as an oil: amide rotamers present at rt, $^1$H NMR (400 MHz, CDCl$_3$) δ 8.20 (s, 1H), 8.14 (d, J=4.0 Hz, 1H), 7.76 (m, 2H), 7.66 (t, J=8.0 Hz, 1H), 7.50 (m, 2H), 3.93 (s, 3H), 3.54 (t, J=7.6 Hz, 1H), 3.32 (t, J=7.2 Hz, 1H), 3.08 (s, 1.5H), 3.00 (s, 1.5H), 1.65 (quint, J=6.8 Hz, 1H), 1.53 (quint, J=7.2 Hz, 1H), 1.40 (sext, J=7.2 Hz, 1H), 1.17 (sext, J=7.2 Hz, 1H), 0.96 (t, J=7.2 Hz, 1.5H), 0.79 (t, J=7.2 Hz, 1.5H)

Step D: Hydrolysis.

Prepared using a procedure similar to Intermediate B, step E, Methyl 5-{[butyl(methyl)amino]carbonyl}-2'-cyano-1,1'-biphenyl-3-carboxylate (3.4 g, 9.7 mmol) from step C above was hydrolyzed to give 5-{[butyl(methyl)amino]carbonyl}-2'-cyano-1,1'-biphenyl-3-carboxylic acid: amide rotamers present at rt, $^1$H NMR (400 MHz, CDCl$_3$) δ 8.26 (s, 1H), 8.21 (d, J=5.2 Hz, 1H), 7.81 (t, J=1.6 Hz, 1H), 7.78 (d, J=8.0 Hz, 1H), 7.67 (t, J=6.4 Hz, 1H), 7.54-7.47 (m, 2H), 3.57 (t, J=7.2 Hz, 1H), 3.34 (t, J=7.2 Hz, 1H), 3.12 (s, 1.5H), 3.04 (s, 1.5H), 1.70 (quint, J=6.4 Hz, 1H), 1.56 (quint, J=6.0 Hz, 1H), 1.42 (sext, J=7.2 Hz, 1H), 1.90 (sext, J=7.2 Hz, 1H), 0.98 (t, J=7.2 Hz, 1.5H), 0.80 (t, J=7.2 Hz, 1.5H); LCMS (M+H)=337.3

Intermediate G: 2'-cyano-5-({[(1R)-1-(4-fluorophenyl)ethyl]amino}carbonyl)-1,1'-biphenyl-3-carboxylic acid (Scheme 5)

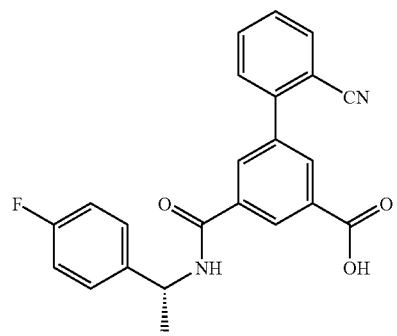

Prepared from methyl dimethyl 5-iodoisophthalate using a procedure similar to that described for the preparation of Intermediate F: ES MS (M+H)=389.

Intermediate H: 3-[(2-Methylcyclopropyl)methoxy]-5-[methyl(methylsulfonyl)amino]benzoic acid (Scheme 6)

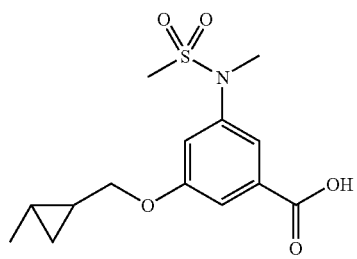

Step A. To a stirred solution of dimethyl 5-hydroxyisophthalate (8.6 g, 41.1 mmol) in 200 mL of acetone was added K$_2$CO$_3$ (5.7 g, 41.1 mmol) and trans-crotyl bromide (5.5 g, 41.1 mmol). The resulting mixture was stirred at reflux for 16 h. The solids were removed by filtration and the filtrate was evaporated to near dryness. The resulting residue was dissolved in 200 mL of ether and washed 3×20 mL of 1N HCl then brine. The organic extracts were dried over MgSO$_4$ and evaporated to give aryl ether A. $^1$H NMR (CDCl$_3$) δ 8.25 (s, 1H), 7.75 (s, 2H), 5.93 (m, 1H), 5.77 (m, 1H), 4.58 (d, J=2.2 Hz, 2H), 3.91 (s, 6H), 1.81 (d, J=2.2 Hz, 3H). LCMS (M+H)=265.24.

Step B. A 0° C. solution containing 9.4 g (35.6 mmol) of the isophthalate from step A in 300 mL of a 1:1 mixture of THF and MeOH was treated with 35.6 mL (35.6 mmol) of 1N NaOH. The ice bath was allowed to stir to ambient temperature over 16 h. The reaction mixture was concentrated to ca. 1/8 volume before it was acidified with 25 mL of 3N HCl. The solids that precipitated were redissolved in 300 mL of EtOAc and washed with brine (2×25 mL). The organic extract was dried over MgSO$_4$ and evaporated to give the desired carboxylic acid. $^1$H NMR (CDCl3) δ 8.37 (s, 1H), 7.82 (s, 2H), 5.93 (m, 1H), 5.77 (m, 1H), 4.58 (d, J=2.2 Hz, 2H), 3.95 (s, 3H), 1.77 (d, J=2.2 Hz, 3H). LCMS (M+H)=252.18.

Step C. To a 0° C. solution containing 4.0 g (16.0 mmol) of carboxylic acid from step B above in 80 mL of THF was added 4.2 mL (30.2 mmol) of Et$_3$N and 2.2 mL (22.7 mmol) of ethyl chloroformate. The resulting slurry was stirred for 1 h and treated with 2.46 g (37.8 mmol) of NaN$_3$ dissolved in 15 mL of water. After an additional hour at rt the reaction mixture was diluted with 50 mL of water and washed with toluene (3×50 mL). The combined organic extracts were dried over MgSO$_4$ and refluxed over 16 h. The reaction was cooled to rt and treated with 3.1 mL (30.2 mmol) of benzyl alcohol and 4.2 mL (30.2 mL) of triethylamine. The reaction was refluxed for 24 h, cooled and diluted with 100 mL of EtOAc and 35 mL of 10% citric acid. The organic extract was washed with water and brine then dried over MgSO$_4$. Column chromatography (2:3 EtOAc/Hexanes) afforded the carbamate C. $^1$H NMR (CDCl$_3$) δ 7.38 (m, 8H), 6.85 (bs, 1H), 5.85 (m, 1H), 5.65 (m, 1H), 5.20 (s, 2H), 4.44 (d, J=6.0 Hz, 2H), 3.82 (s, 3H), 1.71 (d, 3H). LCMS (M+H)=356.25.

Step D. A solution of 3.56 g (10.0 mmol) of the aryl ether from step C was dissolved in 100 mL of EtOAc and treated with 50 mL (c.a. 0.5 M, 25 mmol) of freshly prepared CH$_2$N$_2$. After stirring for 5 minutes, 112 mg (0.5 mmol) of Pd(OAc)$_2$ was added to effect vigorous release of N$_2$. After an additional 30 minutes, the brown slurry was evaporated and chromatographed (1:1 EtOAc/Hexanes) to give the desired cyclopropylmethyl ether. $^1$H NMR (CDCl$_3$) δ 7.55 (s, 1H), 7.44 (m, 7H), 6.80 (bs, 1H), 5.23 (s, 2H), 3.85 (s, 3H), 3.80 (m, 2H), 1.04 (d, 3H), 0.94 (m, 1H), 0.75 (m, 1H), 0.47 (m, 1H), 0.38 (m, 1H). LCMS (M+H)=368.26.

Step E. To a solution of the benzyl carbamate (3.6 g, 10.0 mmol) from step D and 1.5 g of 10% Pd/C in EtOAc (100 mL) was stirred at room temperature under a balloon of hydrogen gas for 5 h. The mixture was filtered through a pad of Celite, concentrated, and purified on silica gel (50% EtOAc/Hexanes) to afford the desired aniline. $^1$H NMR (CDCl$_3$) δ 6.99 (s, 2H), 6.40 (s, 1H), 3.85 (s, 3H), 3.75 (m, 2H), 1.77 (m, 1H), 1.45 (m, 1H), 1.04 (d, 3H), 0.47 (m, 1H), 0.33 (m, 1H). LCMS (M+H)=236.2.

Step F. To a 0° C. solution of the aniline from step E (940 mg, 4.0 mmol) in 30 mL of CH$_2$Cl$_2$ and 5 mL of pyridine was added methanesulfonyl chloride (0.40 mL, 4.0 mmol). The resulting mixture was stirred at this temperature for 2 h before being diluted with 100 mL of DCM. The solution was washed with 1N HCl (3×25 mL), water (2×25 mL), and brine (25 mL). The organic phase was dried and concentrated to provide sulfonamide F that was used in the next step without further purification. LCMS (M+H)=314.1.

Step G. The sulfonamide from step F (1.25 g, 4.0 mmol) in DMF (20 mL) was treated with 95% sodium hydride (106 mg, 4.4 mmol) and excess methyl iodide (3 mL). The resulting mixture was stirred at ambient temperature for 1 h and was diluted with 200 mL of ether. The solution was washed with water (7×25 mL) and brine then dried over MgSO$_4$. Purification by silica gel chromatography (2:3 EtOAc/Hexanes) afforded the desired methylated sulfonamide. $^1$H NMR (CDCl$_3$ w/0.05% DMSO-d6) δ 7.65 (s, 1H), 7.41 (s, 1H), 7.15 (s, 1H), 3.93 (s, 3H), 3.80 (t, 2H), 3.30 (S, 3H), 2.87 (s, 3H), 1.11 (d, 3H), 0.88 (m, 1H), 0.55 (m, 1H), 0.37 (m, 1H). LCMS (M+H)=328.23.

Step H. To a stirred solution of the ester from step G (625 mg, 2.0 mmol) in 12 mL THF/MeOH (1:1) was added 15% NaOH (2.2 mL, 8.0 mmol). After the reaction mixture was stirred at 45° C. for 2 h the solvents were evaporated and the residue was acidified with 3N HCl (4.0 mL, 12 mmol). The solid was taken up in 75 mL of DCM and the organic phase was washed with brine. The organic phase was dried and evaporated to yield the desired carboxylic acid 3-[(2-methylcyclopropyl)methoxy]-5-[methyl(methylsulfonyl)amino]benzoic acid as a white solid. $^1$H NMR (CDCl$_3$ w/0.05% DMSO-d$_6$) δ 7.61 (s, 1H), 7.44 (s, 1H), 7.15 (s, 1H), 3.83 (t, 2H), 3.32 (S, 3H), 2.83 (s, 3H), 1.11 (d, 3H), 0.88 (m, 1H), 0.55 (m, 1H), 0.37 (m, 1H). LCMS (M+H)=314.22.

EXAMPLE 1

N-[(1S,2S)-2-amino-1-benzylhexyl]-2-{[(2-methylcyclopropyl)methyl]amino}-6-[methyl(methylsulfonyl)amino]isonicotinamide (Scheme 8)

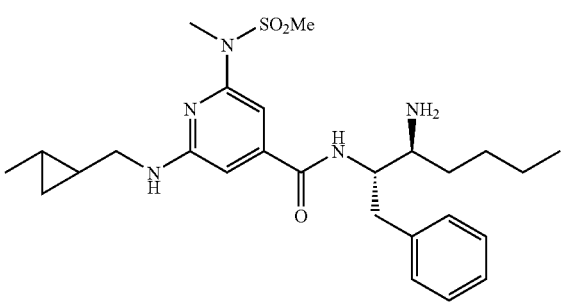

Step A: Amide Formation

A solution of acid intermediate A (35 mg, 0.112 mmol), amine intermediate I (28 mg, 0.134 mmol), N,N-diisopropylethylamine (36 mg, 0.28 mmol), and HOAT (15 mg, 0.112 mmol) in methylene chloride (1.5 mL) was treated with EDC (32 mg, 0.168 mmol). After stirring 2 hours at ambient temperature the solution was partitioned between water/methylene chloride. The organics were washed with 1N HCl followed by brine. The combined organics were dried over sodium sulfate, filtered and evaporated in vacuo to give N-[(1S,2S)-2-azido-1-benzylhexyl]-2-{[(2-methylcyclopropyl)methyl]amino}-6-[methyl(methylsulfonyl)amino]isonicotinamide as a crude oil. LCMS (M+H)=528.0

Step B: Azide Reduction

A solution of crude N-[(1S,2S)-2-azido-1-benzylhexyl]-2-{[(2-methylcyclopropyl)methyl]amino}-6-[methyl(methylsulfonyl)amino]isonicotinamide in methanol (2 mL) and 10% palladium on carbon (12 mg) in degassed methanol was placed under a hydrogen atmosphere for 1 hour. The reaction was filtered through celite, rinsed with methanol and evaporated in vacuo. Purification by reverse phase LC gave N-[(1S, 2S)-2-amino-1-benzylhexyl]-2-{[(2-methylcyclopropyl)methyl]amino}-6-[methyl(methylsulfonyl)amino] isonicotinamide. $^1$H NMR (CD$_3$OD) δ 7.28 (m, 5H), 6.55 (s, 1H), 6.44 (s, 1H), 4.35 (m, 1H), 3.42 (m, 1H), 3.29 (s, 3H), 3.16 (m, 5H), 3.00 (m, 2H), 1.85 (m, 1H), 1.72 (m, 1H), 1.43 (m, 4H), 1.05 (d, J=5.96 Hz, 3H), 0.98 (t, J=7.14 Hz, 3H), 0.80 (m, 1H), 0.65 (m, 1H), 0.41 (m, 1H), 0.24 (m, 1H) LCMS [M+H]$^+$=314.1.

The following examples were prepared in an analogous manner to that described in Example 1 using various combinations of Intermediates I-XXX or related derivatives thereof and Intermediate acids of types A-H or related derivatives thereof.

| Example | Structure | Schemes & Intermediates | ES MS M + H |
|---|---|---|---|
| 2 | 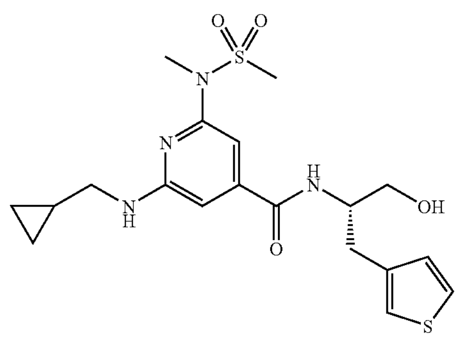 | Schemes 4, 8 | 439 |
| 3 | 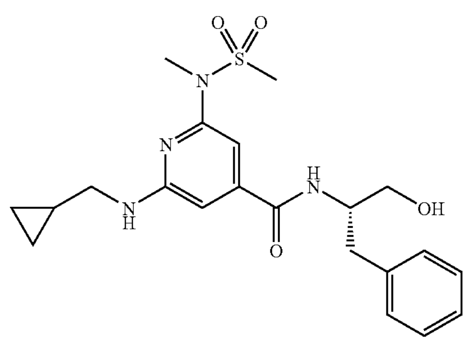 | Schemes 4, 8 | 433 |
| 4 | 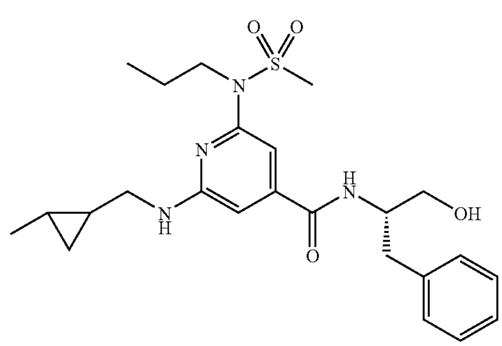 | Schemes 4, 8 | 475 |

-continued

| Example | Structure | Schemes & Intermediates | ES MS M + H |
|---|---|---|---|
| 5 | 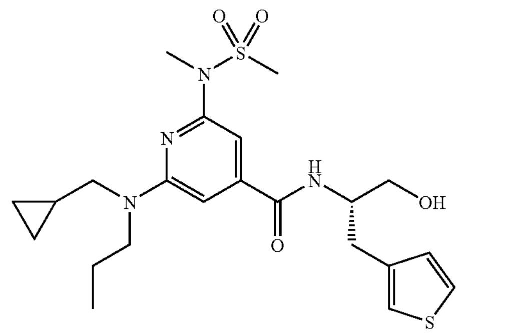 | Schemes 2, 4, 8 | 481 |
| 6 | 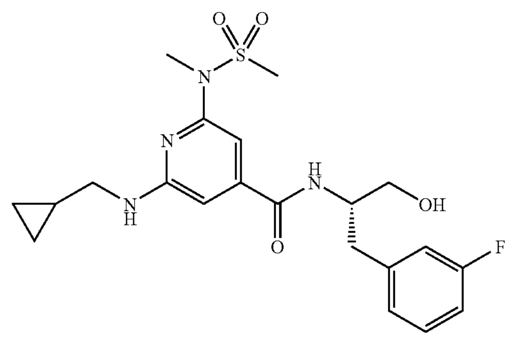 | Schemes 4, 8 | 451 |
| 7 | 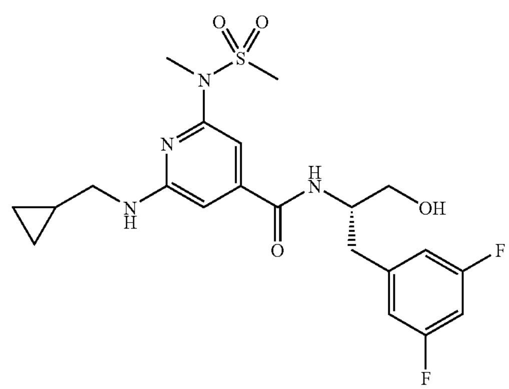 | Schemes 4, 8 | 488 |
| 8 | 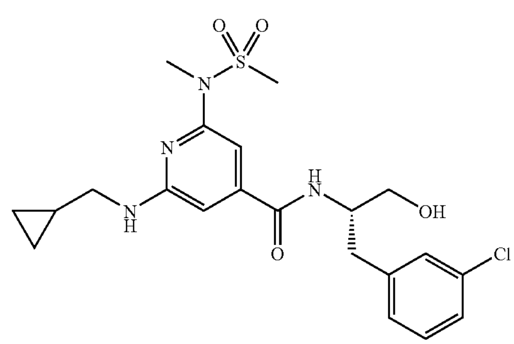 | Schemes 4, 8 | 467 |

| Example | Structure | Schemes & Intermediates | ES MS M + H |
|---|---|---|---|
| 9 | 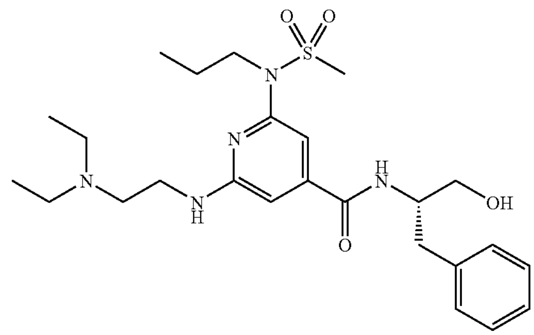 | Schemes 4, 8 | 506 |
| 10 | 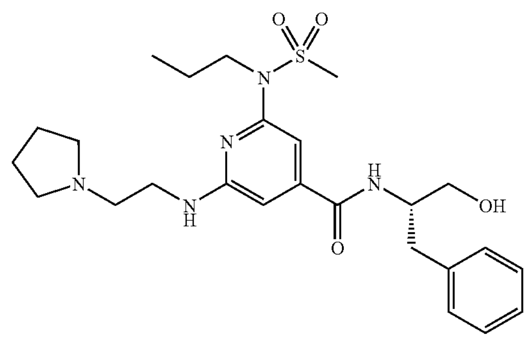 | Schemes 4, 8 | 504 |
| 11 | 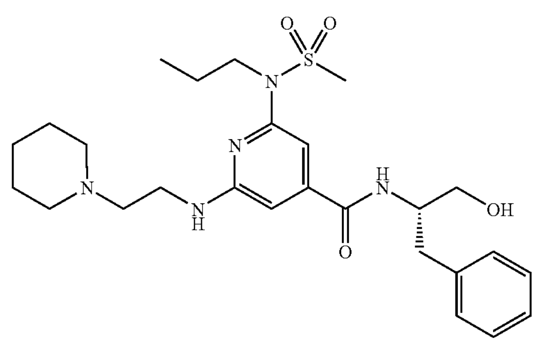 | Schemes 4, 8 | 518 |
| 12 | 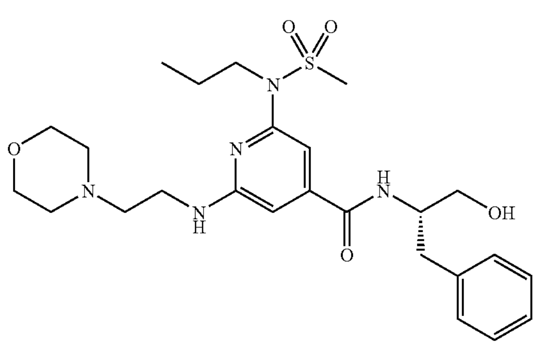 | Schemes 4, 8 | 520 |

-continued

| Example | Structure | Schemes & Intermediates | ES MS M + H |
|---|---|---|---|
| 13 | 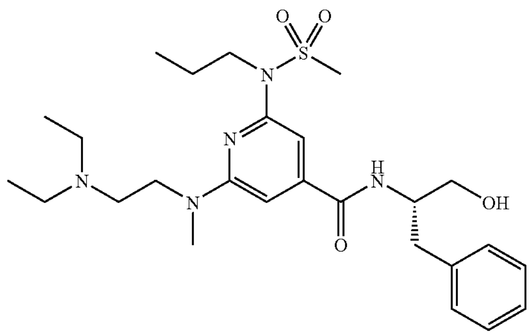 | Schemes 4, 8 | 520 |
| 14 | 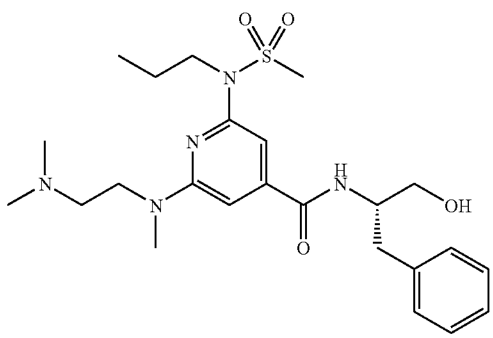 | Schemes 4, 8 | 492 |
| 15 | 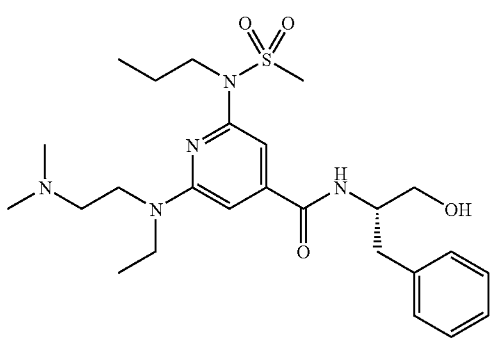 | Schemes 4, 8 | 506 |
| 16 | 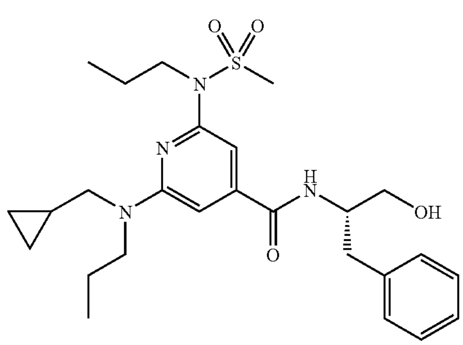 | Schemes 2, 4, 8 | 503 |

-continued

| Example | Structure | Schemes & Intermediates | ES MS M + H |
|---|---|---|---|
| 17 | 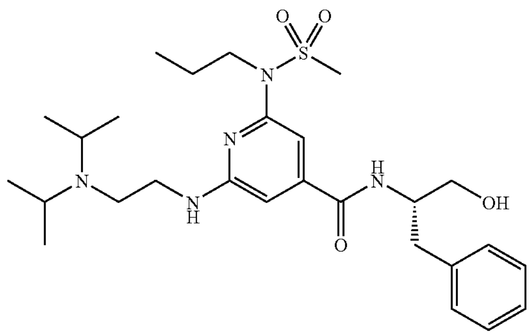 | Schemes 4, 8 | 534 |
| 18 | 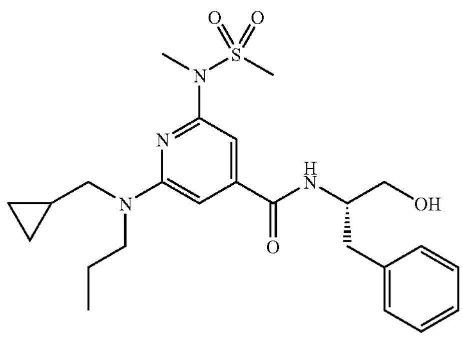 | Schemes 2, 4, 8 | 475 |
| 19 | 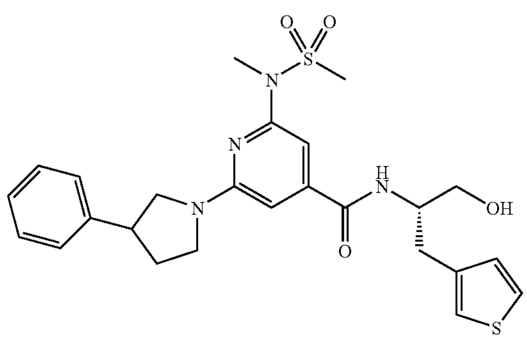 | Schemes 4, 8 Intermediate C | 515 |
| 20 | 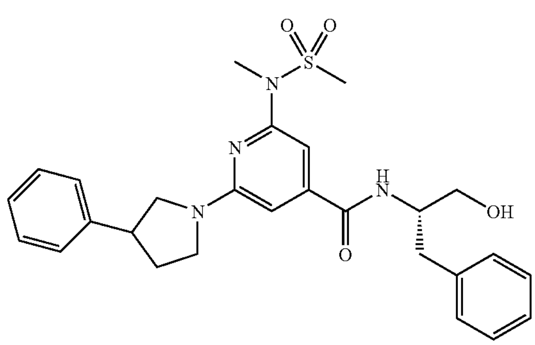 | Schemes 4, 8 Intermediate C | 509 |

-continued

| Example | Structure | Schemes & Intermediates | ES MS M + H |
|---|---|---|---|
| 21 | 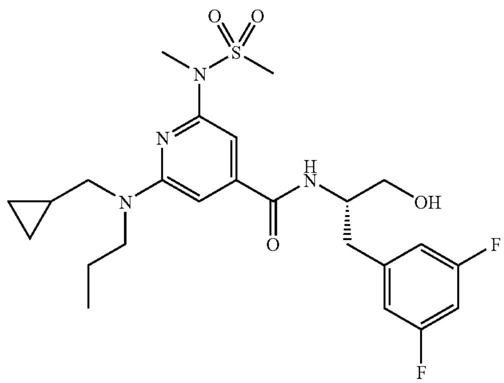 | Schemes 2, 4, 8 | 511 |
| 22 | 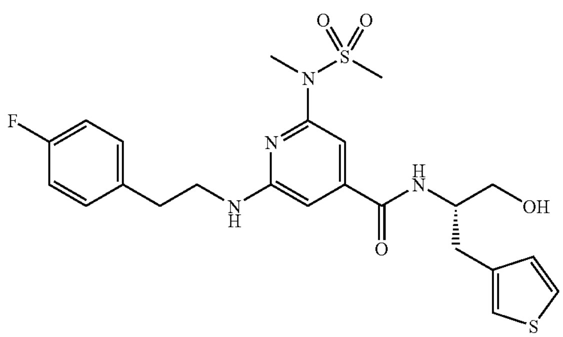 | Schemes 4, 8 Intermediate D | 507 |
| 23 | 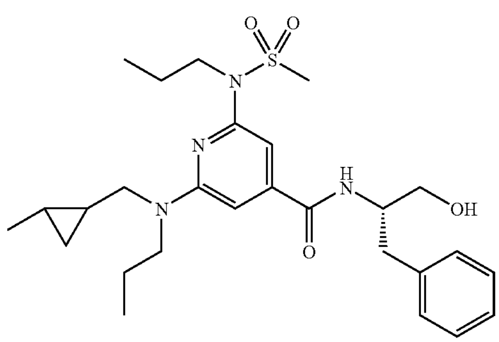 | Schemes 2, 4, 8 | 517 |
| 24 | 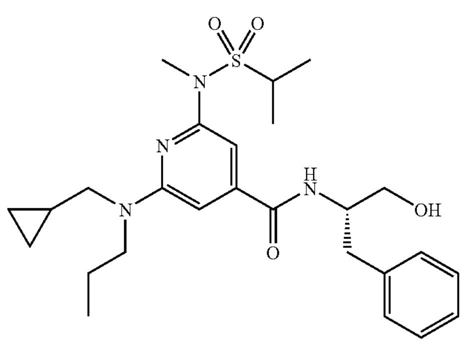 | Schemes 2, 4, 8 | 503 |

| Example | Structure | Schemes & Intermediates | ES MS M + H |
|---------|-----------|-------------------------|-------------|
| 25 | 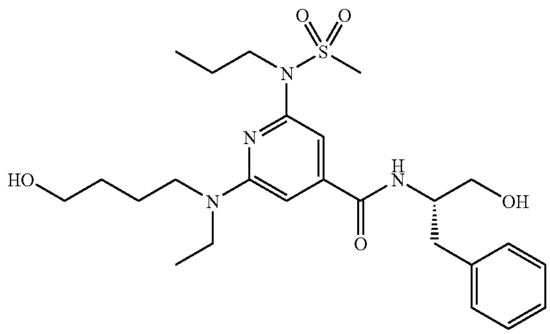 | Schemes 4, 8 | 507 |
| 26 | 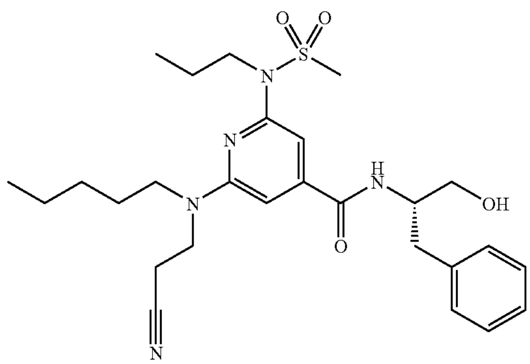 | Schemes 4, 8 | 530 |
| 27 | 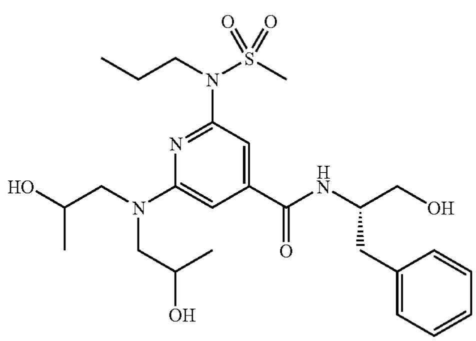 | Schemes 4, 8 | 523 |
| 28 | 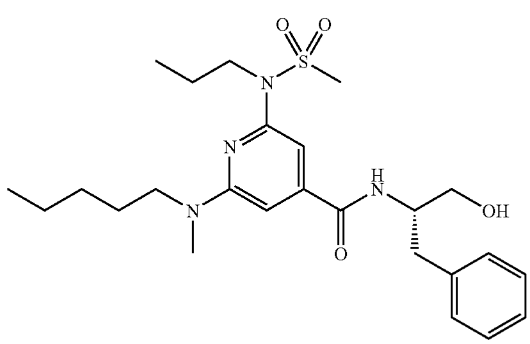 | Schemes 4, 8 | 491 |

| Example | Structure | Schemes & Intermediates | ES MS M + H |
|---|---|---|---|
| 29 | 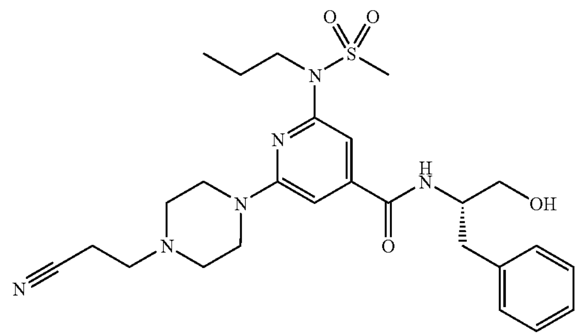 | Schemes 4, 8 | 529 |
| 30 | 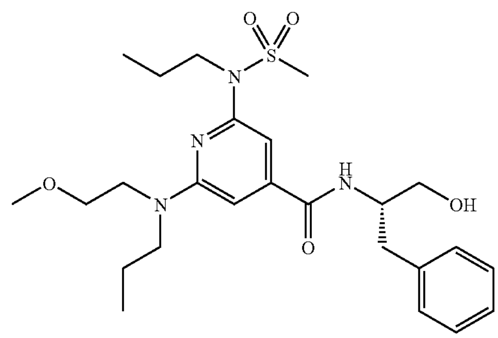 | Schemes 4, 8 | 507 |
| 31 | 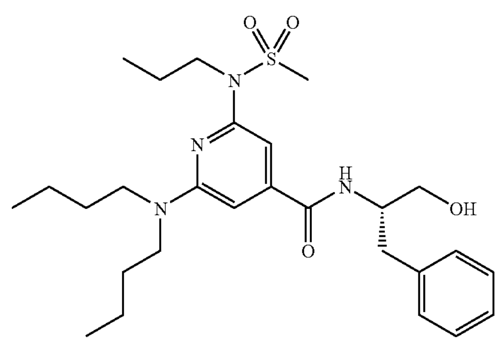 | Schemes 4, 8 | 519 |
| 32 | 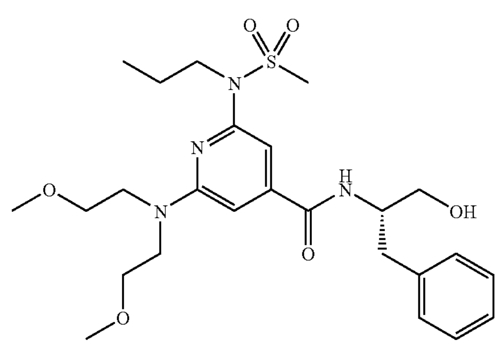 | Schemes 4, 8 | 523 |

| Example | Structure | Schemes & Intermediates | ES MS M + H |
|---|---|---|---|
| 33 | 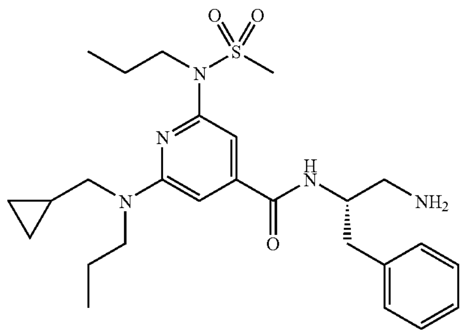 | Schemes 4, 8 | 502 |
| 34 | 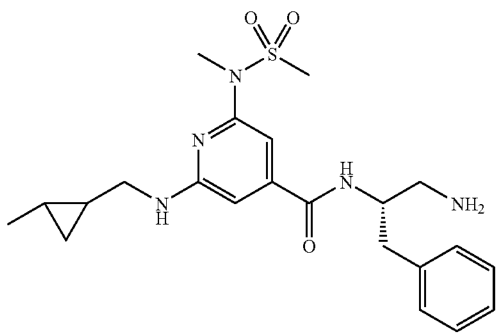 | Schemes 3, 4, 8 Intermediate A | 446 |
| 35 | 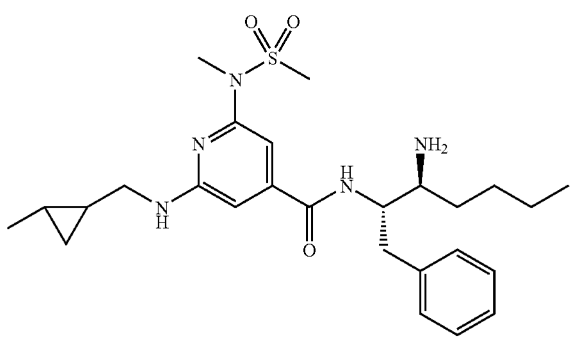 | Schemes 1, 3, 4, 8 Intermediates A, I | 502 |
| 36 | 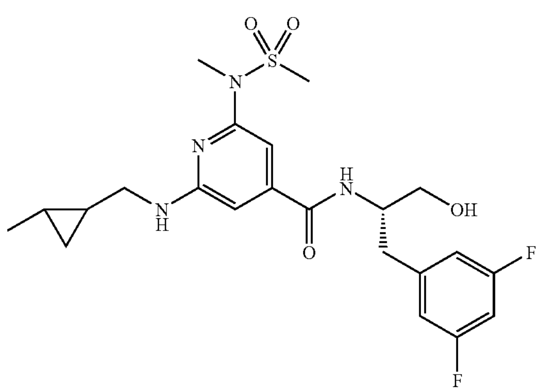 | Schemes 3, 4, 8 Intermediate A | 483 |

-continued

| Example | Structure | Schemes & Intermediates | ES MS M + H |
|---|---|---|---|
| 37 | 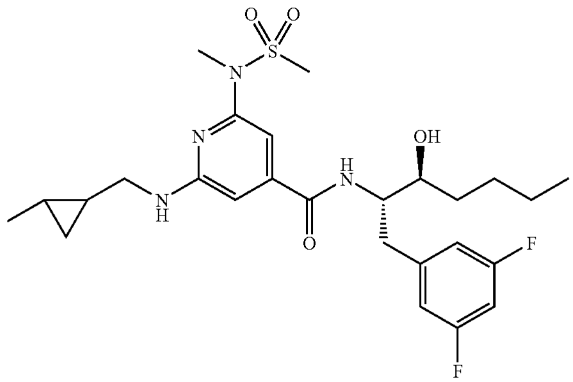 | Schemes 1, 3, 4, 8<br>Intermediates A, IX | 539 |
| 38 | 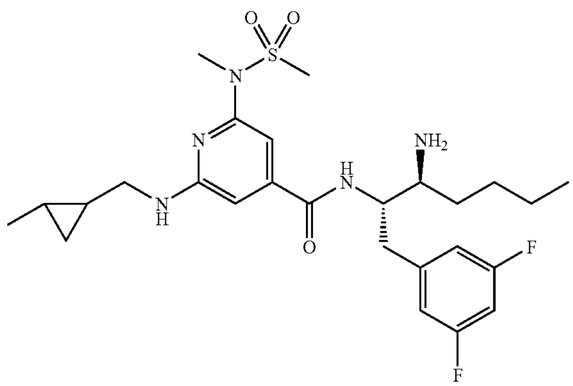 | Schemes 1, 3, 4, 8<br>Intermediates A, VIII | 538 |
| 39 | 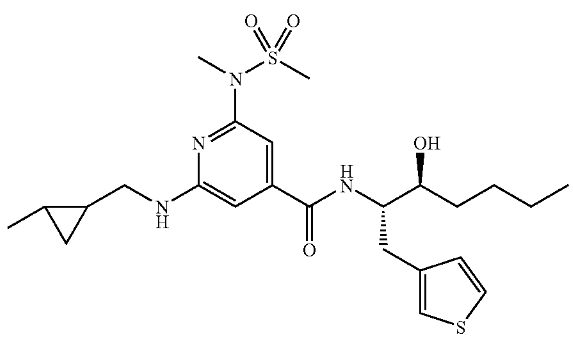 | Schemes 1, 3, 4, 8<br>Intermediates A, VI | 509 |
| 40 | 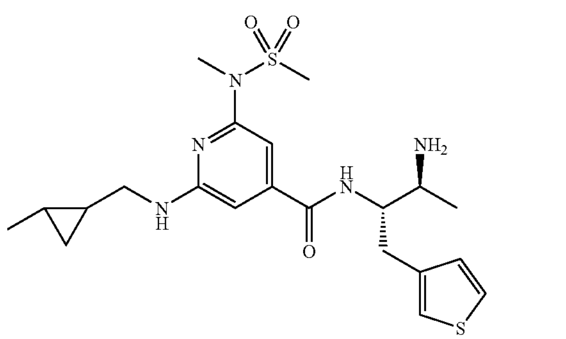 | Schemes 1, 3, 4, 8<br>Intermediates A, VI | 466 |

-continued

| Example | Structure | Schemes & Intermediates | ES MS M + H |
|---|---|---|---|
| 41 | 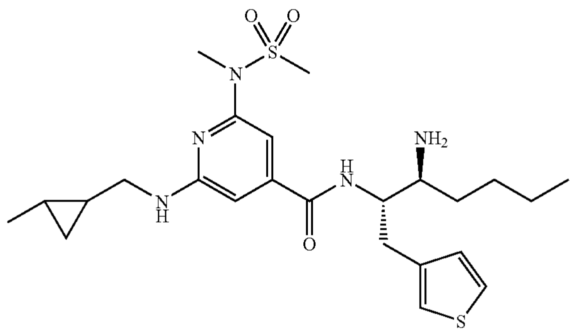 | Schemes 1, 3, 4, 8<br>Intermediates A, V | 508 |
| 42 | 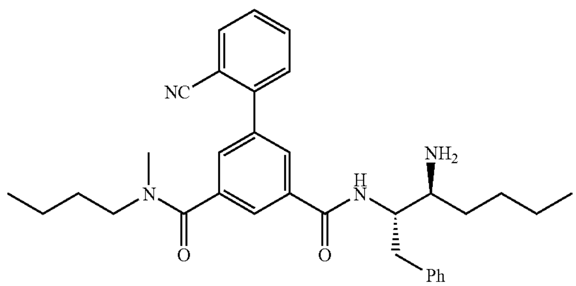 | Schemes 1, 5, 8<br>Intermediates F, I | 525 |
| 43 | 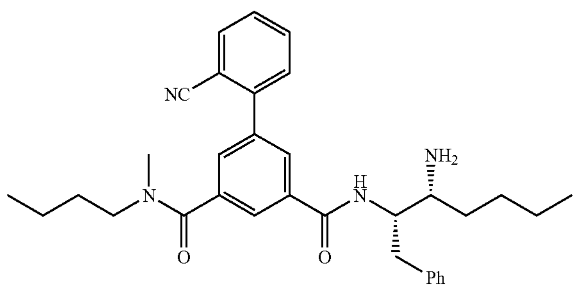 | Schemes 1, 5, 8<br>Intermediates F, II | 525 |
| 44 | 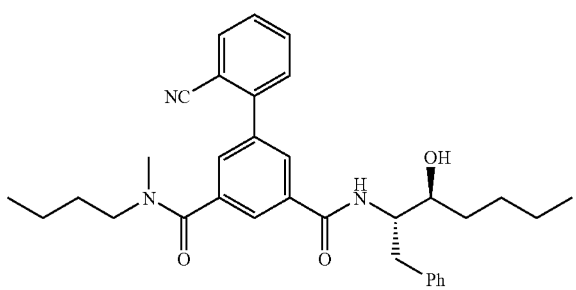 | Schemes 1, 5, 8<br>Intermediates F, III | 526 |
| 45 | 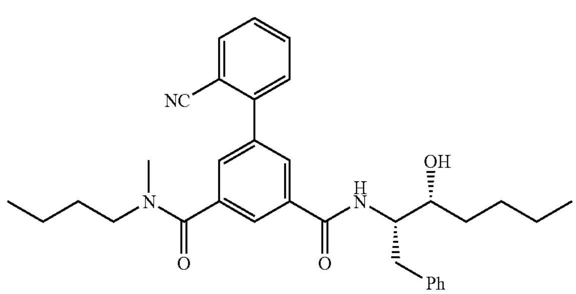 | Schemes 1, 5, 8<br>Intermediates F, IV | 526 |

-continued

| Example | Structure | Schemes & Intermediates | ES MS M + H |
|---|---|---|---|
| 46 | 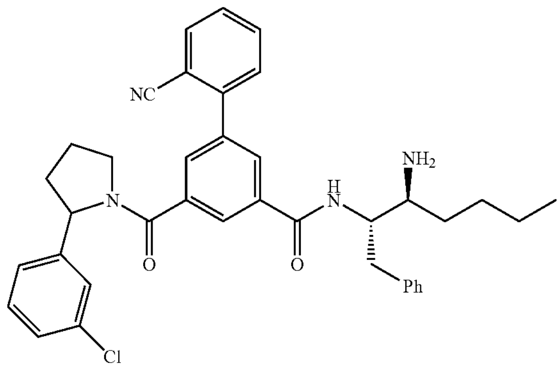 | Schemes 1, 5, 8 Intermediate I | 619 |
| 47 | 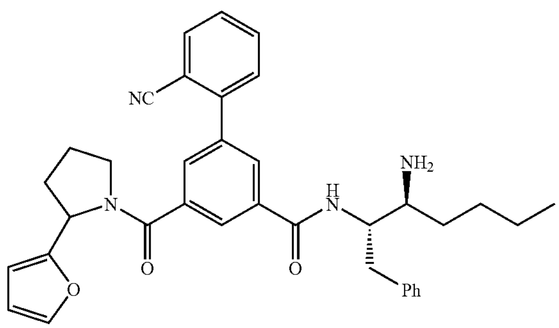 | Schemes 1, 5, 8 Intermediate I | 575 |
| 48 | 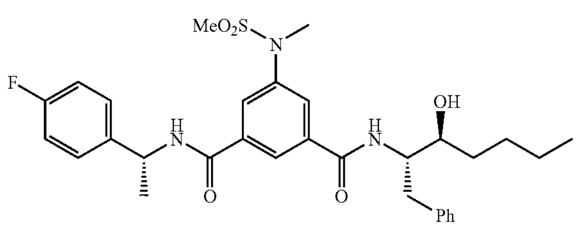 | Schemes 1, 5, 8 Intermediate E, III | 584 |
| 49 | 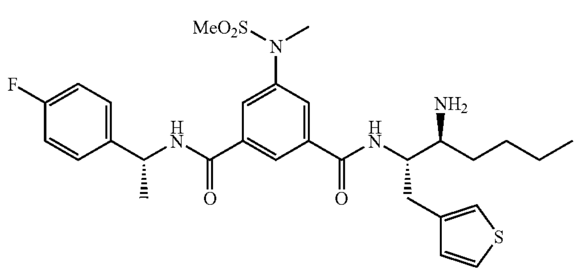 | Schemes 1, 5, 8 Intermediates E, V | 589 |
| 50 | 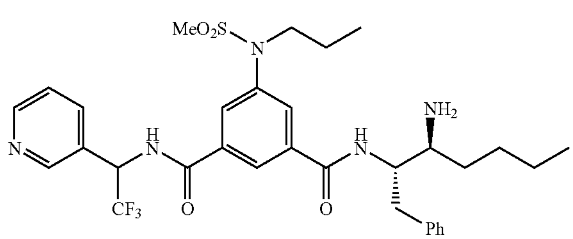 | Schemes 1, 5, 8 Intermediates I | 648 |

-continued

| Example | Structure | Schemes & Intermediates | ES MS M + H |
|---|---|---|---|
| 51 | 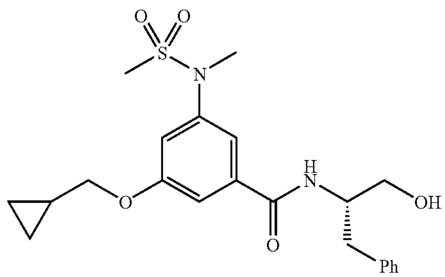 | Schemes 6, 8 | 433 |
| 52 | 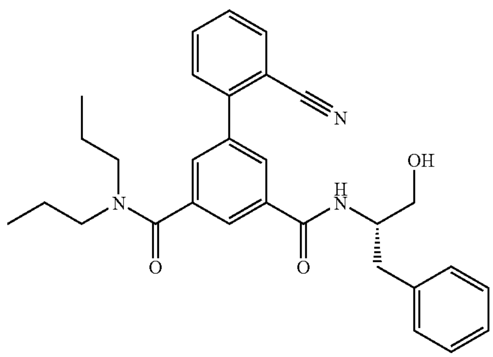 | Schemes 5, 8 | 484 |
| 53 | 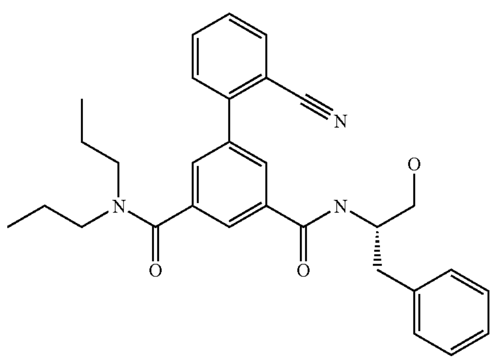 | Schemes 5, 8 | 445 |
| 54 | 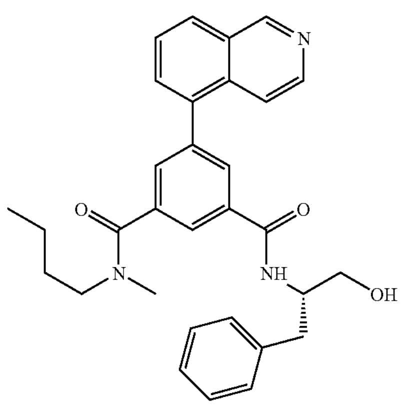 | Scheme 5 | 496 |

| Example | Structure | Schemes & Intermediates | ES MS M + H |
|---------|-----------|-------------------------|-------------|
| 55 | 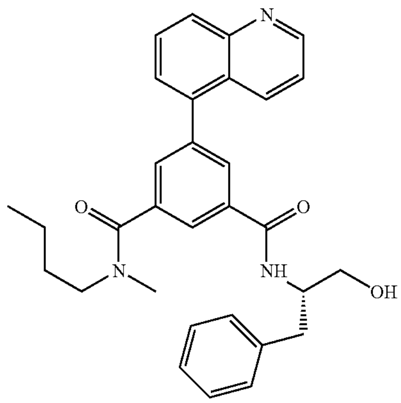 | Scheme 5 | 496 |
| 56 | 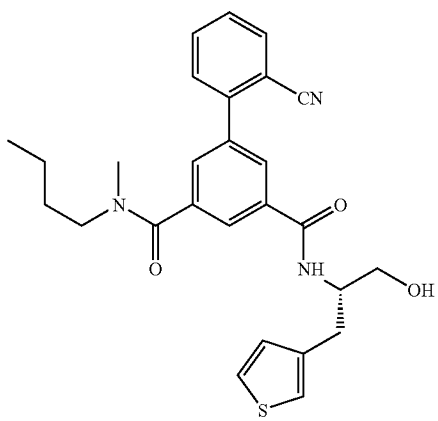 | Schemes 5, 8 Intermediate F | 476 |
| 57 | 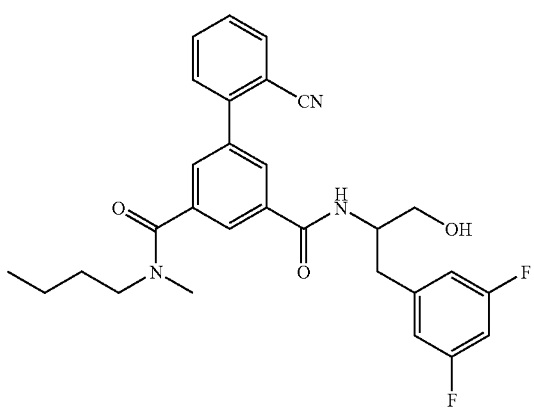 | Schemes 5, 8 Intermediate F | 506 |

-continued

| Example | Structure | Schemes & Intermediates | ES MS M + H |
|---|---|---|---|
| 58 | 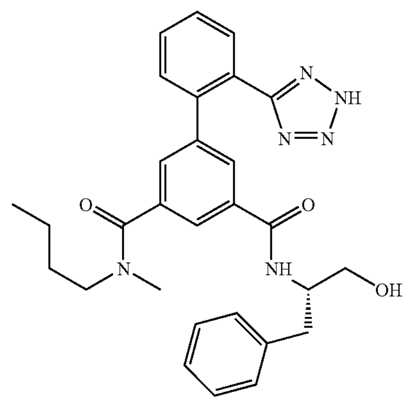 | Scheme 5 | 513 |
| 59 | 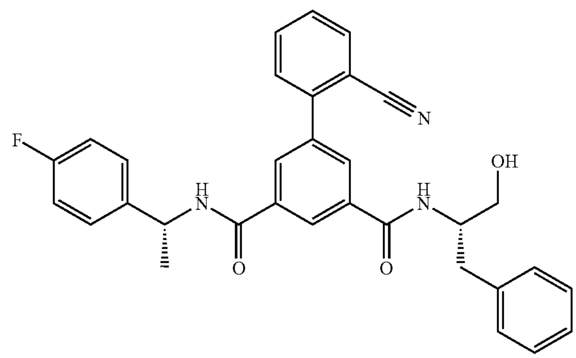 | Schemes 5, 8 Intermediate G | 522 |
| 60 | 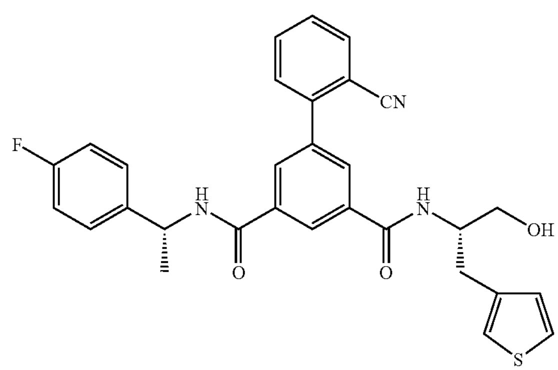 | Schemes 5, 8 Intermediate G | 528 |
| 61 | 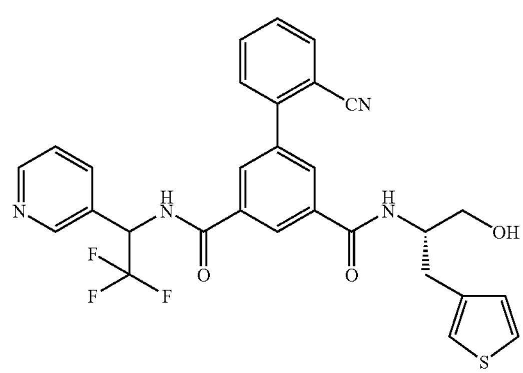 | Schemes 5, 8 | 565 |

-continued

| Example | Structure | Schemes & Intermediates | ES MS M + H |
|---|---|---|---|
| 62 | 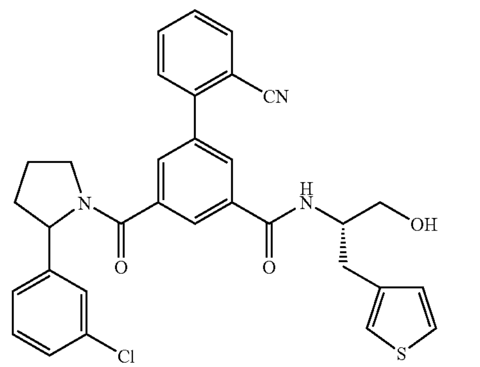 | Schemes 5, 8 | 571 |
| 63 | 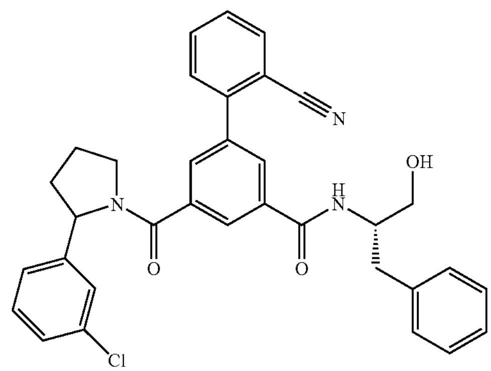 | Schemes 5, 8 | 565 |
| 64 | 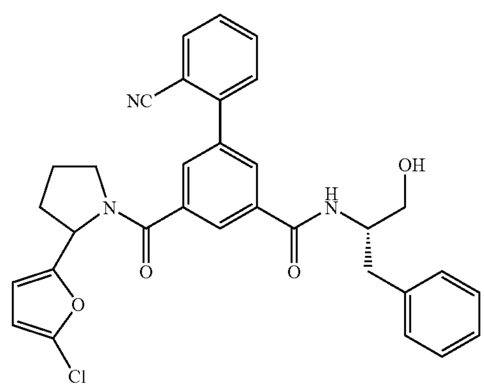 | Schemes 5, 8 | 555 |
| 65 | 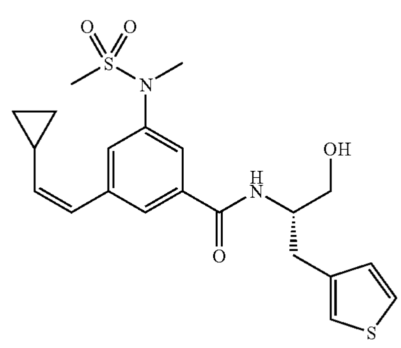 | Schemes 7, 8 | 435 |

| Example | Structure | Schemes & Intermediates | ES MS M + H |
|---|---|---|---|
| 66 | 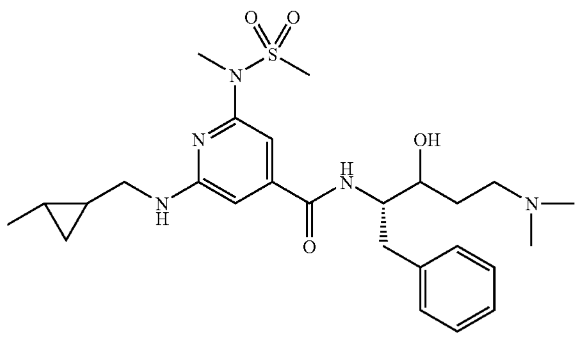 | Schemes 1, 8<br>Intermediates A, XII | 518 |
| 67 | 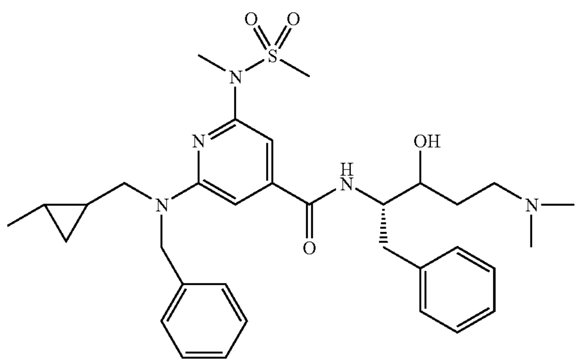 | Schemes 1, 8<br>Intermediate XII | 608 |
| 68 | 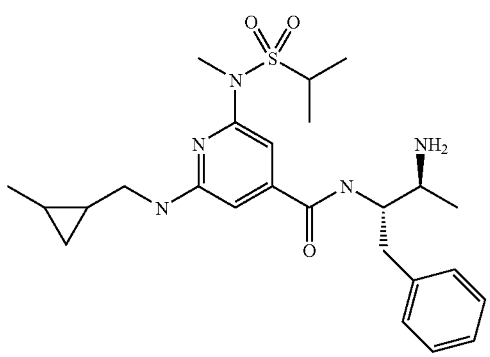 | Schemes 1, 8<br>Intermediate XIII | 488 |
| 69 | 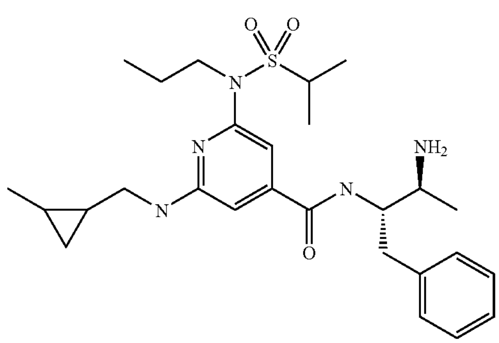 | Schemes 1, 8<br>Intermediate XIII | 516 |

-continued
| Example | Structure | Schemes & Intermediates | ES MS M + H |
|---|---|---|---|
| 70 | 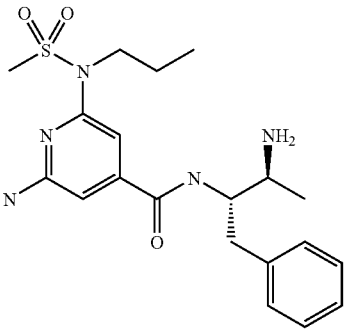 | Schemes 1, 8<br>Intermediate XIII | 488 |
| 71 | 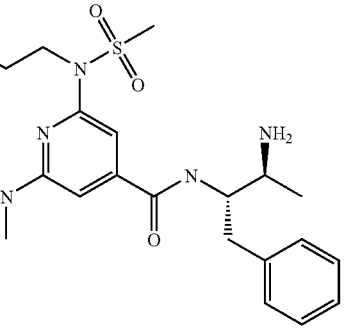 | Schemes 1, 8<br>Intermediate XIII | 502 |
| 72 | 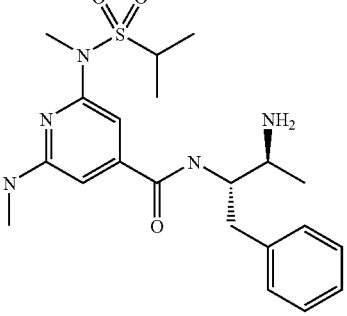 | Schemes 1, 8<br>Intermediate XIII | 502 |
| 73 | 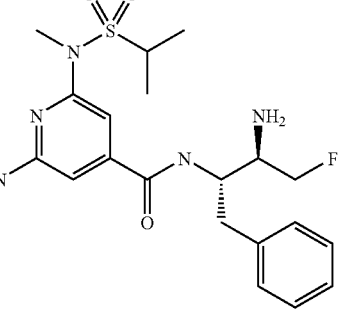 | Schemes 1, 8<br>Intermediate XIV | 506 |

-continued

| Example | Structure | Schemes & Intermediates | ES MS M + H |
|---|---|---|---|
| 74 | 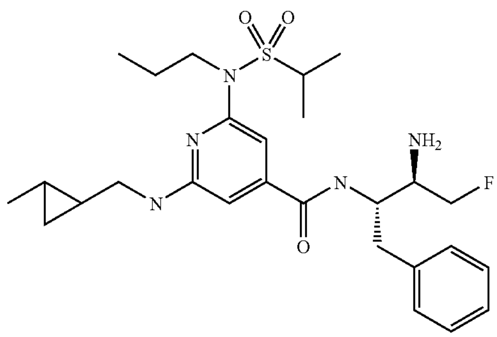 | Schemes 1, 8 Intermediate XIV | 534 |
| 75 | 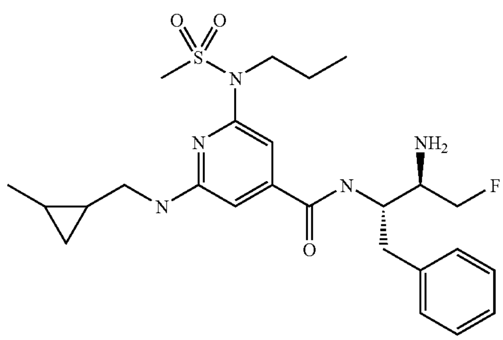 | Schemes 1, 8 Intermediate XIV | 506 |
| 76 | 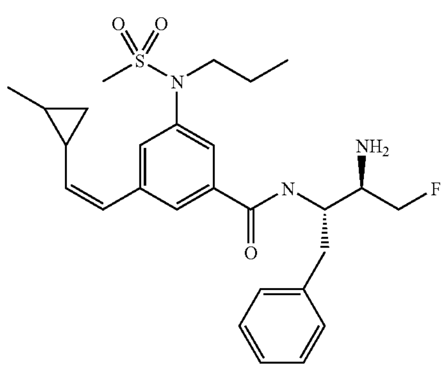 | Schemes 7, 8 Intermediate XIV | 502 |
| 77 | 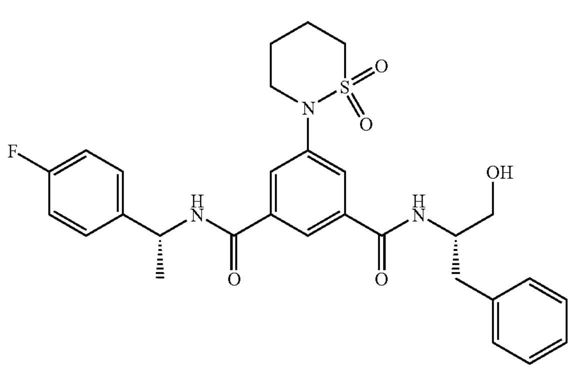 | Schemes 5, 8 | 554 |

| Example | Structure | Schemes & Intermediates | ES MS M + H |
|---|---|---|---|
| 78 | 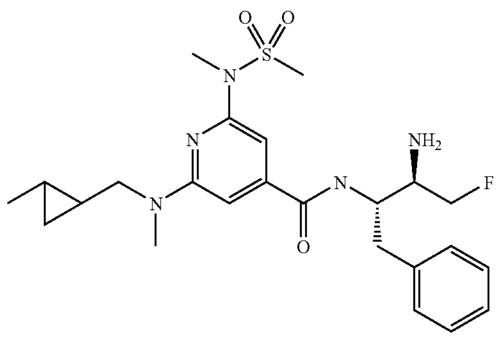 | Schemes 3, 4, 8<br>Intermediates IV, XXI | 492 |
| 79 | 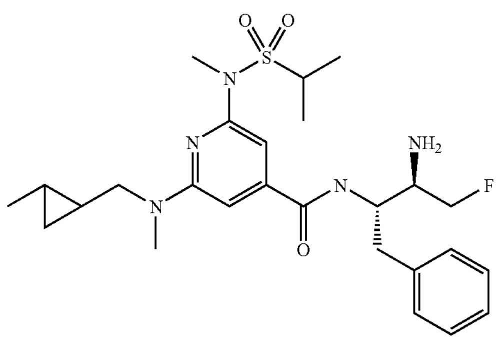 | Schemes 3, 4, 8<br>Intermediates XIV, XXI | 520 |
| 80 | 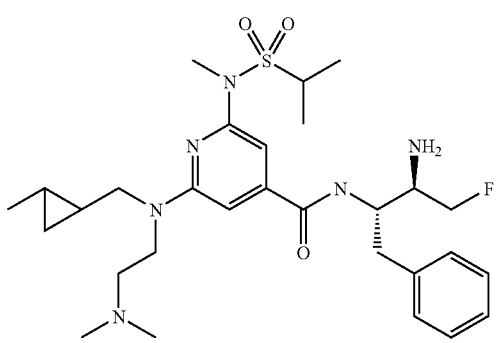 | Schemes 3, 4, 8<br>Intermediates XIV, XVIII | 577 |
| 81 | 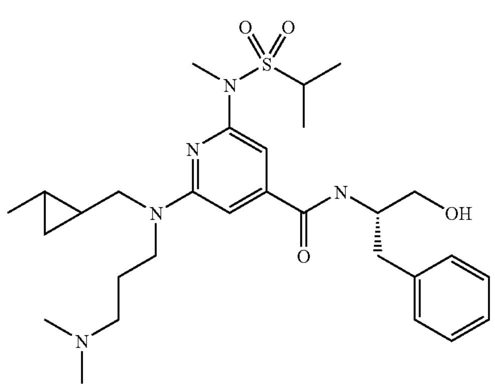 | Schemes 3, 4, 8<br>Intermediate XIX | 560 |

-continued

| Example | Structure | Schemes & Intermediates | ES MS M + H |
|---|---|---|---|
| 82 | 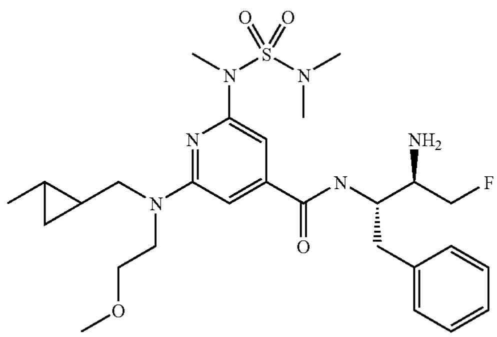 | Schemes 3, 4, 8<br>Intermediates XIV, XV | 565 |
| 83 | 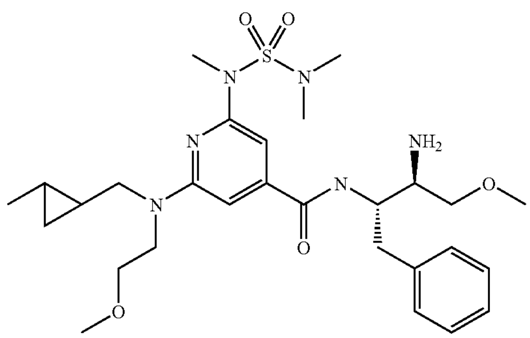 | Schemes 3, 4, 8<br>Intermediate XV | 577 |
| 84 | 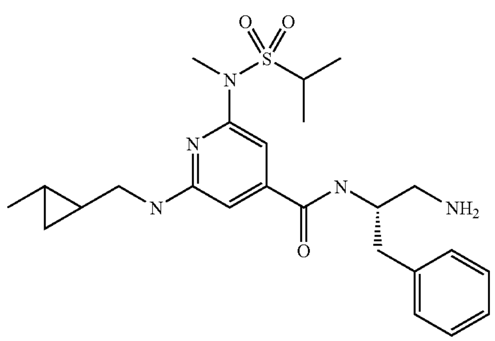 | Schemes 3, 4, 8<br>Intermediates XI | 474 |
| 85 | 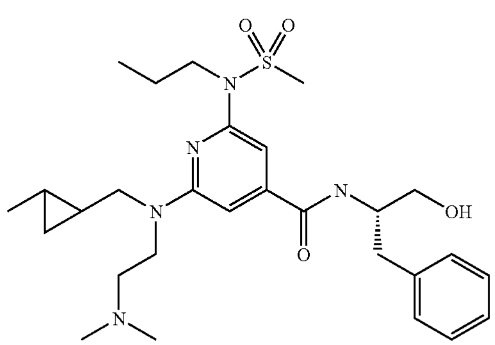 | Schemes 3, 4, 8<br>Intermediate XVIII | 546 |

-continued

| Example | Structure | Schemes & Intermediates | ES MS M + H |
|---|---|---|---|
| 86 | 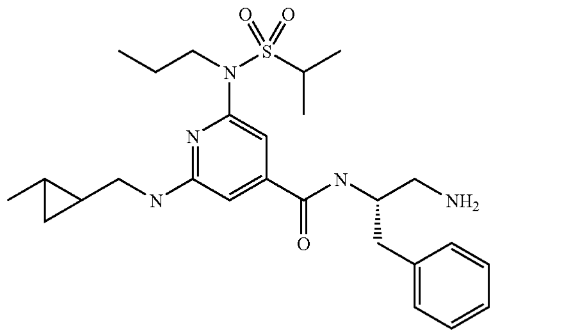 | Schemes 3, 4, 8<br>Intermediate XI | 502 |
| 87 | 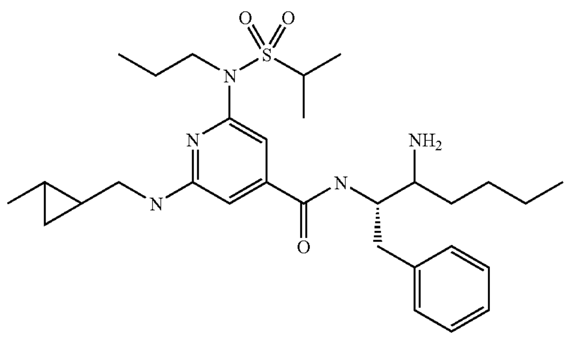 | Schemes 3, 4, 8<br>Intermediates I, XI | 558 |
| 88 | 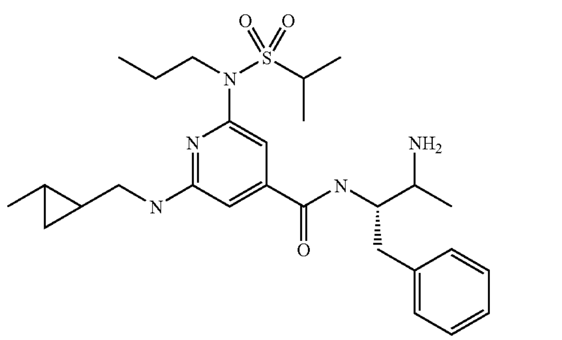 | Schemes 3, 4, 8<br>Intermediates XI, XIII | 516 |
| 89 | 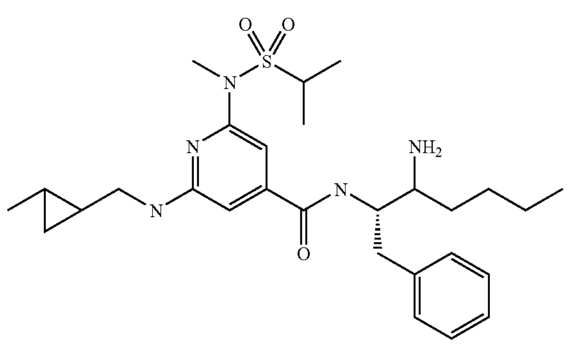 | Schemes 3, 4, 8<br>Intermediates I, XI | 530 |

-continued

| Example | Structure | Schemes & Intermediates | ES MS M + H |
|---------|-----------|-------------------------|-------------|
| 90 | 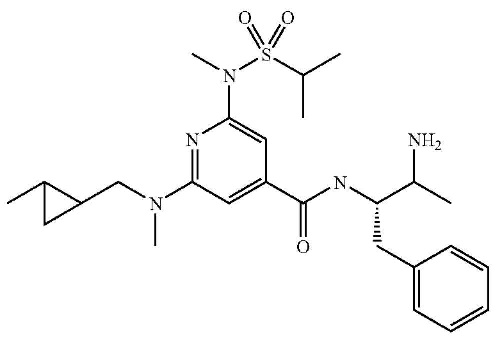 | Schemes 3, 4, 8<br>Intermediates XIII, XXI | 502 |
| 91 | 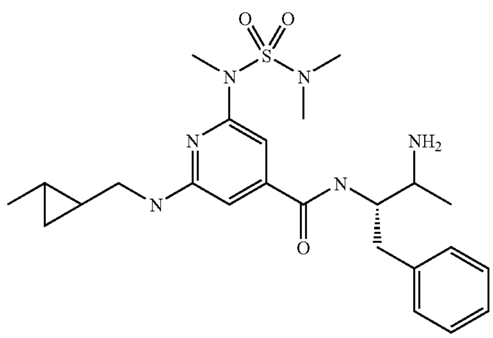 | Schemes 3, 4, 8<br>Intermediates XI, XIII | 489 |
| 92 | 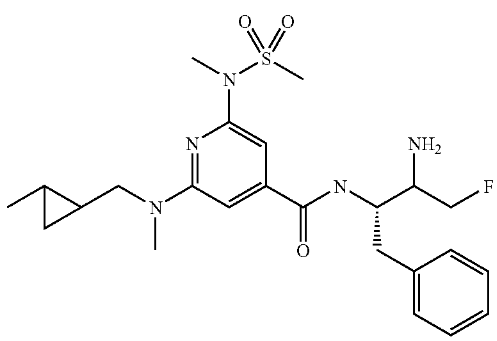 | Schemes 3, 4, 8<br>Intermediates XIV, XXI | 492 |
| 93 | 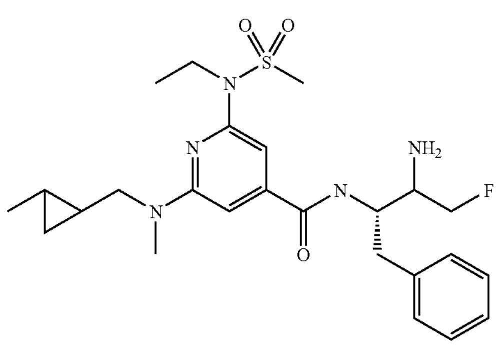 | Schemes 3, 4, 8<br>Intermediates XIV, XXI | 506 |

| Example | Structure | Schemes & Intermediates | ES MS M + H |
|---|---|---|---|
| 94 | 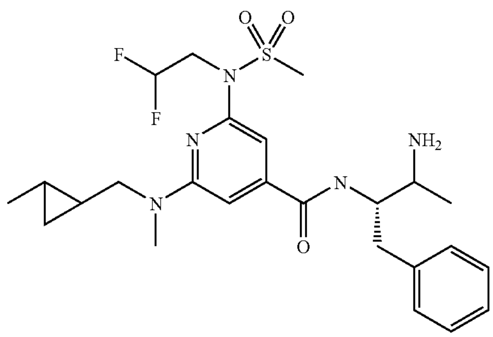 | Schemes 3, 4, 8<br>Intermediates XIII, XXI | 524 |
| 95 | 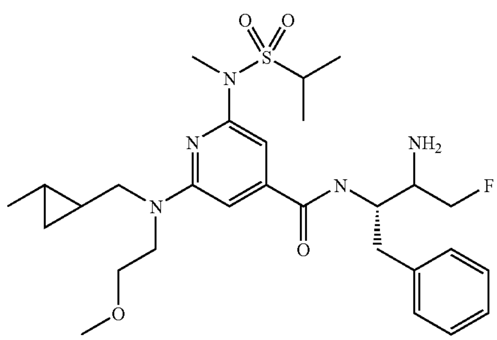 | Schemes 3, 4, 8<br>Intermediates XIV, XV | 564 |
| 96 | 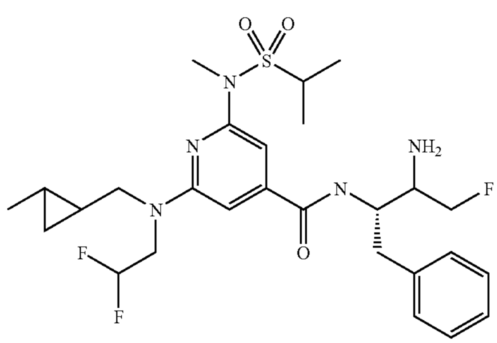 | Schemes 3, 4, 8<br>Intermediates XIV, XVII | 570 |
| 97 | 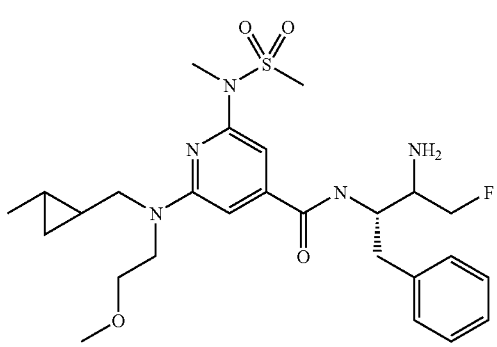 | Schemes 3, 4, 8<br>Intermediates XIV, XV | 536 |

-continued

| Example | Structure | Schemes & Intermediates | ES MS M + H |
|---|---|---|---|
| 98 | 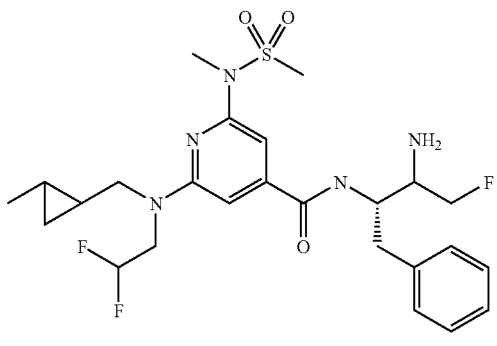 | Schemes 3, 4, 8<br>Intermediates XIV, XVII | 542 |
| 99 | 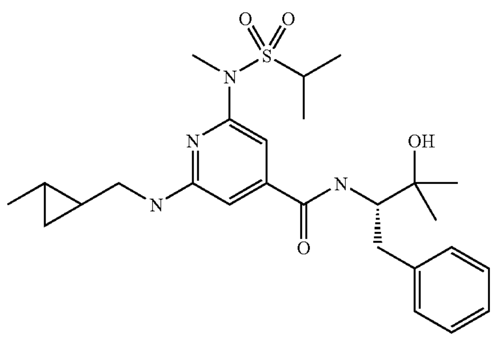 | Schemes 3, 4, 8<br>Intermediates XI, XX | 503 |
| 100 | 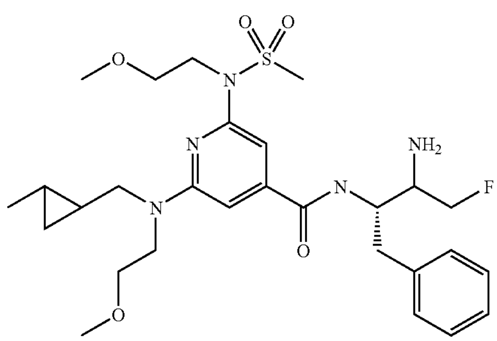 | Schemes 3, 4, 8<br>Intermediates XIV, XV | 580 |
| 101 | 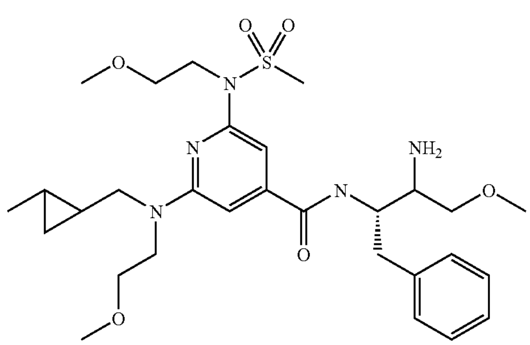 | Schemes 3, 4, 8<br>Intermediate XV | 592 |

-continued

| Example | Structure | Schemes & Intermediates | ES MS M + H |
|---|---|---|---|
| 102 | 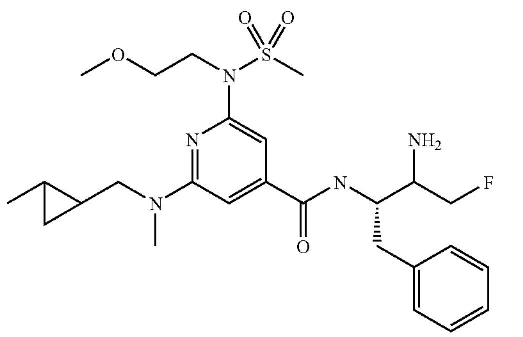 | Schemes 3, 4, 8<br>Intermediates XIV, XXI | 536 |
| 103 | 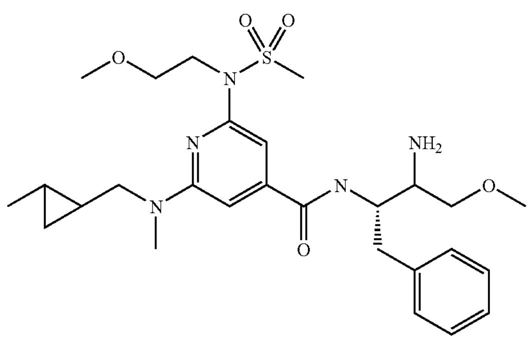 | Schemes 3, 4, 8<br>Intermediate XXI | 548 |
| 104 | 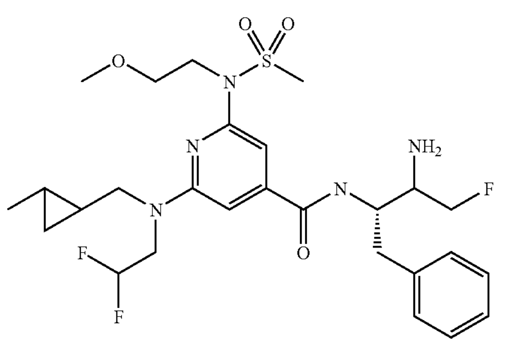 | Schemes 3, 4, 8<br>Intermediate XIV, XVII | 586 |
| 105 | 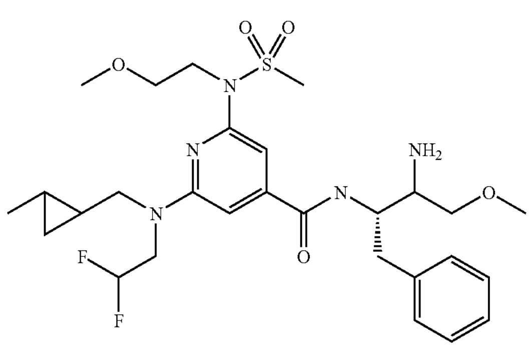 | Schemes 3, 4, 8<br>Intermediate XVII | 598 |

-continued

| Example | Structure | Schemes & Intermediates | ES MS M + H |
|---------|-----------|-------------------------|-------------|
| 106 | 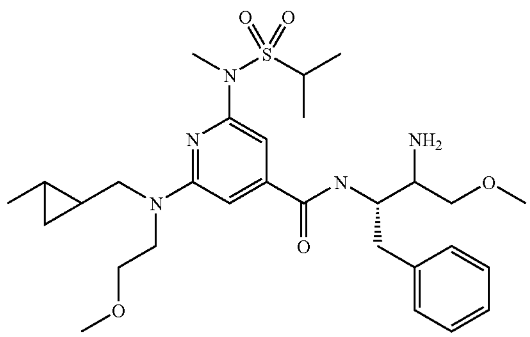 | Schemes 3, 4, 8<br>Intermediate XV | 576 |
| 107 | 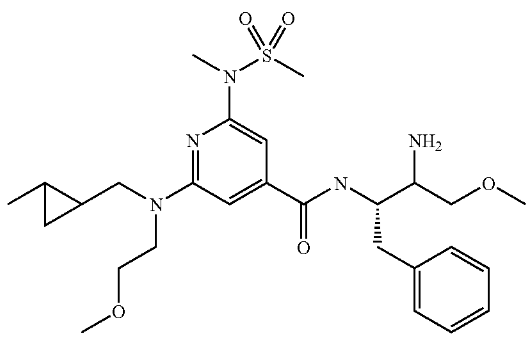 | Schemes 3, 4, 8<br>Intermediate XV | 548 |
| 108 | 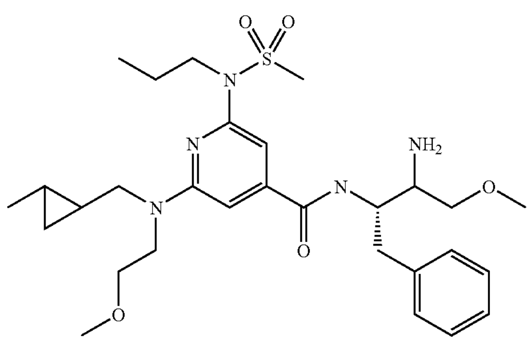 | Schemes 3, 4, 8<br>Intermediate XV | 576 |
| 109 | 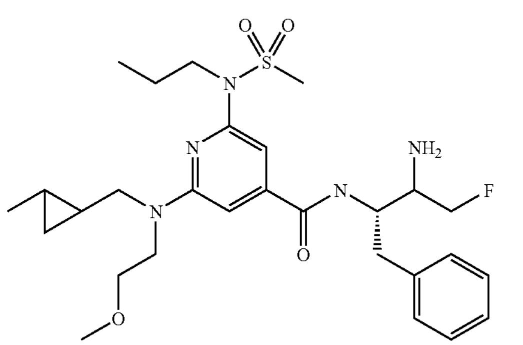 | Schemes 3, 4, 8<br>Intermediates XIV, XV | 564 |

-continued

| Example | Structure | Schemes & Intermediates | ES MS M + H |
|---|---|---|---|
| 110 | 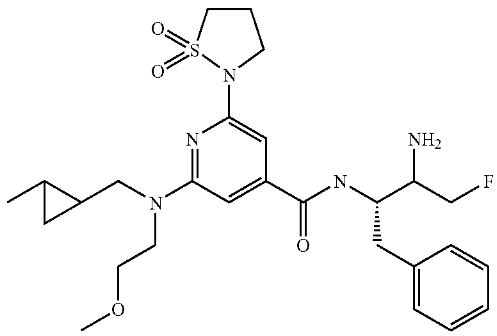 | Schemes 3, 4, 8<br>Intermediates XIV, XV | 548 |
| 111 | 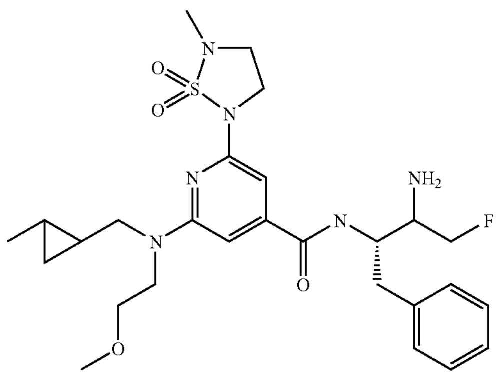 | Schemes 3, 4, 8<br>Intermediates XIV, XV | 563 |
| 112 | 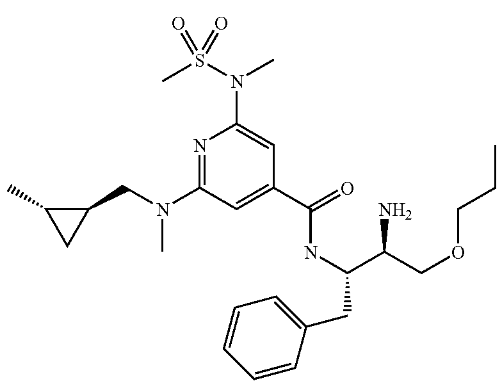 | Schemes 3, 4, 8<br>Intermediates XXI, XXIV | 560 |
| 113 | 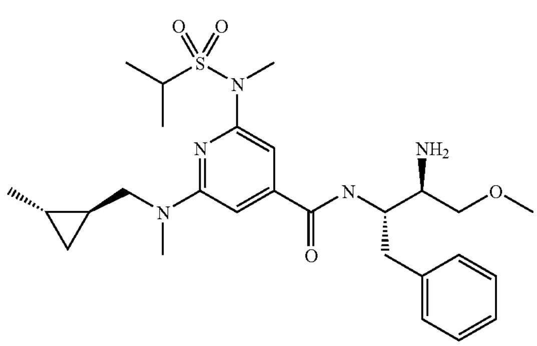 | Schemes 3, 4, 8<br>Intermediates XXI, XXIII | 532 |

| Example | Structure | Schemes & Intermediates | ES MS M + H |
|---|---|---|---|
| 114 | 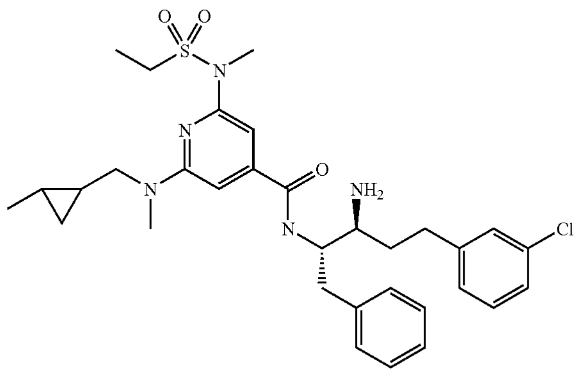 | Schemes 3, 4, 8<br>Intermediates XXI, XXVIII | 613 |
| 115 | 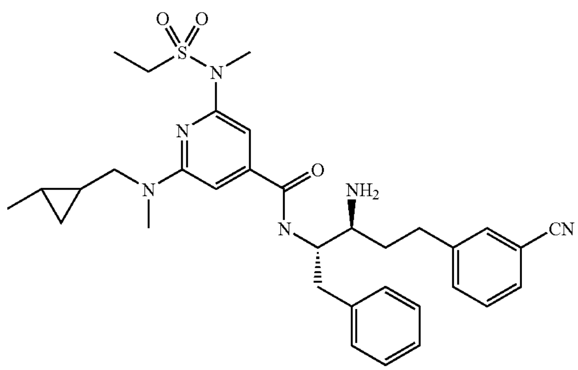 | Schemes 3, 4, 8<br>Intermediate XXI | 603 |
| 116 | 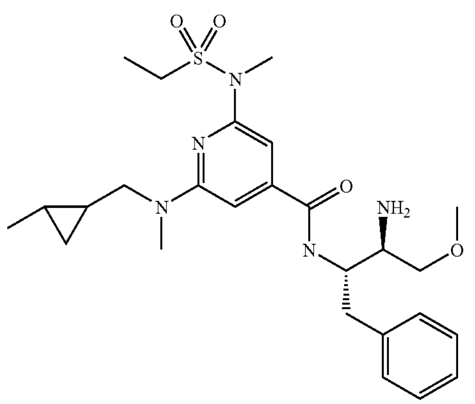 | Schemes 3, 4, 8<br>Intermediates XXI, XXIII | 518 |
| 117 | 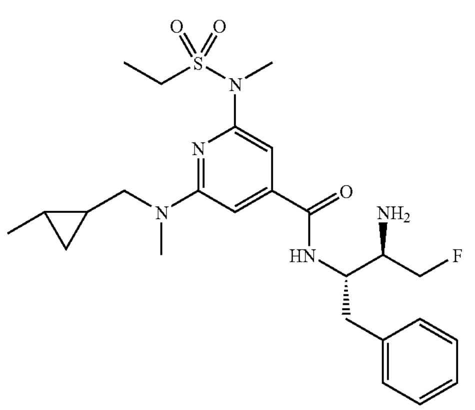 | Schemes 3, 4, 8<br>Intermediates XXI, XIV | 506 |

-continued

| Example | Structure | Schemes & Intermediates | ES MS M + H |
|---|---|---|---|
| 118 | 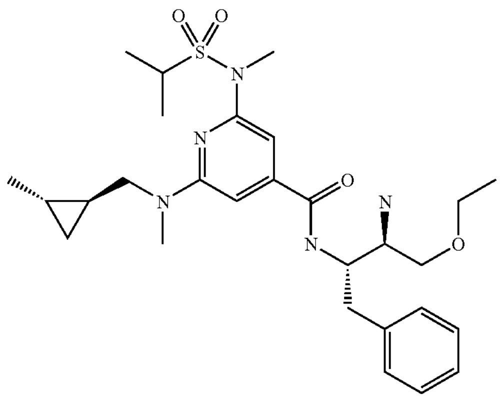 | Schemes 3, 4, 8<br>Intermediates XXI, XXII | 543 |
| 119 | 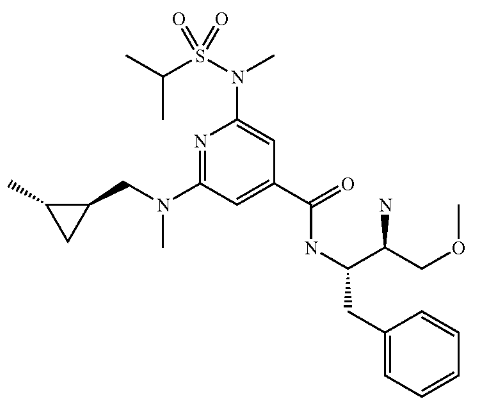 | Schemes 3, 4, 8<br>Intermediates XXI, XXIII | 529 |
| 120 | 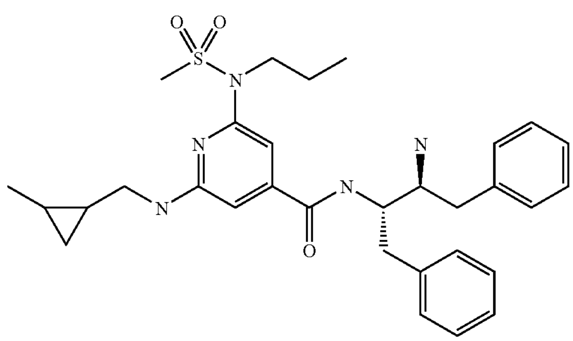 | Schemes 3, 4, 8<br>Intermediate XI | 564 |
| 121 | 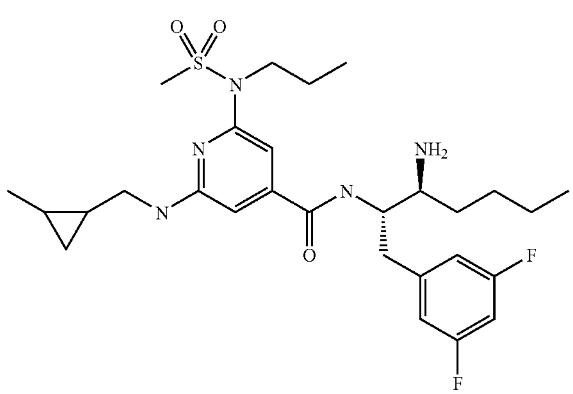 | Schemes 3, 4, 8<br>Intermediates XIII, XI | 566 |

-continued

| Example | Structure | Schemes & Intermediates | ES MS M + H |
|---|---|---|---|
| 122 | 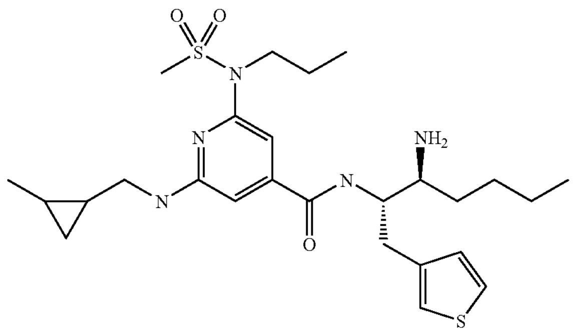 | Schemes 3, 4, 8 Intermediates XI, V | 536 |
| 123 | 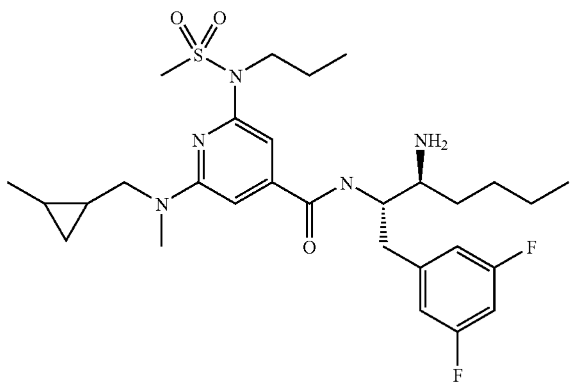 | Schemes 3, 4, 8 Intermediates XXI, XI | 580 |
| 124 | 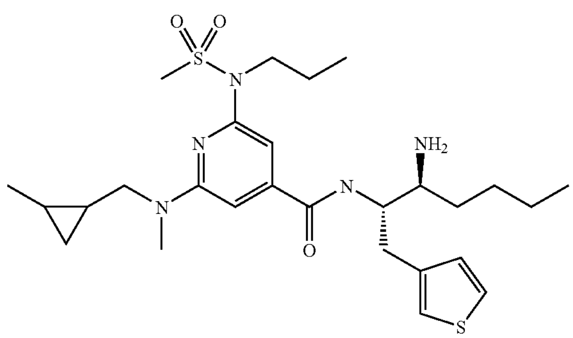 | Schemes 3, 4, 8 Intermediates XXI, V | 550 |
| 125 | 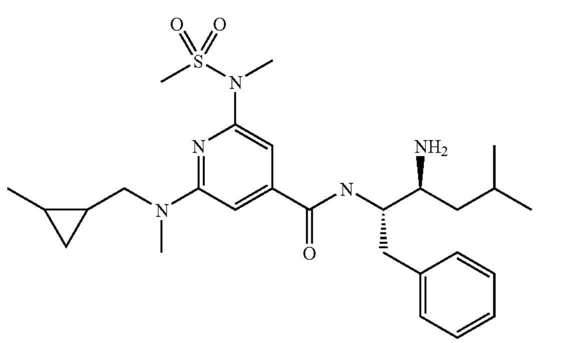 | Schemes 3, 4, 8 Intermediate XXI | 516 |

| Example | Structure | Schemes & Intermediates | ES MS M + H |
|---|---|---|---|
| 126 | 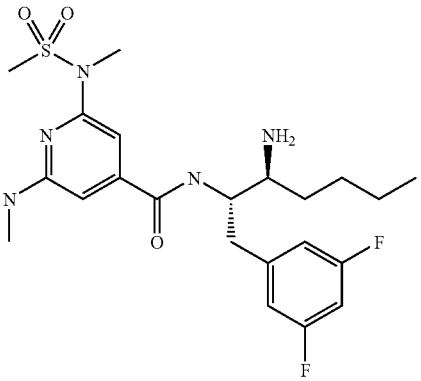 | Schemes 3, 4, 8<br>Intermediates XXI, XI | 552 |
| 127 | 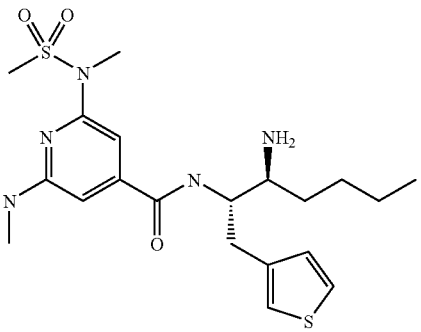 | Schemes 3, 4, 8<br>Intermediates XXI, V | 522 |
| 128 | 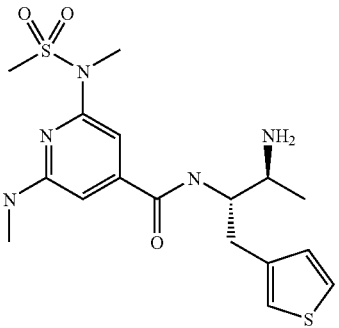 | Schemes 3, 4, 8<br>Intermediates XXI, VI | 480 |
| 129 | 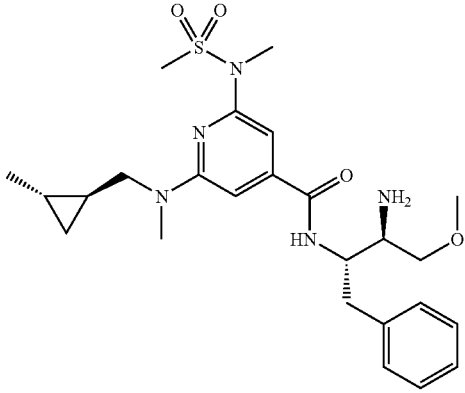 | Schemes 3, 4, 8<br>Intermediates XXI, XXIII | 504 |

-continued

| Example | Structure | Schemes & Intermediates | ES MS M + H |
|---|---|---|---|
| 130 | 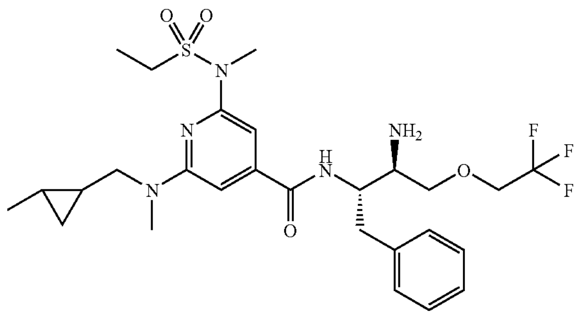 | Schemes 3, 4, 8<br>Intermediate XXI | 586 |
| 131 | 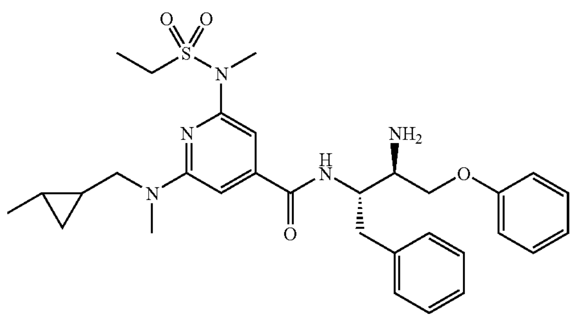 | Schemes 3, 4, 8<br>Intermediate XXI | 580 |
| 132 | 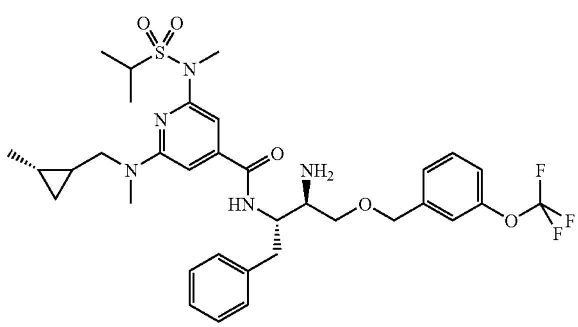 | Schemes 3, 4, 8<br>Intermediates XXI, XXVI | 692 |
| 133 | 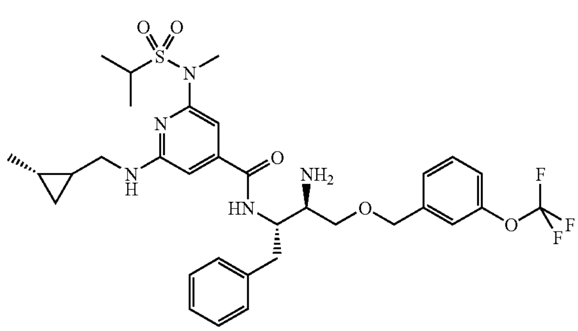 | Schemes 3, 4, 8<br>Intermediates XI, XXVI | 678 |

-continued

| Example | Structure | Schemes & Intermediates | ES MS M + H |
|---|---|---|---|
| 134 | 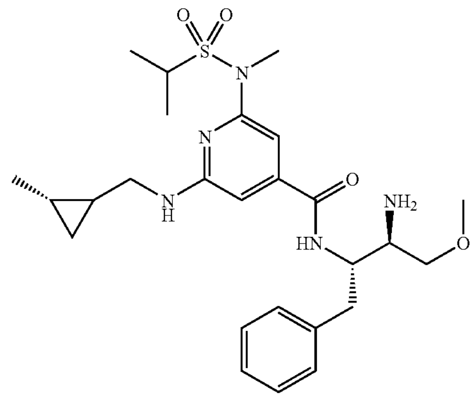 | Schemes 3, 4, 8<br>Intermediates XI, XXIII | 518 |
| 135 | 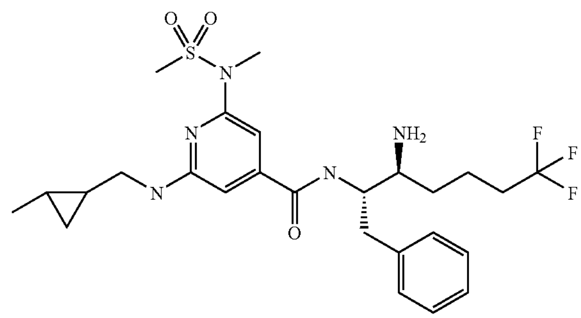 | Schemes 3, 4, 8<br>Intermediates XI, XXX | 556 |
| 136 | 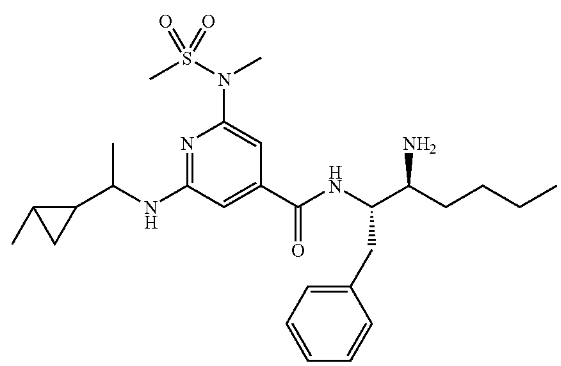 | Schemes 3, 4, 8<br>Intermediates I, XXIX | 516 |
| 137 | 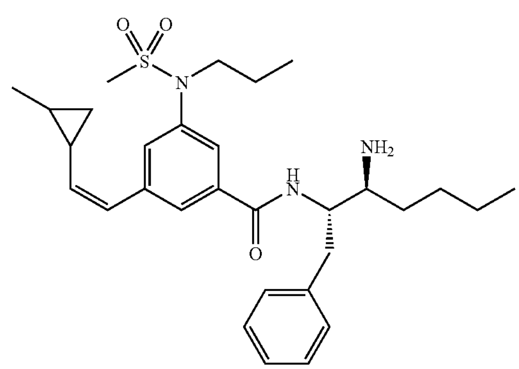 | Schemes 7, 8<br>Intermediate I | 526 |

| Example | Structure | Schemes & Intermediates | ES MS M + H |
|---|---|---|---|
| 138 | 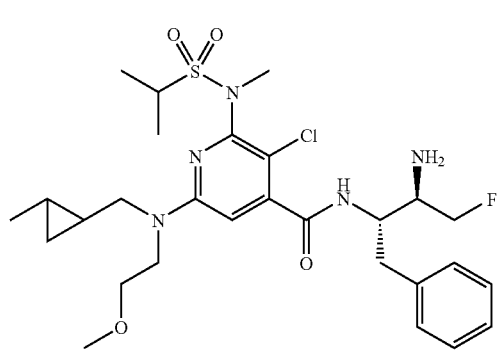 | Schemes 3, 4, 8 Intermediate XI, XXVII | 542 |

EXAMPLE 139

N-[(1S,2R)-2-amino-1-benzyl-3-fluoropropyl]-3-chloro-2-[(isopropylsulfonyl)(methyl)amino]-6-((2-methoxyethyl){[(1S,2S)-2-methylcyclopropyl]methyl}amino)isonicotinamide (Scheme 8)

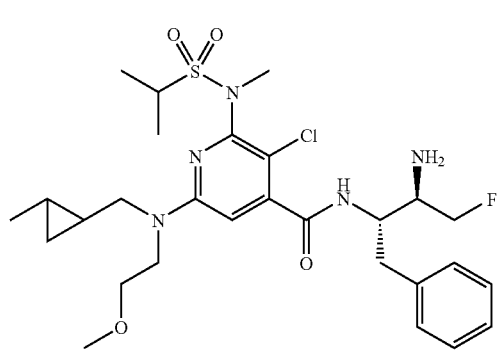

N-[(1S,2R)-2-amino-1-benzyl-3-fluoropropyl]-2-[(isopropylsulfonyl)(methyl)amino]-6-((2-methoxyethyl){[(1S,2S)-2-methylcyclopropyl]methyl}amino)isonicotinamide was prepared via procedure described in Example 95.

A solution of N-[(1S,2R)-2-amino-1-benzyl-3-fluoropropyl]-2-[(isopropylsulfonyl)(methyl)amino]-6-((2-methoxyethyl){[(1S,2S)-2-methylcyclopropyl]methyl}amino)isonicotinamide trifluoroacetate (0.11 g, 0.2 mmol) in 5 mL methylene chloride was treated with NCS (0.026 g, 0.2 mmol) and the resulting mixture was stirred at ambient temperature for 24 hours. The reaction was evaporated in vacuo and purified by reverse phase LC to generate N-[(1S,2R)-2-amino-1-benzyl-3-fluoropropyl]-3-chloro-2-[(isopropylsulfonyl)(methyl)amino]-6-((2-methoxyethyl){[(1S,2S)-2-methylcyclopropyl]methyl}amino)isonicotinamide trifluoroacetate as a yellow solid: $^1$H NMR (CDCl$_3$) δ 7.25 (m, 5H), 6.21 (s, 1H), 4.65 (m, 4H), 3.85 (m, 1H), 3.60 (m, 3H), 3.40 (m, 3H), 3.31 (s, 3H), 3.22 (s, 3H), 3.18 (m, 2H), 1.42 (m, 6H), 1.01 (d, J=5.8 Hz, 3H), 0.64 (m, 2H), 0.36 (m, 1H), 0.25 (m, 1H). ES MS (M+H)=598.8.

EXAMPLE 140

N-[(1S,2R)-2-amino-1-benzyl-3-methoxypropyl]-3-fluoro-2-[(isopropysulfonyl)(methyl)amino]-6-({[(1S,2S)-2-methylcyclopropyl]methyl}amino)isonicotinamide

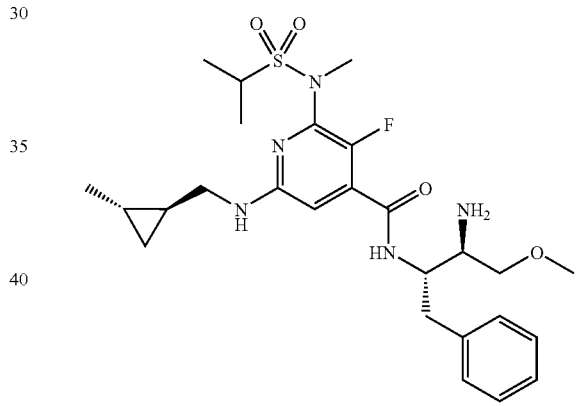

To a solution of N-[(1S,2R)-2-amino-1-benzyl-3-methoxypropyl]-2-[(isopropylsulfonyl)(methyl)amino]-6-({[(1S,2S)-2-methylcyclopropyl]methyl}amino)isonicotinamide (Example 134, 21 mg, 0.033 mmol) in DMF was added Selectfluor (12 mg, 0.033 mmol). The resulting solution was allowed to stir for 18 hours at rt. Purification by reverse-phase chromatography yielded title compound Example 140 as the TFA salt. $^1$H NMR (400 MHz, d$_4$-MeOH) δ 7.32-7.20 (m, 5H), 6.36-6.35 (d, J=3.2 Hz, 1H), 4.58-4.52 (m, 1H), 3.87-3.79 (sep, J=6.8 Hz, 1H) 3.74-3.73 (d, J=4.8 Hz, 2H), 3.63-3.58 (m, 1H), 3.45 (s, 3H), 3.27 (s, 3H), 3.12-3.02 (m, 3H), 2.90-2.83 (m, 1H), 1.43-1.41 (d, J=6.8 Hz, 6H), 1.04-1.02 (d, J=6 Hz, 3H), 0.79-0.74 (m, 1H), 0.66-0.60 (m, 1H), 0.39-0.35 (m, 1H), 0.24-0.19 (m, 1H). ES MS [M+H]=536.1.

The following examples were prepared in an analogous manner to that described in Examples 139 and 140 using various combinations of Intermediates I-XXI or related derivatives thereof and Intermediate acids of types A-D or related derivatives thereof.

| Example | Structure | Schemes & Intermediates | ES MS M + H |
|---|---|---|---|
| 141 | 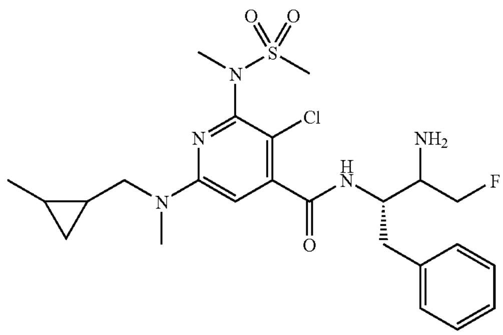 | Schemes 3, 4, 8 Intermediates XIV, XXI | 527 |
| 142 | 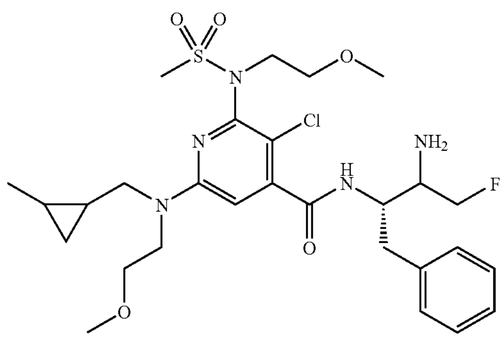 | Schemes 3, 4, 8 Intermediates XIV, XV | 615 |
| 143 | 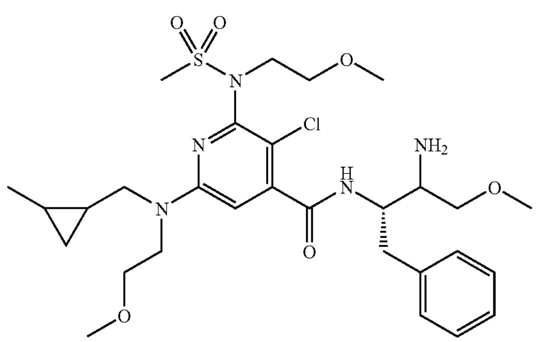 | Schemes 3, 4, 8 Intermediate XV | 627 |
| 144 | 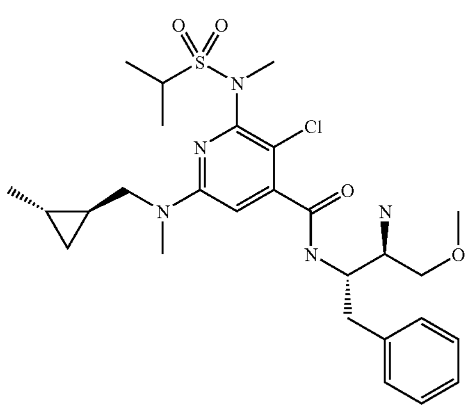 | Schemes 3, 4, 8 Intermediates XXI, XXIII | 563 |

-continued

| Example | Structure | Schemes & Intermediates | ES MS M + H |
|---|---|---|---|
| 145 | 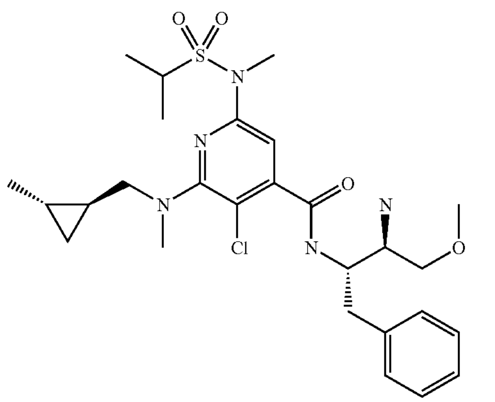 | Schemes 3, 4, 8<br>Intermediates XXI, XXIII | 563 |
| 146 | 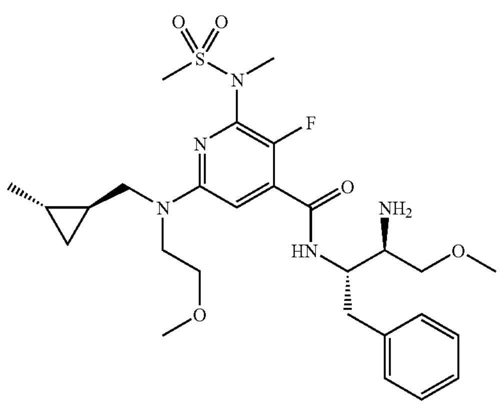 | Schemes 3, 4, 8<br>Intermediates XV, XXIII | 566 |
| 147 | 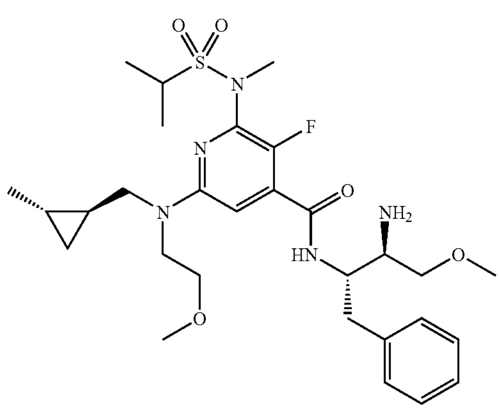 | Schemes 3, 4, 8<br>Intermediates XV, XXIII | 594 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

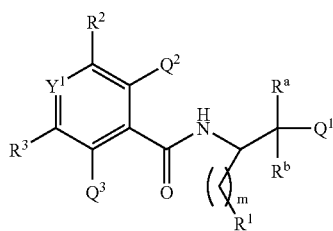

wherein
$Y^1$ is CH or N;
$Q^1$ is —OH;
$Q^2$ and $Q^3$ independently selected from the group consisting of
(1) hydrogen, and
(2) halogen;
$R^a$ is hydrogen;
$R^b$ is selected from the group consisting of
(1) hydrogen, and
(2) —$C_{1-10}$ alkyl,
(3) —$(CH_2)_n$—$NR^cR^d$ wherein $R^c$ and $R^d$ are selected from the group consisting of hydrogen and $C_{1-10}$ alkyl, and n is 2, 3 or 4, and
(4) —$(CH_2)_{n'}$—O—$R^e$, wherein $R^e$ is selected from the group consisting of
(a) $C_{1-10}$ alkyl,
(b) —$C_{0-3}$ alkyl-aryl, wherein said aryl is selected from the group consisting of phenyl and naphthyl,
wherein said alkyl and aryl are unsubstituted or substituted with one or more
(i) halo,
(ii) —OH,
(iii) —CN,
(iv) —O—$C_{1-10}$ alkyl,
and n' is 1, 2, 3 or 4;
m is 1 or 2;
$R^1$ is
(1) aryl selected from the group consisting of phenyl and napthyl, or
(2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
(3) —$C_{1-10}$ alkyl, and
(4) —$C_{3-8}$ cycloalkyl,
wherein said aryl, heteroaryl, alkyl and cycloalkyl is unsubstituted or substituted with one or more
(a) halo,
(b) —OH,
(c) —CN,
(d) —O—$C_{1-10}$ alkyl,
(e) —$C_{1-10}$ alkyl,
(f) —$C_{3-8}$ cycloalkyl,
(g) aryl selected from the group consisting of phenyl and napthyl, or
(h) heteroaryl selected from the group consisting of pyrazinyl, pyrazolyl, pyridazinyl, pyridyl, pyrimnidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;
$R^2$ is selected from the group consisting of:
(1) ($R^4$—$SO_2$)N($R^7$)—, wherein $R^4$ is
(a) —$C_{1-10}$ alkyl,
(b) —$C_{3-8}$ cycloalkyl,
wherein said alkyl and cycloalkyl is unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{3-8}$ cycloalkyl,
(vii) aryl selected from the group consisting of phenyl and napthyl, or
(viii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;
and said aryl and heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) —$C_{1-10}$ alkyl,
(c) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl, or
(vi) —$C_{1-10}$ alkyl,
(d) —$(CH_2)_x$—$NR^fR^g$ wherein $R^f$ and $R^g$ are selected from the group consisting of hydrogen and $C_{1-10}$ alkyl, and x is 0, 1, 2, 3 or 4, or $R^f$ and $R^g$, together with the nitrogen atom to which they are attached form the group

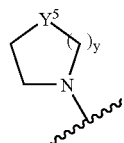

wherein y is 1 or 2, $Y^5$ is —$CHR^{21}$, —O— or $NR^{21}$, wherein $R^{21}$ is selected from the group consisting of;
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl;

$R^7$ is selected from the group consisting of
(a) hydrogen, and
(b) —$C_{1-10}$ alkyl,
(c) aryl selected from the group consisting of phenyl and napthyl, or
(d) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl
wherein said alkyl, aryl and heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) aryl selected from the group consisting of phenyl and napthyl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said cycloalkyl, aryl or heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) aryl selected from the group consisting of phenyl and napthyl;
(e) —$(CH_2)_{y'}$—$NR^hR^i$ wherein $R^h$ and $R^i$ are selected from the group consisting of hydrogen and $C_{1-10}$ alkyl, and y' is 1, 2, 3 or 4, or or $R^h$ and $R^i$, together with the nitrogen atom to which they are attached from the group

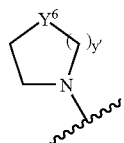

wherein y' is 1 or 2, $Y^6$ is —$CHR^{22}$, —O— or $NR^{22}$, wherein $R^{22}$ is selected from the group consisting of;
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl,
or $R^4$ and $R^7$ are linked together to form the group (a)

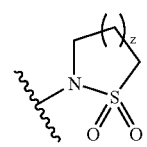

wherein z is 1, 2 or 3; or (b)

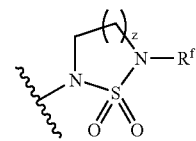

wherein z is 1, 2 or 3

(2)

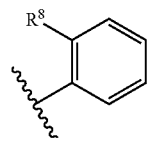

wherein $R^8$ is selected from the group consisting of
(a) —CN,
(b) hydrogen, and
(c) tetrazolyl;

(3)

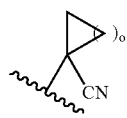

wherein o is 1, 2, 3 or 4; and (4)

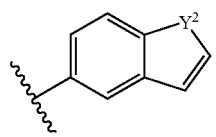

wherein Y² is —NH═CH— or —CH═NH—;
R³ is selected from the group consisting of (1)

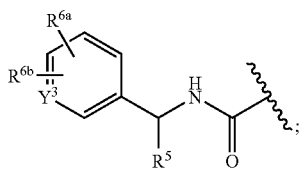

(2)

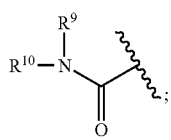

(3)

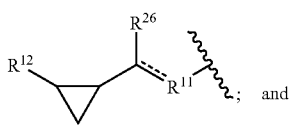
; and (4)

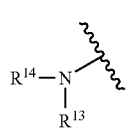

wherein Y³ is CR$^{6c}$ or N;
R⁵ is C$_{1-10}$ alkyl or C$_{1-2}$ perfluoroalkyl;
R$^{6a}$, R$^{6b}$, and R$^{6c}$ are independently selected from the group consisting of:
(1) hydrogen,
(2) halo,
(3) —C$_{1-10}$ alkyl,
(4) —OH,
(5) —CN,
(6) —C$_{3-8}$ cycloalkyl, and
(7) —O—C$_{1-10}$ alkyl;
R⁹ and R¹⁰ are independently selected from the group consisting of
(1) hydrogen,
(2) —C$_{1-10}$ alkyl, and
(3) —C$_{3-8}$ cycloalkyl,
wherein said alkyl and cycloalkyl are unsubstituted or substituted with one or more
(a) halo,
(b) —OH,
(c) —CN,
(d) —O—C$_{1-10}$ alkyl,
(e) —C$_{3-8}$ cycloalkyl, and
(f) —NR$^{j}$R$^{k}$ wherein R$^{j}$ and R$^{k}$ are C$_{1-10}$ alkyl;
or R⁹ and R¹⁰ are joined together with the nitrogen atom to which they are attached to form

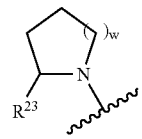

wherein w is 1, 2 or 3, and
R²³ is selected from the group consisting of
(a) hydrogen,
(b) —C$_{1-10}$ alkyl,
(c) —C$_{3-8}$ cycloalkyl,
(d) —C$_{2-10}$ alkenyl,
(e) —C$_{2-10}$ alkynyl,
(f) —(CH$_2$)$_p$-phenyl,
(g) —(CH$_2$)$_p$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein p is 0 or 1, and
wherein said alkyl, alkenyl, alkynyl, cycloalkyl, phenyl and heteroaryl is unsubstituted or substituted with one or more
(i) halo,
(ii) —C$_{1-10}$ alkyl,
(iii) —OH,
(iv) —CN,
(v) —C$_{3-8}$ cycloalkyl, or
(vi) —O—C$_{1-10}$ alkyl;
R¹¹ is selected from the group consisting of
(1) —CH—
(2) —CH$_2$—,
(3) —O—, and
(4) —NR¹⁷—,
provided that when R¹¹ is —CH— the dotted line forms a bond and when R¹¹ is —CH$_2$—, —O— or —NR¹⁷— the dotted line is absent;
R¹⁷ is hydrogen or C$_{1-10}$ alkyl, wherein said C$_{1-10}$ alkyl is unsubstituted or substituted with one or more
(a) halo,
(b) —OH,
(c) —CN,
(d) —C$_{3-8}$ cycloalkyl,
(e) —O—C$_{1-10}$ alkyl,
(f) —(CH$_2$)$_q$-phenyl, wherein q is 1 or 2, and
(g) —NR¹⁸R¹⁹, and
wherein R¹⁸ and R¹⁹ are independently selected from the group consisting of
(i) hydrogen, or
(ii) C$_{1-10}$ alkyl;
or R¹⁸ and R¹⁹, together with the nitrogen atom to which they are attached, form the group

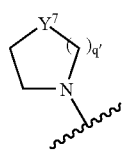

wherein q' is 1 or 2, $Y^7$ is —$CHR^{24}$—, —O— or $NR^{24}$, wherein $R^{24}$ is selected from the group consisting of:
(a) hydrogen, and
(b) $C_{1-10}$ alkyl,
wherein said alkyl is unsubstituted or substituted with one or more
(i) halo,
(ii) —OH,
(iii) —CN,
(iv) —O—$C_{1-10}$ alkyl, or
(v) —$C_{3-8}$ cycloalkyl;
$R^{26}$ is selected from the group consisting of
(1) hydrogen,
(2) —$C_{1-3}$ alkyl;
$R^{12}$ is selected from the group consisting of
(1) hydrogen,
(2) —$C_{1-10}$ alkyl, wherein said alkyl is unsubstituted or substituted with one or more
(a) halo,
(b) —OH,
(c) —CN,
(d) —$C_{3-8}$ cycloalkyl,
(e) —O—$C_{1-10}$ alkyl, or
(f) —$NH_2$,
(3) halo,
(4) —$C_{3-8}$ cycloalkyl,
(5) aryl selected from the group consisting of phenyl and napthyl, and
(6) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl and heteroaryl is unsubstituted or substituted with one or more
(a) halo,
(b) —OH,
(c) —CN,
(d) —O—$C_{1-10}$ alkyl,
(e) —$C_{3-8}$ cycloalkyl, or
(f) —$C_{1-10}$ alkyl;
$R^{13}$ is selected from the group consisting of
(1) hydrogen,
(2) $C_{1-10}$ alkyl, and
(3) —$C_{3-8}$ cycloalkyl;
wherein said alkyl and cycloalkyl is unsubstituted or substituted with one or more
(a) halo,
(b) —OH,
(c) —CN,
(d) —$C_{3-8}$ cycloalkyl,
(e) —O—$C_{1-10}$ alkyl, and
(f) —$C_{1-10}$ alkyl;
$R^{14}$ is selected from the group consisting of
(1) —$C_{1-10}$ alkyl, and
(2) —$C_{3-8}$ cycloalkyl;
wherein said alkyl and cycloalkyl is unsubstituted or substituted with one or more
(a) halo,
(b) —OH,
(c) —CN
(d) —$C_{3-8}$ cycloalkyl,
(e) —O—$C_{1-10}$ alkyl, or
(f) —$C_{1-10}$ alkyl;

(3) —$(CH_2)_v$—$NR^{15}R^{16}$, wherein v is 2, 3 or 4, and
wherein $R^{15}$ and $R^{16}$ are independently selected from the group consisting of
a) hydrogen, or
b) $C_{1-10}$ alkyl, wherein said $C_{1-10}$ alkyl is unsubstituted or substituted with one or more
(i) halo,
(ii) —OH,
(iii) —CN,
(iv) —$C_{3-8}$ cycloalkyl, or
(v) —O—$C_{1-10}$ alkyl;
or $R^{15}$ and $R^{16}$, together with the nitrogen atom to which they are attached, form the group

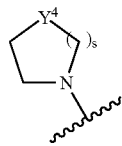

wherein s is 1 or 2, $Y^4$ is —$CHR^{24}$—, —O— or —$NR^{24}$—, wherein $R^{24}$ is selected from the group consisting of
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl,
(4) —$(CH_2)_r$-phenyl, wherein r is 1, 2, 3, or 4, and
wherein said phenyl is unsubstituted or substituted with one or more
(a) halo,
(b) —OH,
(c) —CN,
(d) —O—$C_{1-10}$ alkyl,
(e) —$C_{3-8}$ cycloalkyl, or
(f) —$C_{1-10}$ alkyl;
or $R^{13}$ and $R^{14}$, together with the nitrogen atom to which they are attached, form the group

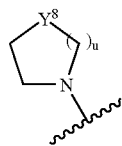

wherein u is 1 or 2, $Y^8$ is —$CHR^{25}$—, —O— or —$NR^{25}$—, wherein $R^{25}$ is selected from the group consisting of
(a) hydrogen,
(b) $C_{1-10}$ alkyl,
(c) —$(CH_2)_t$-phenyl,
(d) —$(CH_2)_t$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein t is 0 or 1, and wherein said alkyl, phenyl and heteroaryl is unsubstituted or substituted with one or more
  (i) halo,
  (ii) —$C_{1-10}$ alkyl,
  (iii) —OH,
  (iv) —CN,
  (v) —$C_{3-8}$ cycloalkyl, or
  (vi) —O—$C_{1-10}$ alkyl;
or a pharmaceutically acceptable salt thereof.

2. The compound of claim 1, or a pharmaceutically acceptable salt thereof, wherein m is 1 and $R^1$ is selected from the group consisting of
  (1) phenyl, unsubstituted or substituted in one or two positions with halo; and
  (2) thienyl.

3. The compound of claim 1, or a pharmaceutically acceptable salt thereof, wherein $R^2$ is $(R^4$—$SO_2)N(R^7)$—.

4. The compound of claim 1, or a pharmaceutically acceptable salt thereof, wherein $R^3$ is (1)

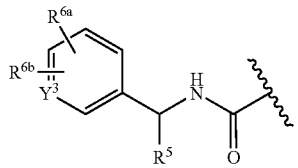

wherein $y^3$ is $CHR^{6c}$, $R^5$ is methyl, $R^{6a}$ and $R^{6c}$ are hydrogen and $R^{6b}$ is fluoro.

5. The compound of claim 1, or a pharmaceutically acceptable salt thereof, wherein $R^3$ is (1)

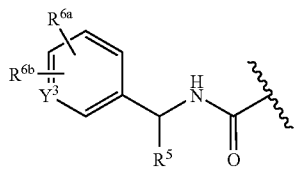

$Y^3$ is N, $R^5$ is $C_{1-2}$ perfluoroalkyl, and $R^{6a}$ and $R^{6b}$ are hydrogen.

6. The compound of claim 1, or a pharmaceutically acceptable salt thereof, wherein $R^3$ is (2)

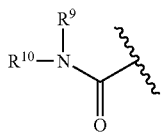

and $R^9$ and $R^{10}$ are each unsubstituted $C_{1-0}$ alkyl, or $R^9$ and $R^{10}$ are joined together with the nitrogen atom to which they are attached to form attached to form

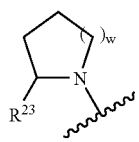

wherein w is 1;

$R^{23}$ is —$(CH_2)_p$-phenyl or —$(CH_2)_p$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, wherein the phenyl and heteroaryl are unsubstituted or substituted with one or more chloro, and p is 0.

7. The compound of claim 1, or a pharmaceutically acceptable salt thereof, wherein $R_3$ is (3)

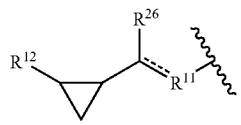

$R^{11}$ is $NR^{17}$ wherein $R^{17}$ is hydrogen or $C_{1-3}$ alkyl, and $R^{12}$ is hydrogen or methyl.

8. The compound of claim 1, or a pharmaceutically acceptable salt thereof, wherein $R^3$ is (4)

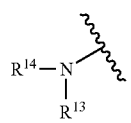

$R^{13}$ is hydrogen and $R^{14}$ is —$(CH_2)_v$—$NR^{15}R^{16}$ wherein v is 2 and $R^{15}$ and $R^{16}$ are each $C_{1-10}$ alkyl, which is unsubstituted or substituted with —OH, —CN or —$OCH_3$.

9. The compound of claim 1, or a pharmaceutically acceptable salt thereof, wherein $R^3$ is (4)

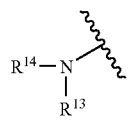

wherein $R^{13}$ and $R^{14}$, together with the nitrogen atom to which they are attached, form the group

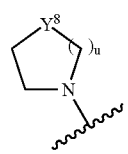

wherein u is 1 or 2, $Y^8$ is —$CHR^{25}$—, —O— or —$NR^{25}$—.

10. A compound of claim 1 which is selected from the group consisting of

137
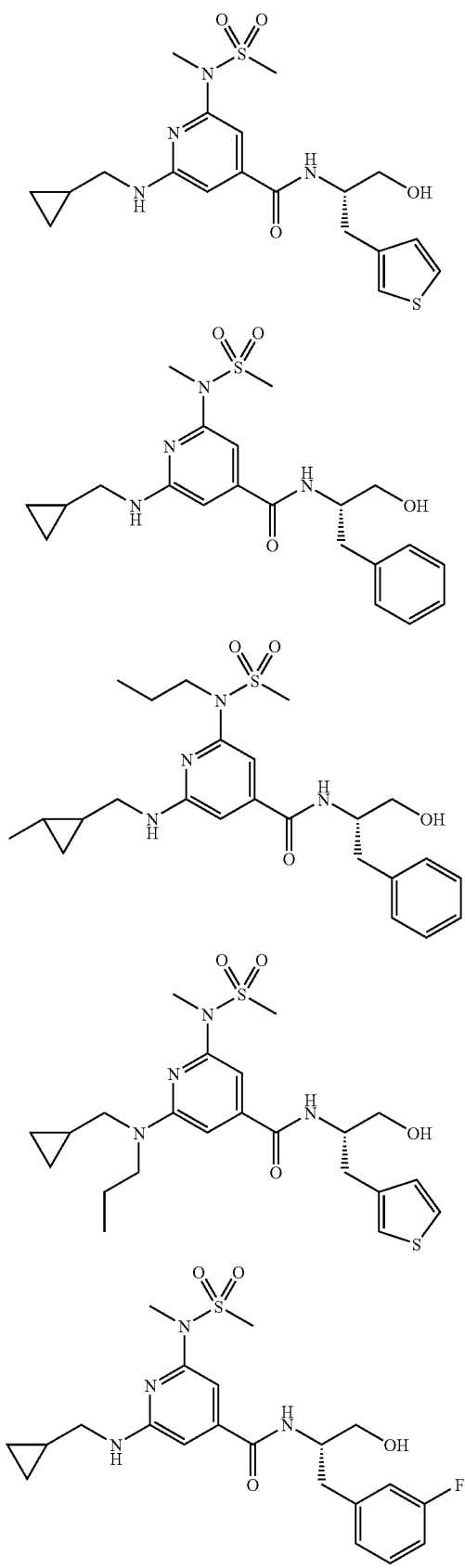
138
-continued
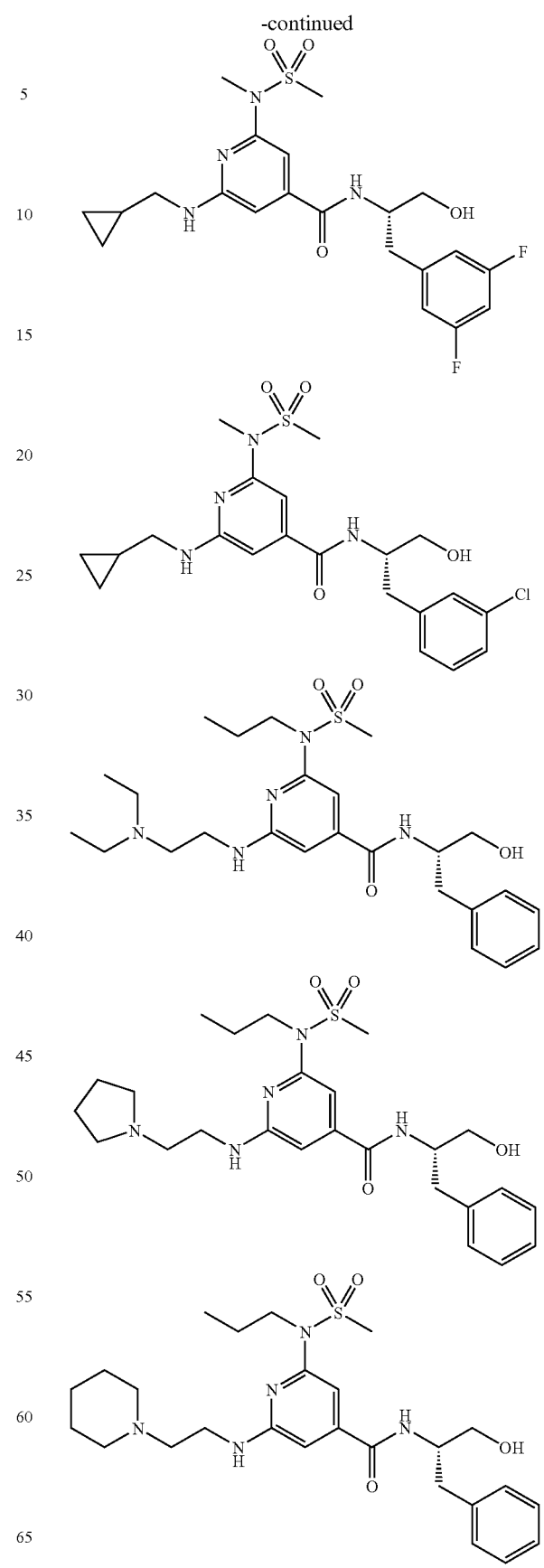

-continued
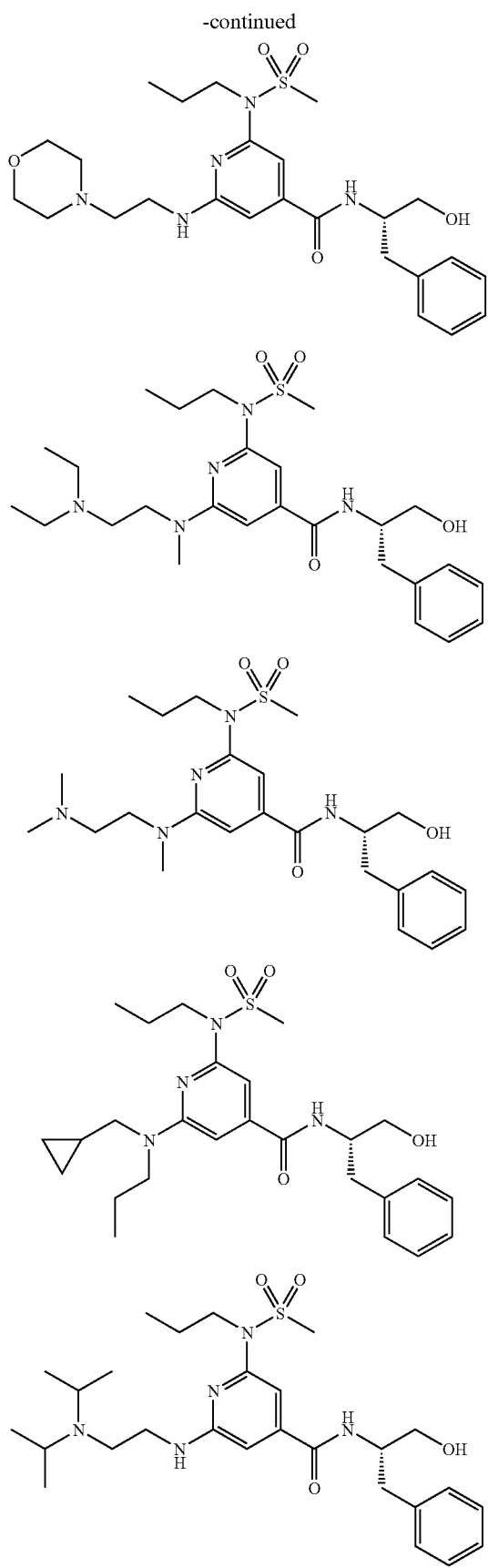
-continued
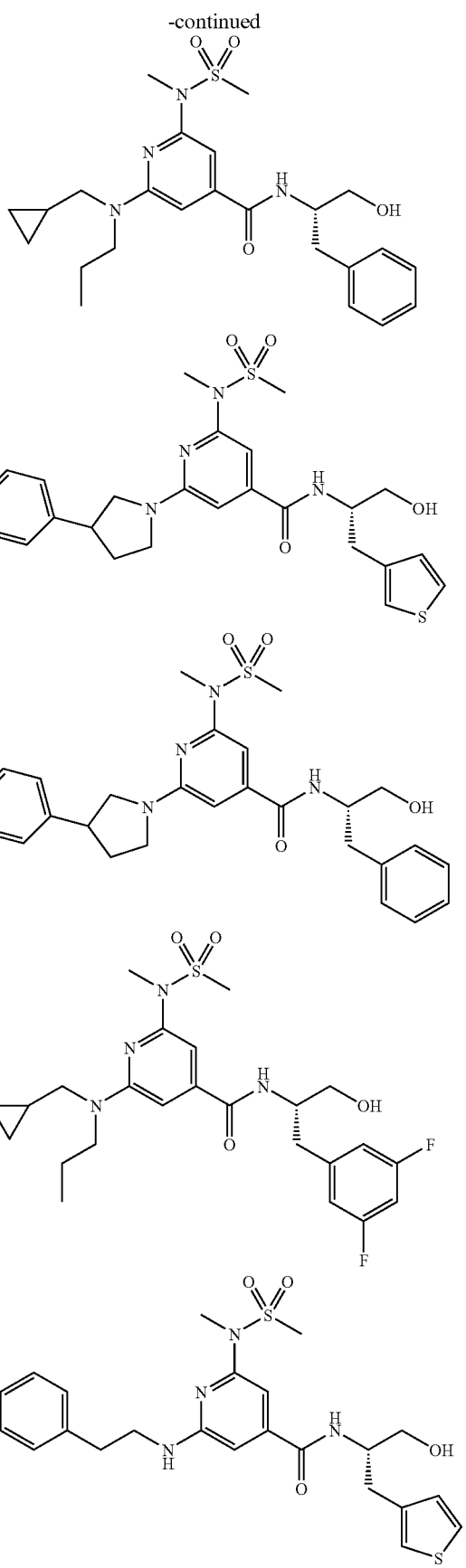

-continued
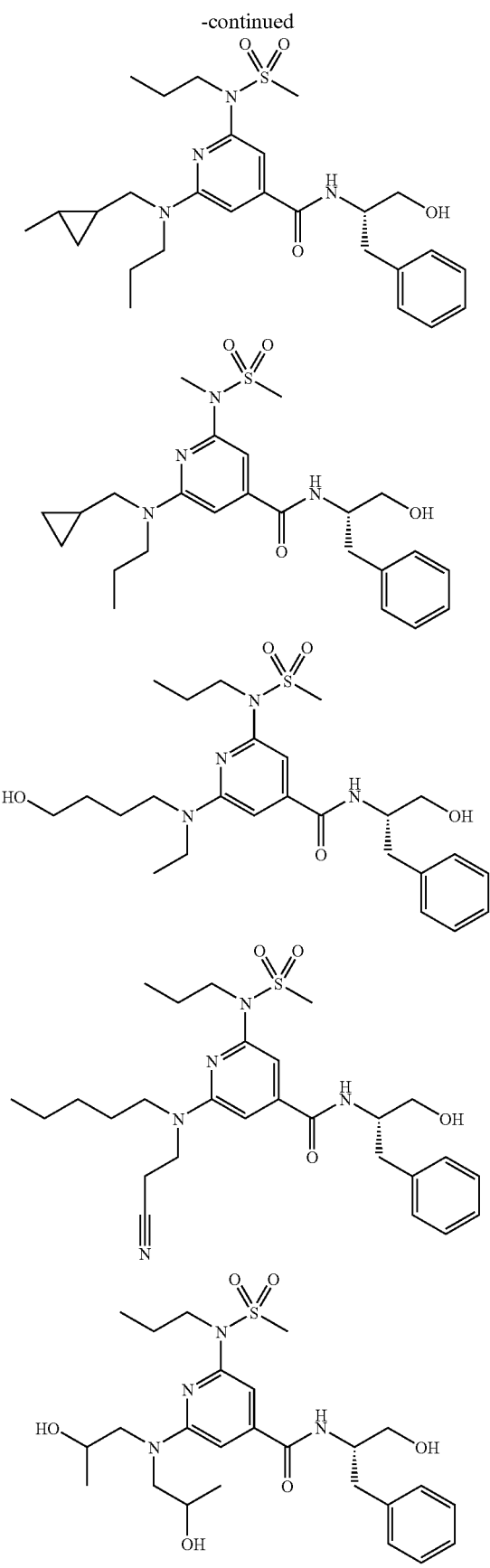
-continued
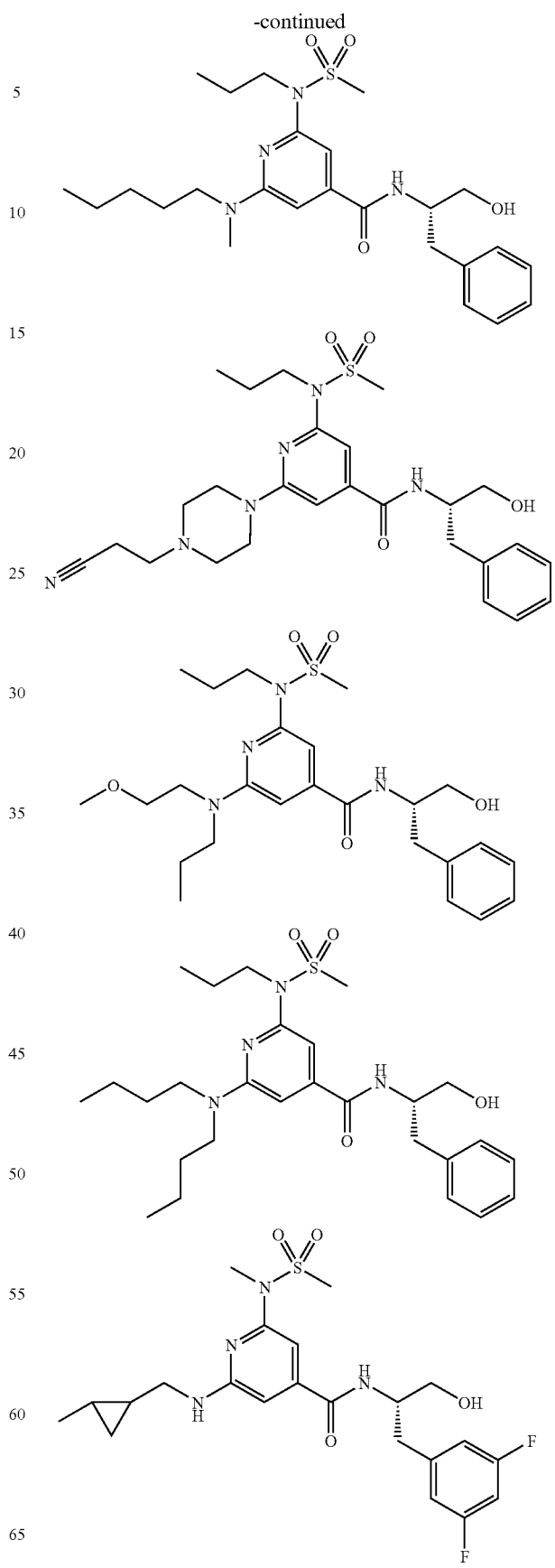

-continued
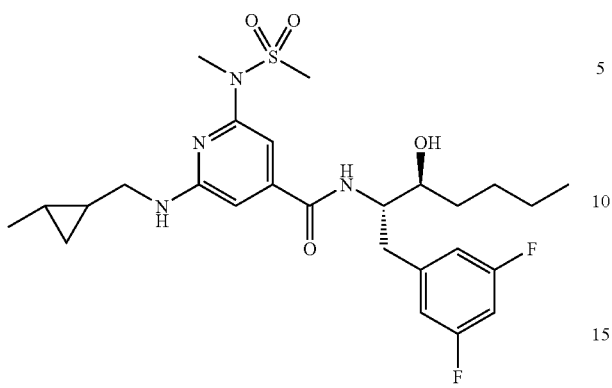
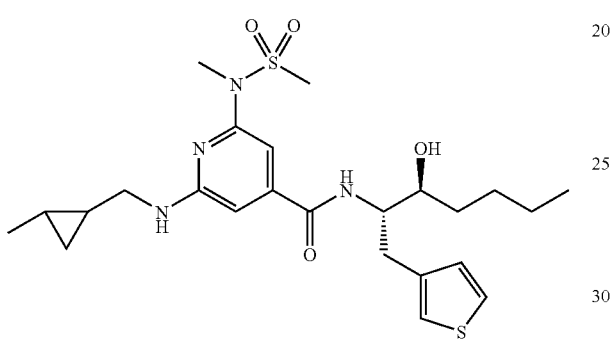
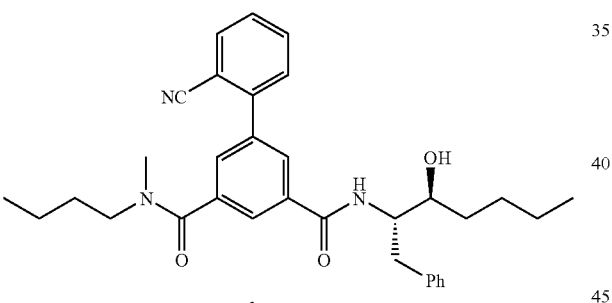
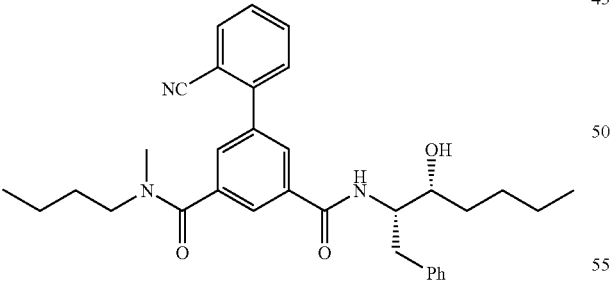
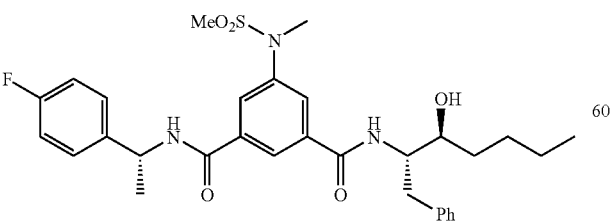
-continued
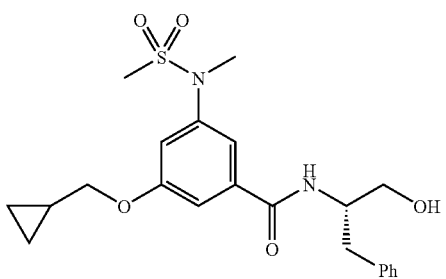
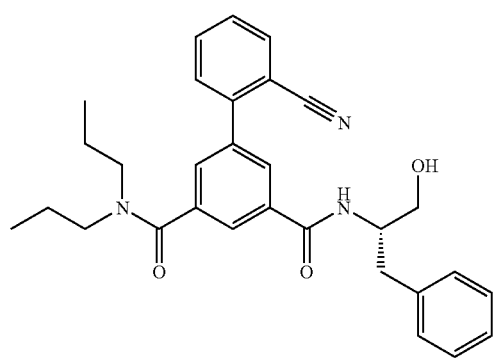
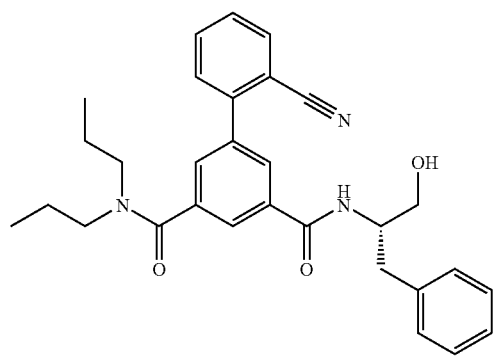
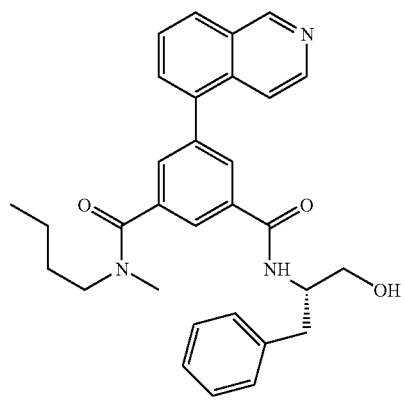

145
-continued
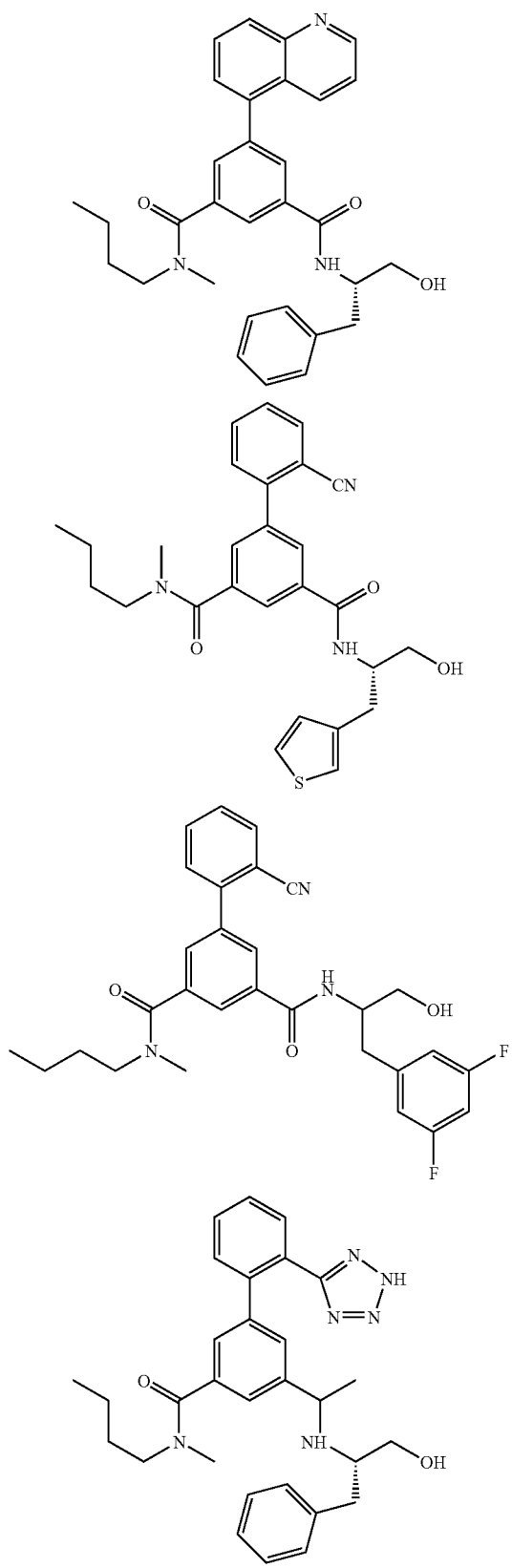
146
-continued
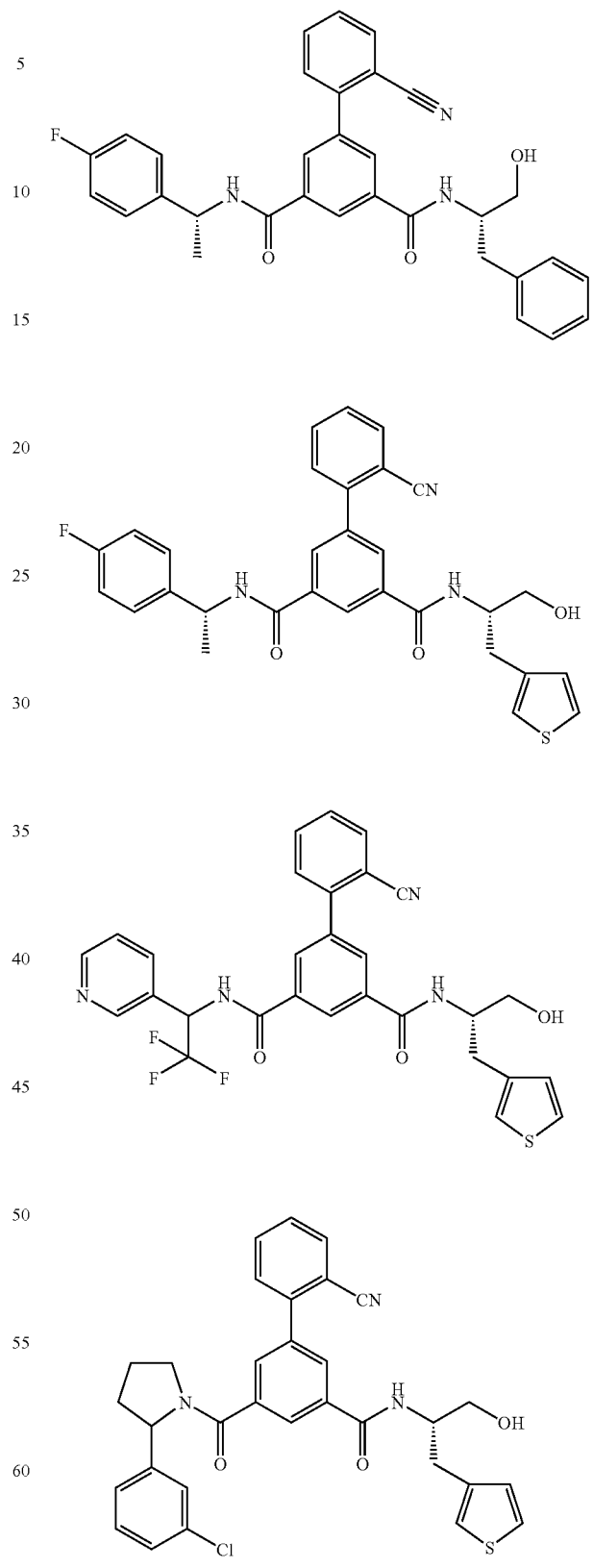

-continued
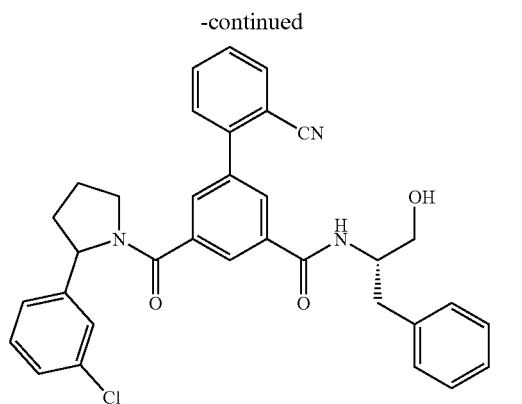
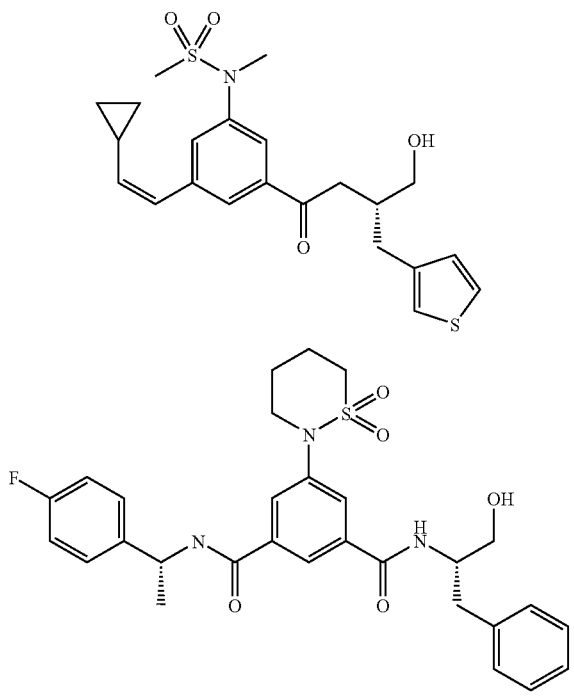
-continued
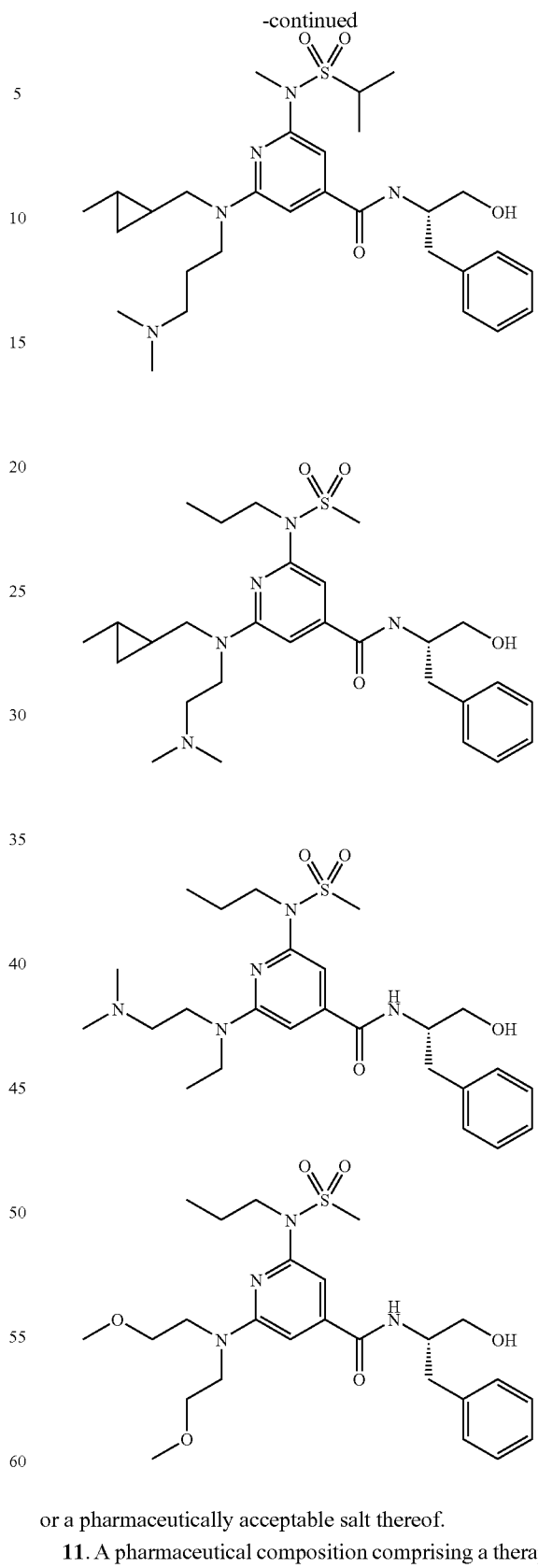
or a pharmaceutically acceptable salt thereof.
11. A pharmaceutical composition comprising a therapeutically effective amount of a compound of claim 1, or a pharmaceutically acceptable salt thereof, and a pharmaceutically acceptable carrier.

12. A compound of formula (I):

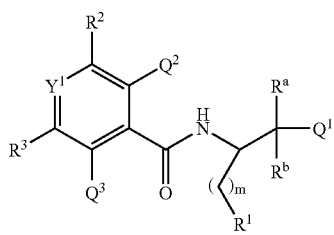

wherein
$y^1$ is CH or N;
$Q^1$ is $NH_2$;
$Q^2$ and $Q^3$ independently selected from the group consisting of
(1) hydrogen, and
(2) halogen;
$R^a$ is selected from the group consisting of
(1) hydrogen,
(2) —$C_{1-10}$ alkyl, wherein said alkyl is unsubstituted or substituted with one or more fluoro, and
(3) —$C_{3-8}$ cycloalkyl;
$R^b$ is selected from the group consisting of
(1) hydrogen, and
(2) —$C_{1-10}$ alkyl,
(3) —$C_{1-3}$ alkyl-aryl, wherein said aryl is selected from the group consisting of phenyl and naphthyl,
(4) —$C_{3-8}$ cycloalkyl,
wherein said cycloalkyl, alkyl and aryl are is unsubstituted or substituted with one or more
(a) halo,
(b) —OH,
(c) —CN,
(d) —O—$C_{1-10}$ alkyl,
(5) —$(CH_2)_n$—$NR^cR^d$ wherein $R^c$ and $R^d$ are selected from the group consisting of hydrogen and $C_{1-0}$ alkyl, and n is 2, 3 or 4, and
(6) —$CH_2)_{n'}$—O—$R^e$, wherein $R^e$ is selected from the group consisting of
(a) $C_{1-10}$ alkyl,
(b) —$C_{0-3}$ alkyl-aryl, wherein said aryl is selected from the group consisting of phenyl and naphthyl,
wherein said alkyl and aryl are unsubstituted or substituted
with one or more
(i) halo,
(ii) —OH,
(iii) —CN,
(iv) —OC—$C_{1-10}$ alkyl,
and n' is 1, 2, 3 or 4;
m is 1 or 2;
$R^1$ is (1) aryl selected from the group consisting of phenyl and napthyl, or
(2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
(3) —$C_{1-10}$ alkyl, and
(4) —$C_{3-8}$ cycloalkyl,
wherein said aryl, heteroaryl, alkyl and cycloalkyl is unsubstituted or substituted with one or more (a) halo,
(b) —OH,
(c) —CN,
(d) —O—$C_{1-10}$ alkyl,
(e) —$C_{1-10}$ alkyl,
(f) —$C_{3-8}$ cycloalkyl,
(g) aryl selected from the group consisting of phenyl and napthyl, or
(h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;
$R_2$ is selected from the group consisting of:
(1) $(R^4$—$SO_2)N(R^7)$—, wherein $R^4$ is
(a) —$C_{1-10}$ alkyl,
(b) —$C_{3-8}$ cycloalkyl,
wherein said alkyl and cycloalkyl is unsubstituted or substituted with one or more
(i) halo,
(ii) —OH,
(iii) —CN,
(iv) —O—$C_{1-10}$ alkyl,
(v) —$C_{1-10}$ alkyl,
(vi) $C_{3-8}$ cycloalkyl,
(vii) aryl selected from the group consisting of phenyl and napthyl, or
(viii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl;
and said aryl and heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) —$C_{1-10}$ alkyl,
(c) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl, or
(vi) —$C_{1-10}$ alkyl,
(d) —$(CH_2)_x$—$NR^fR^g$ wherein $R^f$ and $R^g$ are selected from the group consisting of hydrogen and $C_{1-10}$ alkyl, and x is 0, 1, 2, 3 or 4, or $R^f$ and $R^g$, together with the nitrogen atom to which they are attached form the group

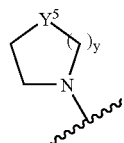

wherein y is 1 or 2, $y^5$ is —$CHR^{21}$, —O— or $NR^{21}$, wherein $R^{12}$ is selected from the group consisting of
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl;

$R^7$ is selected from the group consisting of
(a) hydrogen, and
(b) —$C_{1-10}$ alkyl,
(c) aryl selected from the group consisting of phenyl and napthyl, or
(d) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl
wherein said alkyl, aryl and heteroaryl is unsubstituted or substituted with one or more
(i) halo,
(ii) —OH,
(iii) —CN,
(iv) —O—$C_{1-10}$ alkyl,
(v) $C_{3-8}$ cycloalkyl,
(vi) aryl selected from the group consisting of phenyl and napthyl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said cycloalkyl, aryl or heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) aryl selected from the group consisting of phenyl and napthyl;
(e) —$(CH_2)_{y'}$—$NR^hR^i$ wherein $R^h$ and $R^i$ are selected from the group consisting of hydrogen and $C_{1-10}$ alkyl, and y' is 1, 2, 3 or 4, or or $R^h$ and $R^i$, together with the nitrogen atom to which they are attached from the group

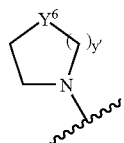

wherein y' is 1 or 2, $y^6$ is —$CHR^{22}$, —O— or $NR^{22}$, wherein $R^{22}$ is selected from the group consisting of,
(i) hydrogen, and
(ii) $C_{1-10}$ alkyl,
wherein said alkyl is unsubstituted or substituted with one or more
(A) halo,
(B) —OH,
(C) —CN,
(D) —O—$C_{1-10}$ alkyl, or
(E) —$C_{3-8}$ cycloalkyl, or $R_4$ and $R_7$ are linked together to form the group (a)

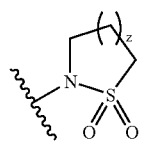

wherein z is 1, 2 or 3; or (2)

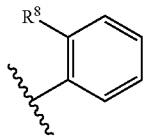

wherein z is 1, 2 or 3

(2)

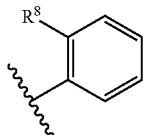

wherein $R_8$ is selected from the group consisting of
(a) —CN,
(b) hydrogen, and
(c) tetrazolyl;

(3)

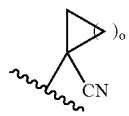

wherein o is 1, 2, 3 or 4; and (4)

[structure: benzofuran-like with Y²]

wherein Y² is —NH=CH— or —CH=NH—;
R³ is selected from the group consisting of (1)

[structure with R⁶ᵃ, R⁶ᵇ, Y³, R⁵, NH-C(=O)]

(2)

[structure with R⁹, R¹⁰—N, C(=O)]

(3)

[structure with R²⁶, R¹², R¹¹, cyclopropyl]; and (4)

[structure with R¹⁴—N, R¹³]

wherein Y³ is CR⁶ᶜ or N;
R⁵ is $C_{1-10}$ alkyl or $C_{12}$ perfluoroalkyl;
R⁶ᵃ, R⁶ᵇ, and R⁶ᶜ are independently selected from the group consisting of:
  (1) hydrogen,
  (2) halo,
  (3) —$C_{1-10}$ alkyl,
  (4) —OH,
  (5) —CN,
  (6) —$C_{3-8}$ cycloalkyl, and
  (7) —O—$C_{1-10}$ alkyl;
R⁹ and R¹⁰ are independently selected from the group consisting of
  (1) hydrogen,
  (2) —$C_{1-10}$ alkyl, and
  (3) —$C_{3-8}$ cycloalkyl,
  wherein said alkyl and cycloalkyl are unsubstituted or substituted with one or more
    (a) halo,
    (b) —OH,
    (c) —CN,
    (d) —O—$C_{1-10}$ alkyl,
    (e) —$C_{3-8}$ cycloalkyl, and
    (f) —NR$^j$R$^k$ wherein R$^j$ and R$^k$ are $C_{1-10}$ alkyl;
or R⁹ and R¹⁰ are joined together with the nitrogen atom to which they are attached to form

[structure: pyrrolidine ring with R²³, ( )_w]

wherein w is 1, 2 or 3, and
R²³ is selected from the group consisting of
  (a) hydrogen,
  (b) —$C_{1-10}$ alkyl,
  (c) —$C_{3-8}$ cycloalkyl,
  (d) —$C_{2-10}$ alkenyl,
  (e) —$C_{2-10}$ alkynyl,
  (f) —(CH$_2$)$_p$-phenyl,
  (g) —(CH$_2$)$_p$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  wherein p is 0 or 1, and
  wherein said alkyl, alkenyl, alkynyl, cycloalkyl, phenyl and heteroaryl is unsubstituted or substituted with one or more
    (i) halo,
    (ii) —$C_{1-10}$ alkyl,
    (iii) —OH,
    (iv) —CN,
    (v) —$C_{3-8}$ cycloalkyl, or
    (vi) —O—$C_{1-10}$ alkyl;
R¹¹ is selected from the group consisting of
  (1) —CH—
  (2) —CH$_2$—,
  (3) —O—, and
  (4) —NR¹⁷—,
provided that when R¹¹ is —CH— the dotted line forms a bond and when R¹¹ is —CH$_2$—, —O— or —NR¹⁷— the dotted line is absent;
R¹⁷ is hydrogen or $C_{1-10}$ alkyl, wherein said $C_{1-10}$ alkyl is unsubstituted or substituted with one or more
  (a) halo,
  (b) —OH,
  (c) —CN,
  (d) —$C_{3-8}$ cycloalkyl,
  (e) —O—$C_{1-10}$ alkyl,
  (f) —(CH$_2$)$_q$-phenyl, wherein q is 1 or 2, and
  (g) —NR¹⁸R¹⁹, and
  wherein R¹⁸ and R¹⁹ are independently selected from the group consisting of
    (i) hydrogen, or
    (ii) —$C_{1-10}$ alkyl;
  or R¹⁸ and R¹⁹, together with the nitrogen atom to which they are attached, form the group

[structure: pyrrolidine ring with Y⁷, ( )_q']

wherein q' is 1 or 2, $Y^7$ is —$CHR^{24}$—, —O— or $NR^{24}$, wherein $R^{24}$ is selected from the group consisting of:
(c) hydrogen, and
(d) —$C_{1-10}$ alkyl,
  wherein said alkyl is unsubstituted or substituted with one or more
  (i) halo,
  (ii) —OH,
  (iii) —CN,
  (iv) —O—$C_{1-10}$ alkyl, or
  (v) —$C_{3-8}$ cycloalkyl;
$R^{26}$ is selected from the group consisting of
(1) hydrogen,
(2) —$C_{1-3}$ alkyl;
$R^{12}$ is selected from the group consisting of
(1) hydrogen,
(2) —$C_{1-10}$ alkyl, wherein said alkyl is unsubstituted or substituted with one or more
  (a) halo,
  (b) —OH,
  (c) —CN,
  (d) —$C_{3-8}$ cycloalkyl,
  (e) —O—$C_{1-10}$ alkyl, or
  (f) —$NH_2$,
(3) halo,
(4) —$C_{3-8}$ cycloalkyl,
(5) aryl selected from the group consisting of phenyl and napthyl, and
(6) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl and heteroaryl is unsubstituted or substituted with one or more
  (a) halo,
  (b) —OH,
  (c) —CN,
  (d) —O—$C_{1-10}$ alkyl,
  (e) —$C_{3-8}$ cycloalkyl, or
  (f) —$C_{1-10}$ alkyl;
$R^{13}$ is selected from the group consisting of
(1) hydrogen,
(2) —$C_{1-10}$ alkyl, and
(3) —$C_{3-8}$ cycloalkyl;
  wherein said alkyl and cycloalkyl is unsubstituted or substituted with one or more
  (a) halo,
  (b) —OH,
  (c) —CN,
  (d) —$C_{3-8}$ cycloalkyl,
  (e) —O—$C_{1-10}$ alkyl, and
  (f) —$C_{1-10}$ alkyl;
$R^{14}$ is selected from the group consisting of
(1) —$C_{1-10}$ alkyl, and
(2) —$C_{3-8}$ cycloalkyl;
wherein said alkyl and cycloalkyl is unsubstituted or substituted with one or more
  (a) halo,
  (b) —OH,
  (c) —CN,
  (d) —$C_{3-8}$ cycloalkyl,
  (e) —O—$C_{1-10}$ alkyl, or
  (f) —$C_{1-10}$ alkyl;

(3) —$(CH_2)_v$—$NR^{15}R^{16}$, wherein v is 2, 3 or 4, and
wherein $R^{15}$ and $R^{16}$ are independently selected from the group consisting of
a) hydrogen, or
b) —$C_{1-10}$ alkyl, wherein said $C_{1-10}$ alkyl is unsubstituted or substituted with one or more
  (i) halo,
  (ii) —OH,
  (iii) —CN,
  (iv) —$C_{3-8}$ cycloalkyl, or
  (v) —O—$C_{1-10}$ alkyl;
or $R^{15}$ and $R^{16}$, together with the nitrogen atom to which they are attached, form the group

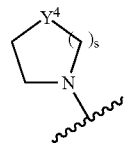

wherein s is 1 or 2, $Y^4$ is —$CHR^{24}$—, —O— or —$NR^{24}$—, wherein $R^{24}$ is selected from the group consisting of
  (i) hydrogen, and
  (ii) $C_{1-10}$ alkyl,
  wherein said alkyl is unsubstituted or substituted with one or more
    (A) halo,
    (B) —OH,
    (C) —CN,
    (D) —O—$C_{1-10}$ alkyl, or
    (E) —$C_{3-8}$ cycloalkyl,
(4) —$(CH_2)_r$-phenyl, wherein r is 1, 2, 3, or 4, and
wherein said phenyl is unsubstituted or substituted with one or more
  (a) halo,
  (b) —OH,
  (c) —CN,
  (d) —O—$C_{1-10}$ alkyl,
  (e) —$C_{3-8}$ cycloalkyl, or
  (f) —$C_{1-10}$ alkyl;
or $R^{13}$ and $R^{14}$, together with the nitrogen atom to which they are attached, form the group

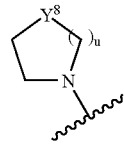

wherein u is 1 or 2, $Y^8$ is —$CHR^{25}$—, —O— or —$NR^{25}$—, wherein $R^{25}$ is selected from the group consisting of
(a) hydrogen,
(b) $C_{1-10}$ alkyl,
(c) —$(CH_2)_t$-phenyl,
(d) —$(CH_2)_t$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein t is 0 or 1, and wherein said alkyl, phenyl and heteroaryl is unsubstituted or substituted with one or more
(i) halo,
(ii) —$C_{1-10}$ alkyl,
(iii) —OH,
(iv) —CN,
(v) —$C_{3-8}$ cycloalkyl, or
(vi) —O—$C_{1-10}$ alkyl;
or a pharmaceutically acceptable salt thereof.

13. The compound of claim 12, or a pharmaceutically acceptable salt thereof, wherein m is 1 and $R^1$ is selected from the group consisting of
(1) phenyl, unsubstituted or substituted in one or two positions with halo; and
(2) thienyl.

14. The compound of claim 12, or a pharmaceutically acceptable salt thereof, wherein $R^2$ is ($R^4$—$SO_2$)N($R^7$)—.

15. The compound of claim 12, or a pharmaceutically acceptable salt thereof, wherein $R^3$ is (1)

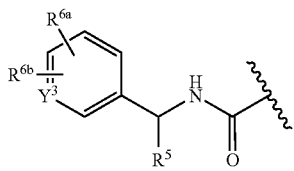

wherein $Y^3$ is $CHR^{6c}$, $R^5$ is methyl, $R^{6a}$ and $R^{6c}$ are hydrogen and $R^{6b}$ is fluoro.

16. The compound of claim 12, or a pharmaceutically acceptable salt thereof, wherein $R^3$ is (2)

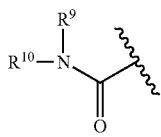

and $R^9$ and $R^{10}$ are each unsubstituted $C_{1-10}$ alkyl, or $R^9$ and $R^{10}$ are joined together with the nitrogen atom to which they are attached to form attached to form

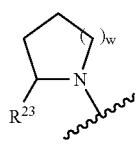

wherein w is 1;
$R^{23}$ is —$(CH_2)_p$-phenyl or —$(CH_2)_p$-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl, wherein the phenyl and heteroaryl are unsubstituted or substituted with one or more chloro, and p is 0.

17. The compound of claim 12, or a pharmaceutically acceptable salt thereof, wherein $R^3$ is (3)

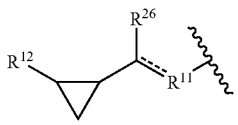

$R^{11}$ is $NR^{17}$ wherein $R^{17}$ is hydrogen or $C_{1-3}$ alkyl, and $R^{12}$ is hydrogen or methyl.

18. The compound of claim 12, or a pharmaceutically acceptable salt thereof, wherein $R^3$ is (4)

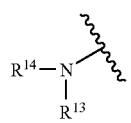

$R^{13}$ is hydrogen and $R^{14}$ is —$(CH_2)_v$—$NR^{15}R^{16}$ wherein v is 2 and $R^{15}$ and $R^{16}$ are each $C_{1-10}$ alkyl, which is unsubstituted or substituted with —OH, —CN or —$OCH_3$.

19. The compound of claim 12, or a pharmaceutically acceptable salt thereof, wherein $R^3$ is (4)

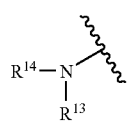

wherein $R^{13}$ and $R^{14}$, together with the nitrogen atom to which they are attached, form the group

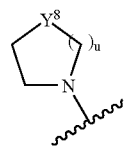

wherein u is 1 or 2, $Y^8$ is —$CHR^{25}$—, —O— or —$NR^{25}$—.

20. A compound of claim 12, which is selected from the group consisting of

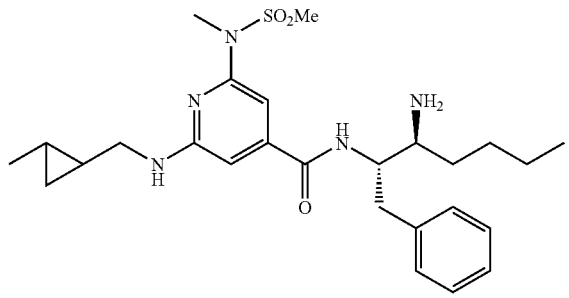

159
-continued
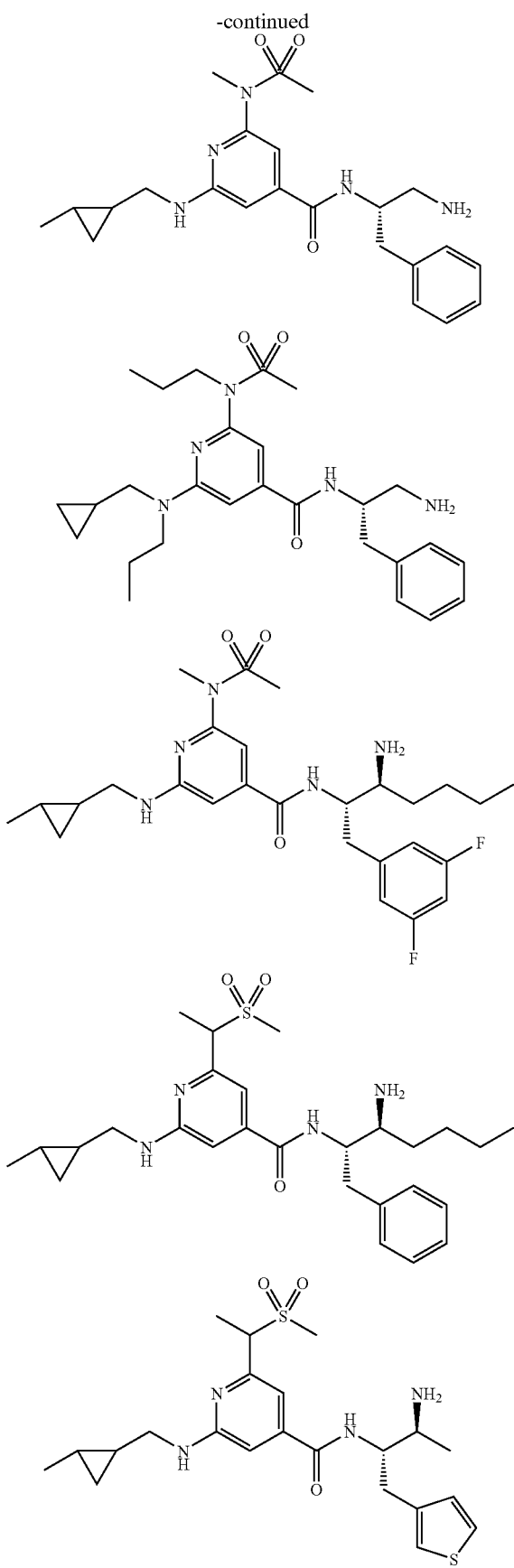
160
-continued
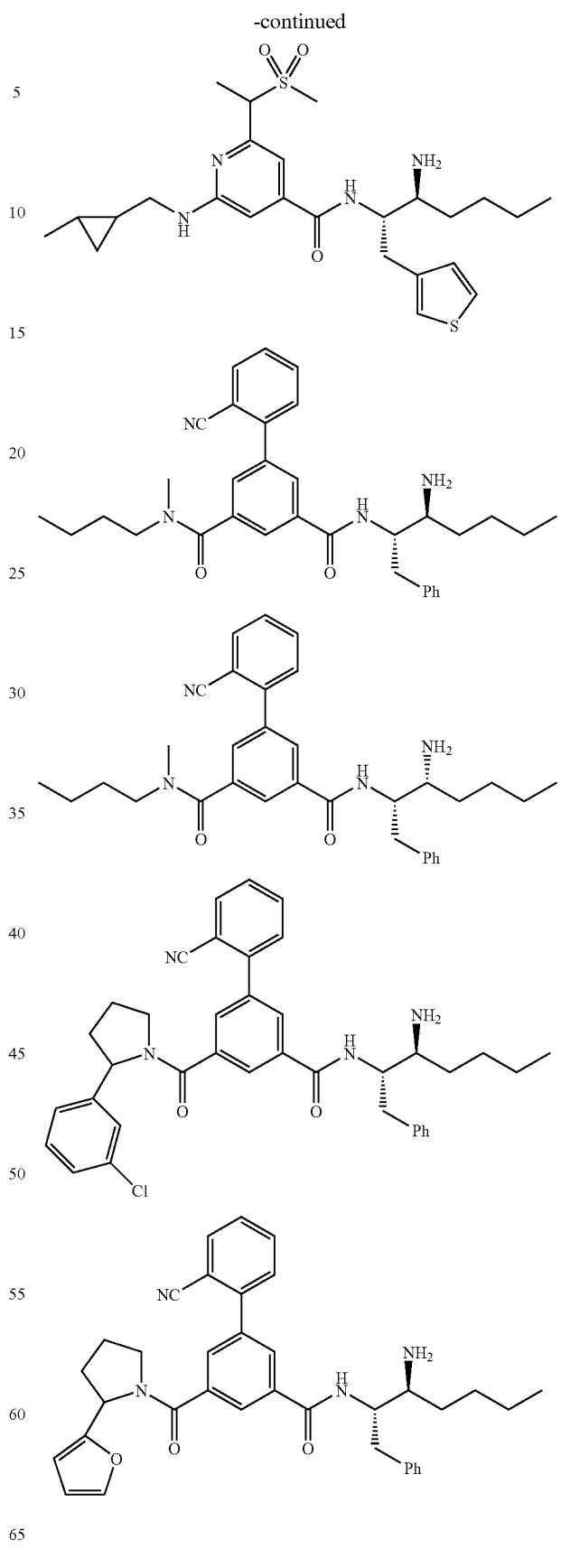

161 -continued
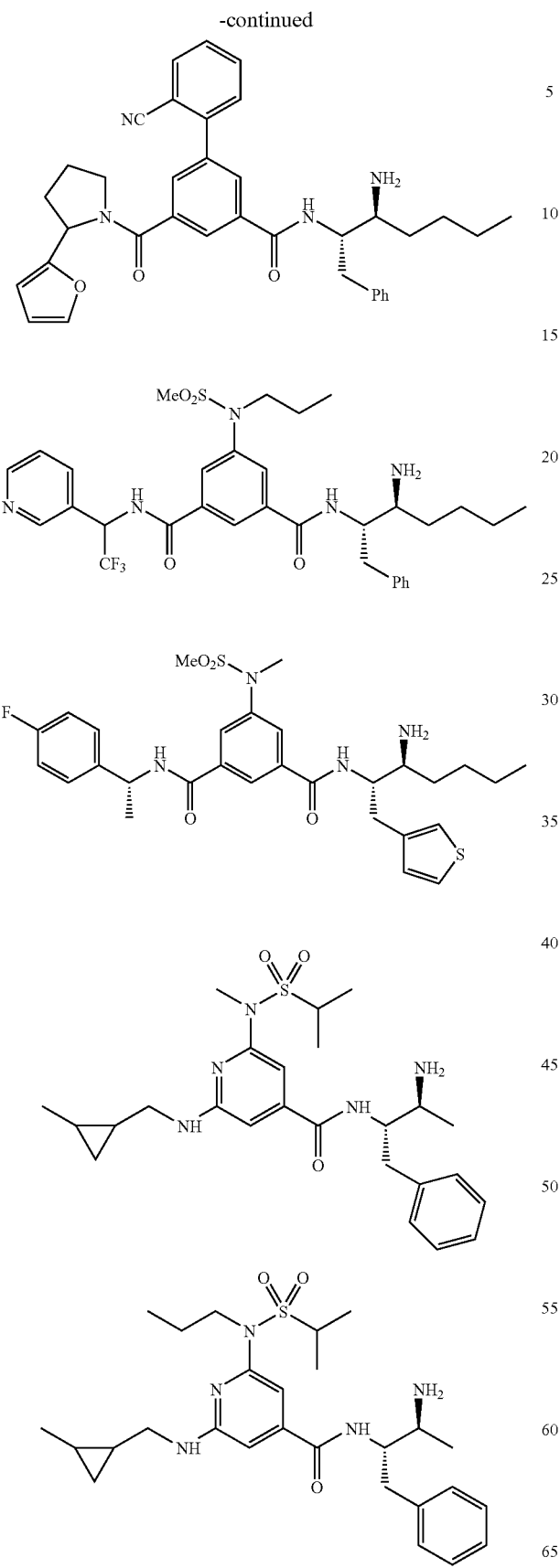
162 -continued
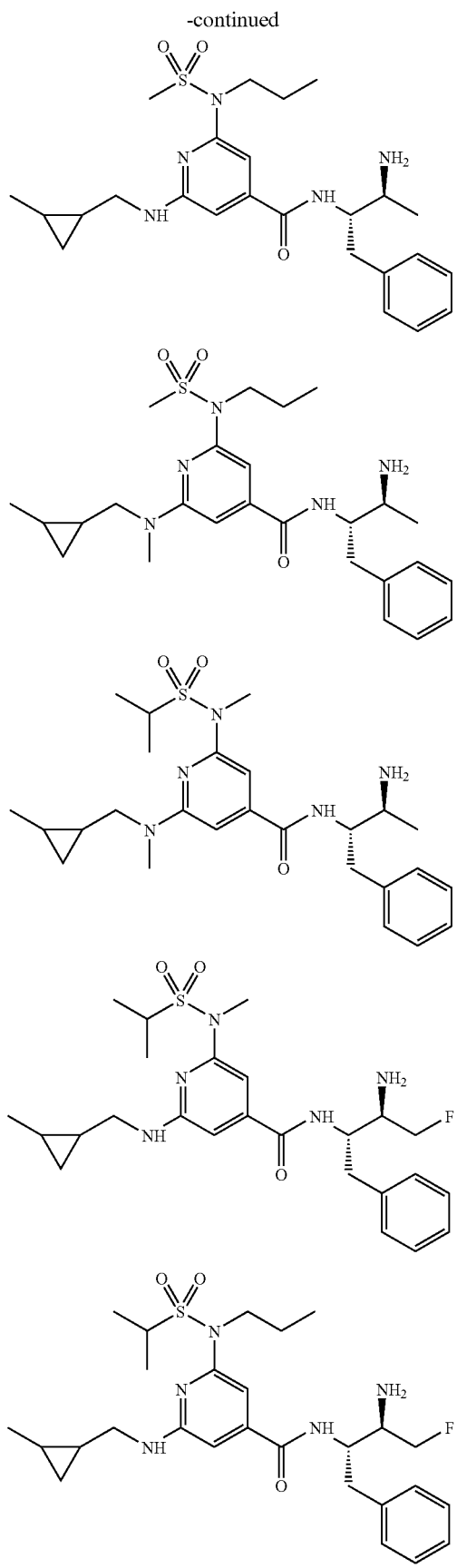

163
-continued
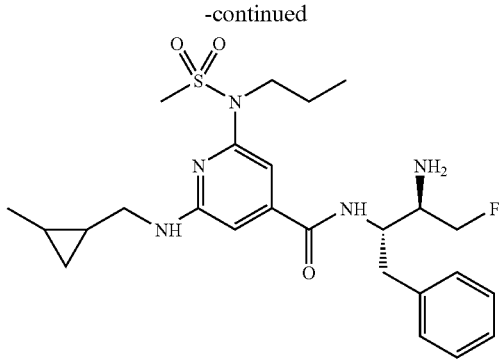
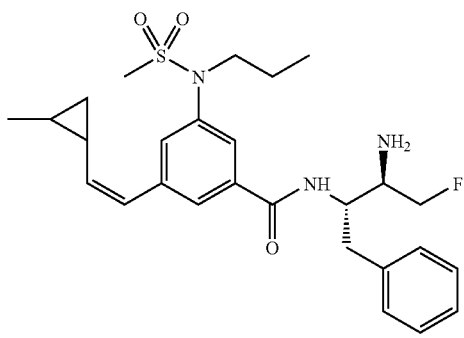
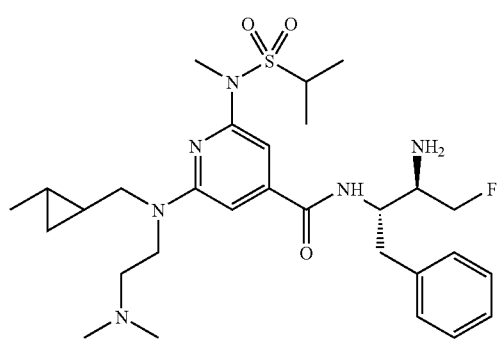
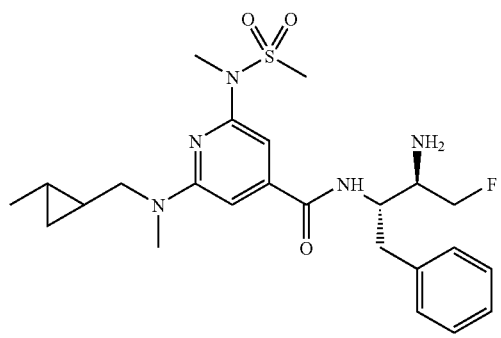
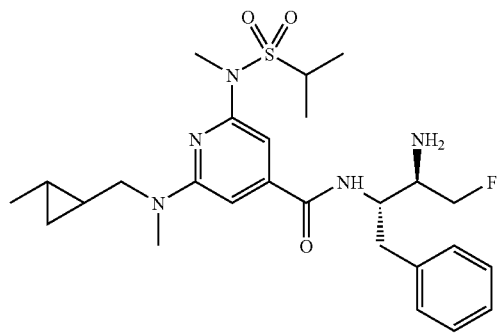
164
-continued
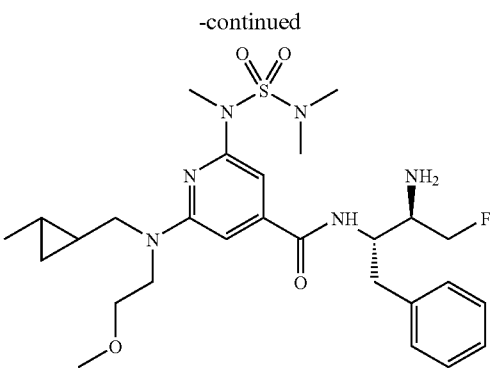
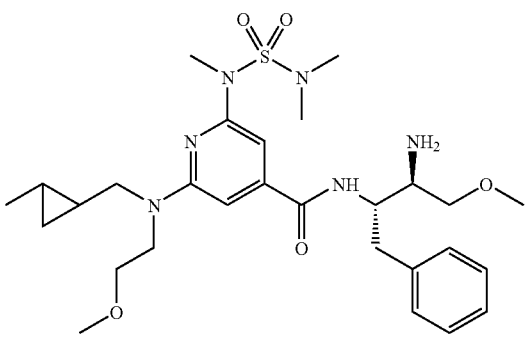
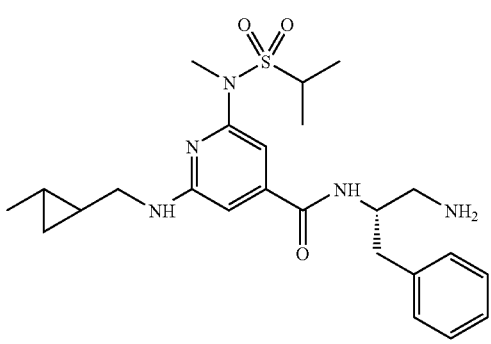
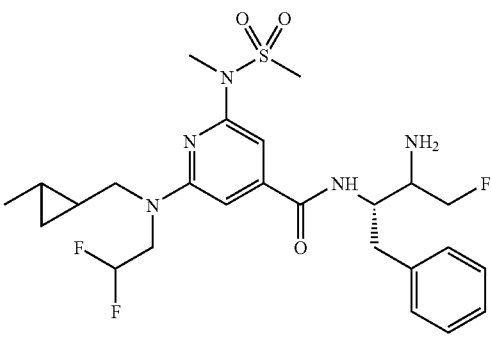
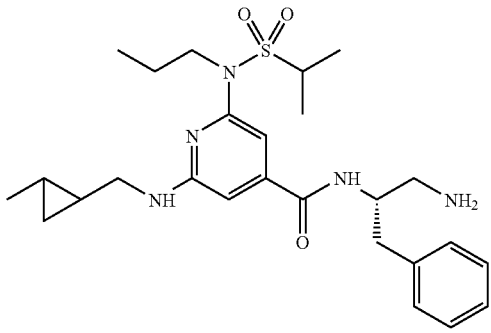

165 -continued
166 -continued
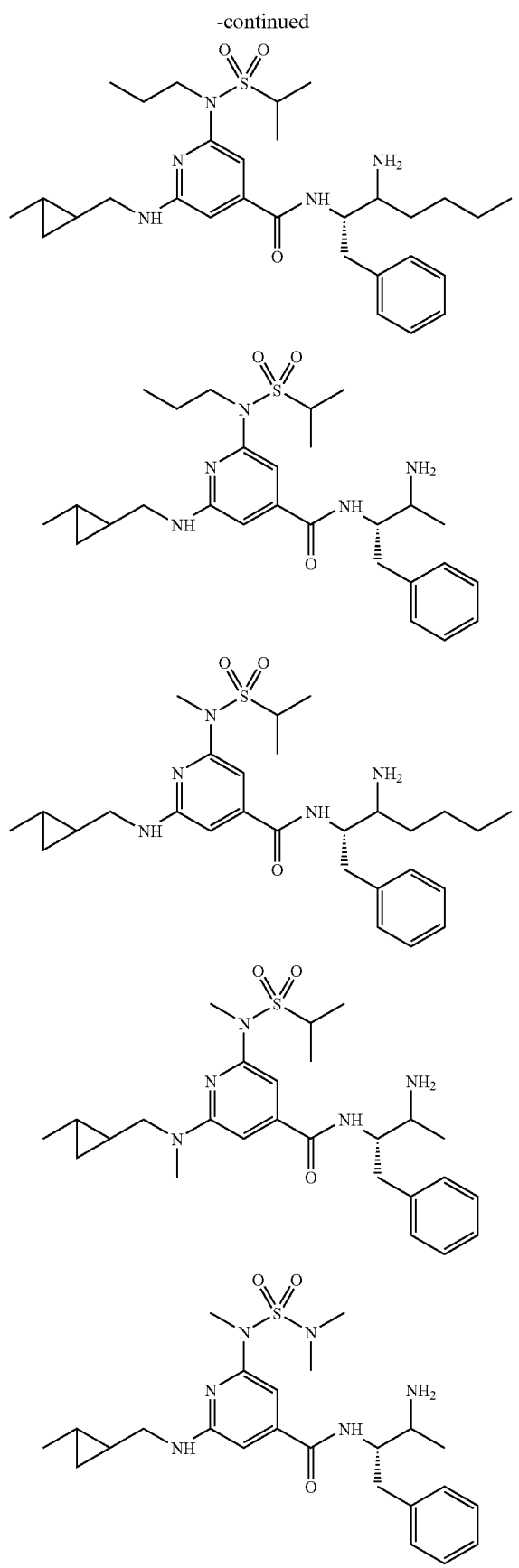
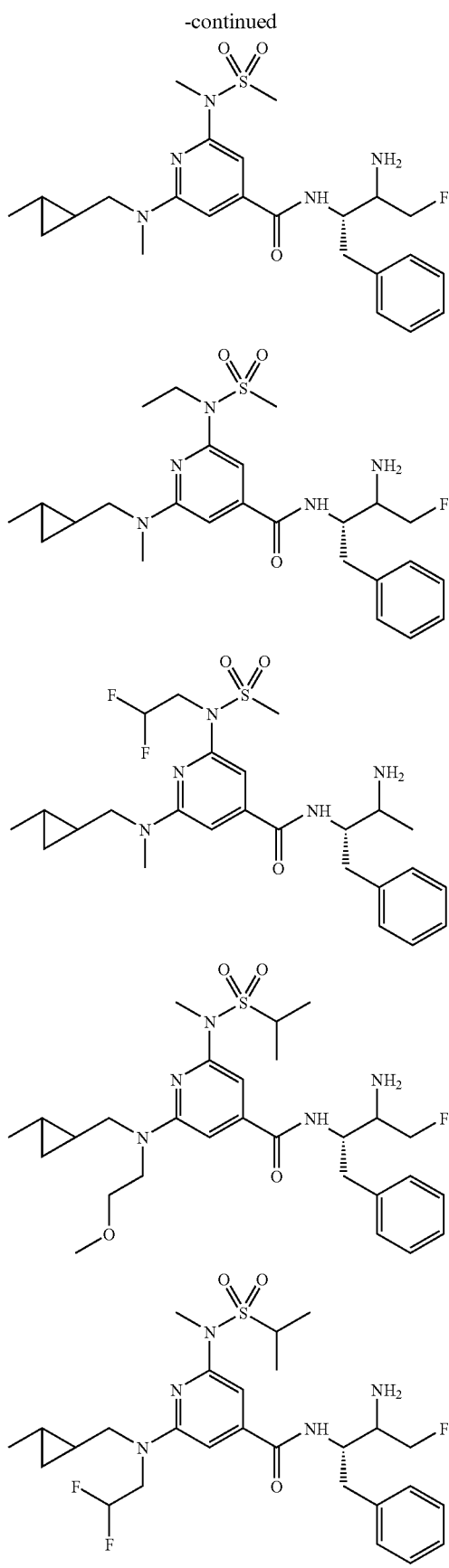

167
-continued
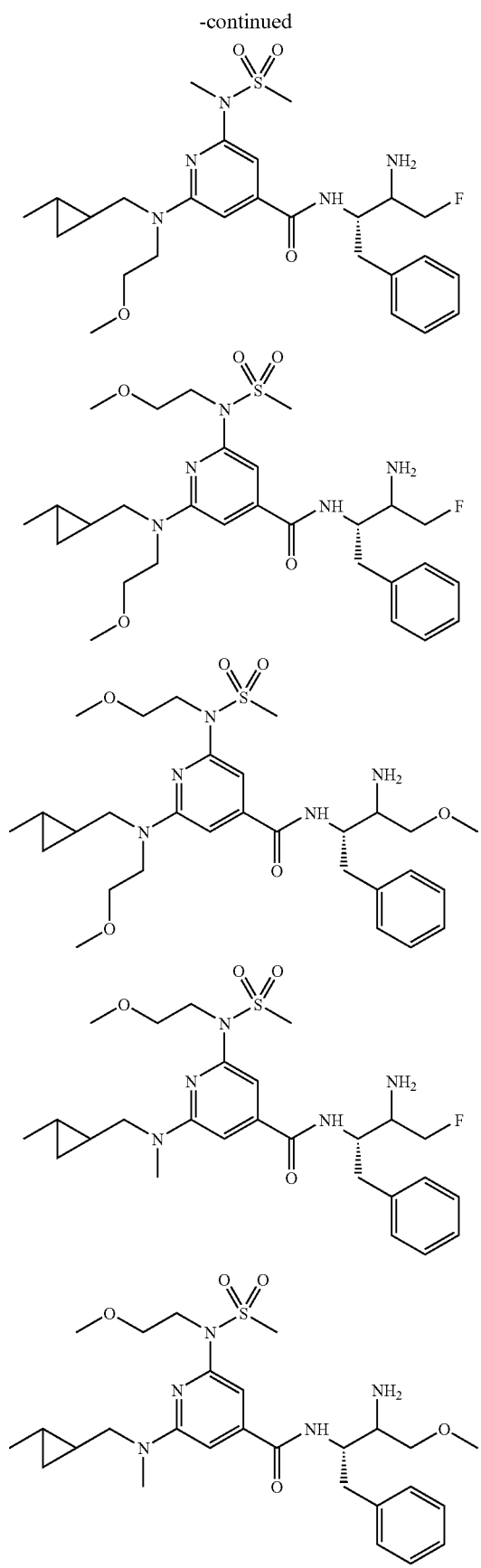
168
-continued
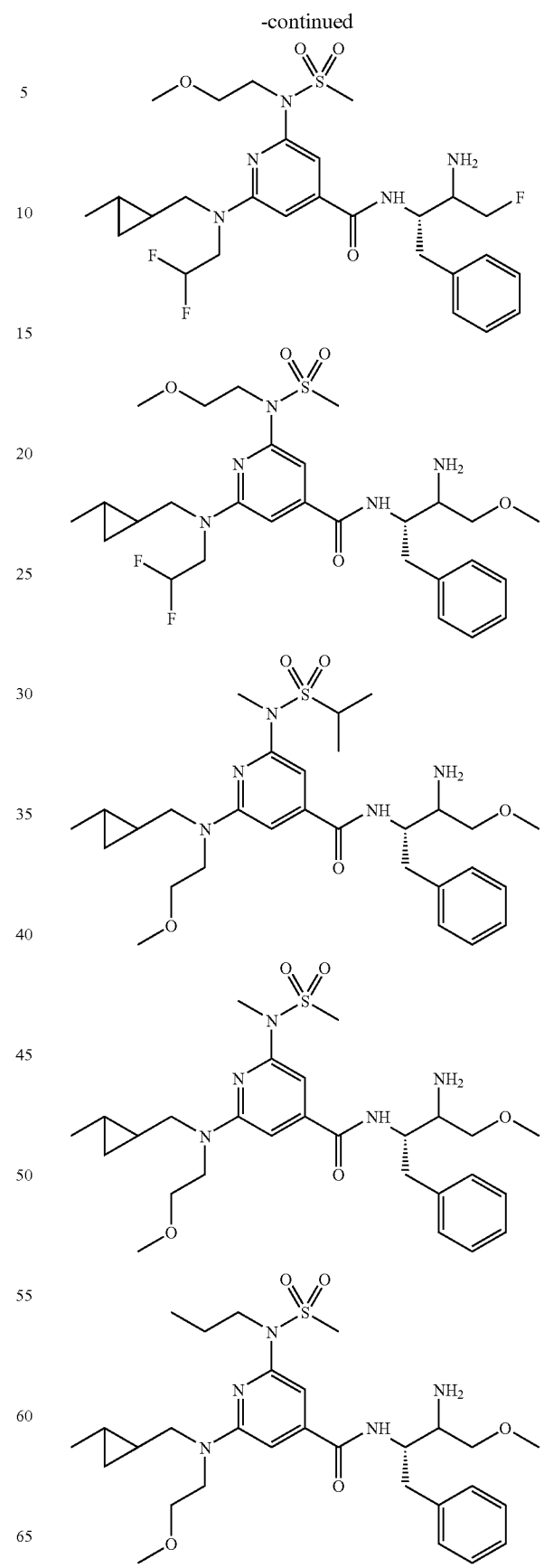

-continued
| 169 | 170 |
|---|---|
| 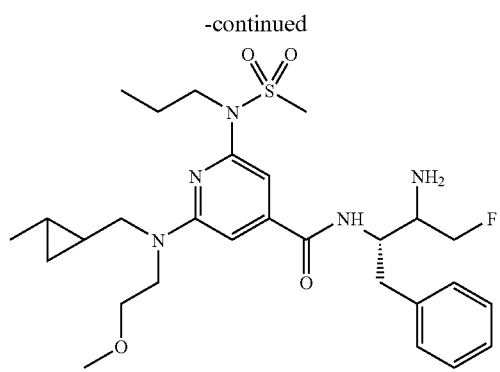 | 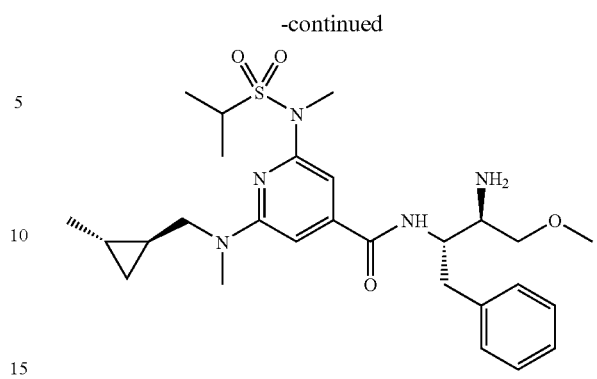 |
| 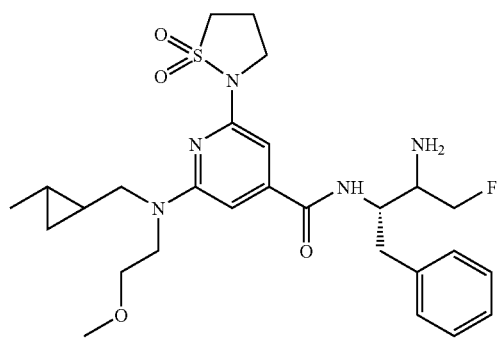 | 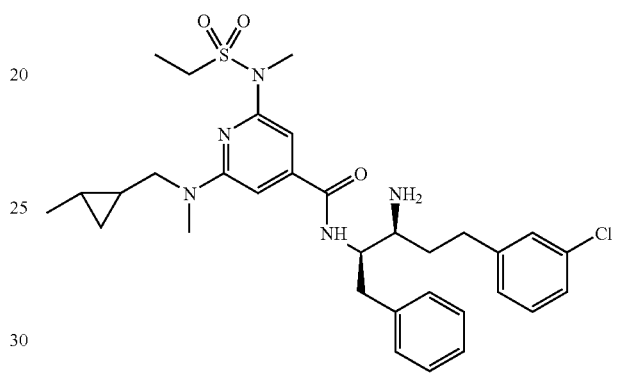 |
| 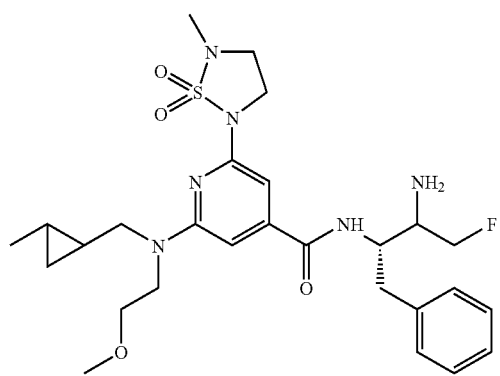 | 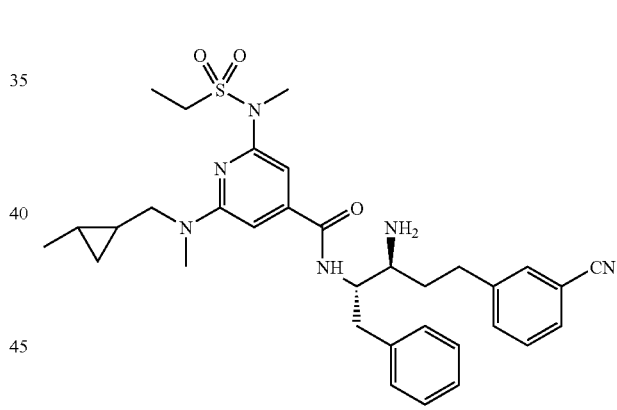 |
| 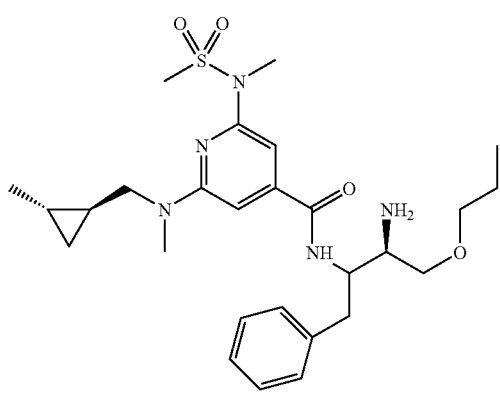 | 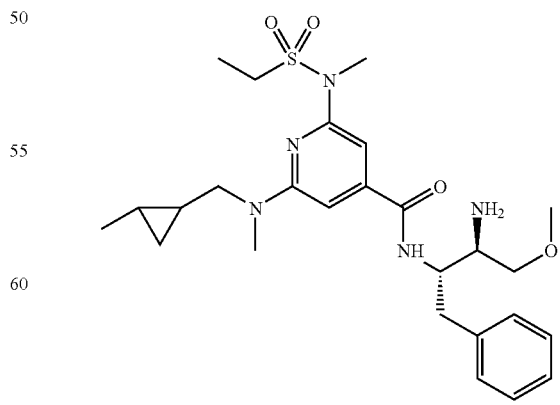 |

171 -continued
172 -continued
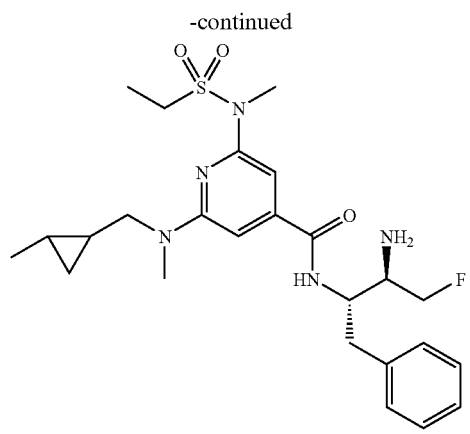
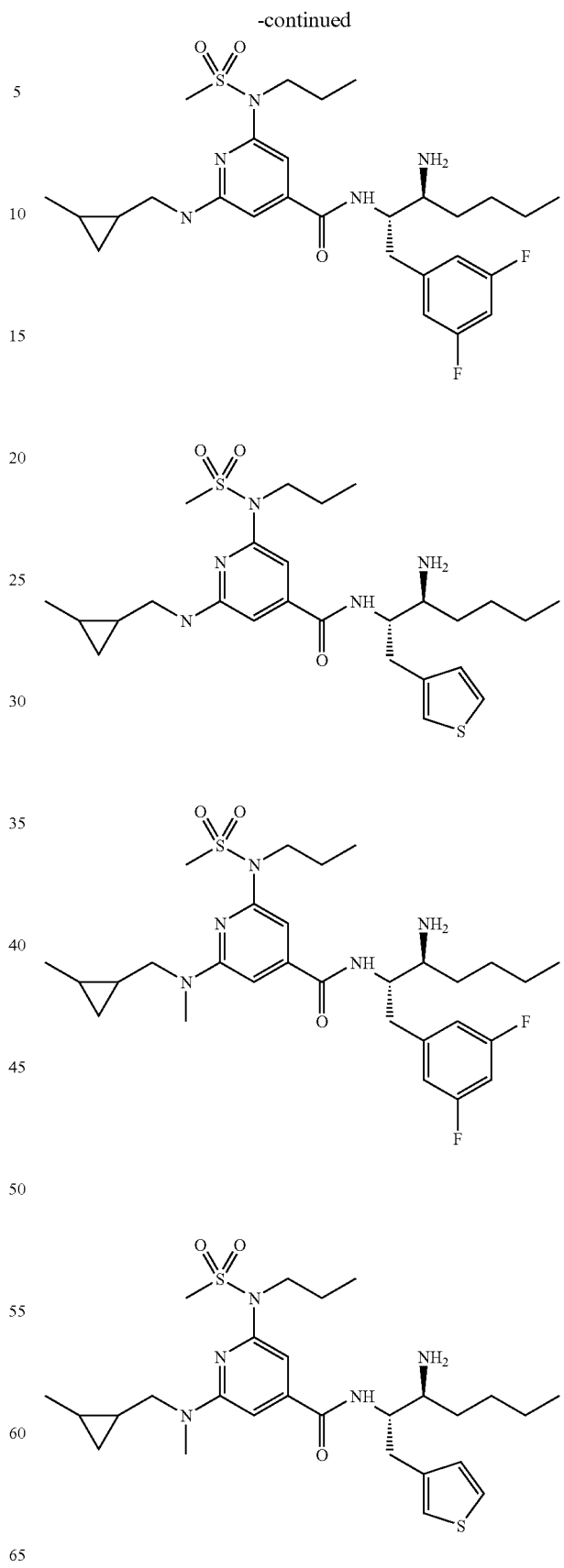

173
-continued
174
-continued
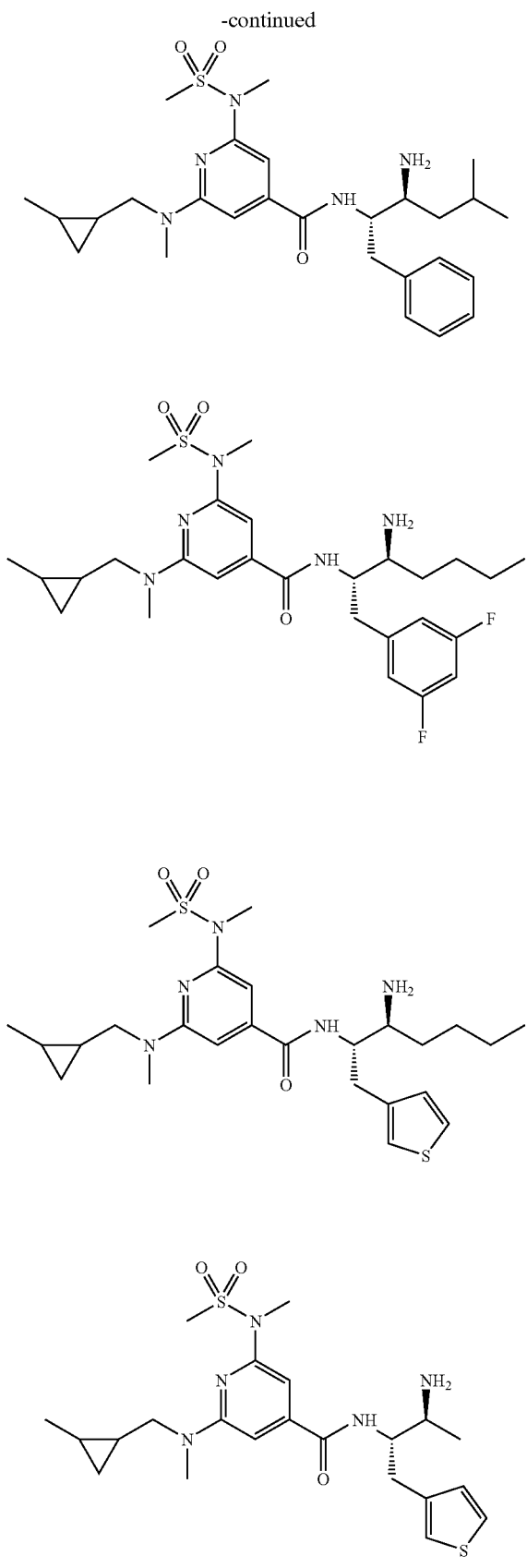
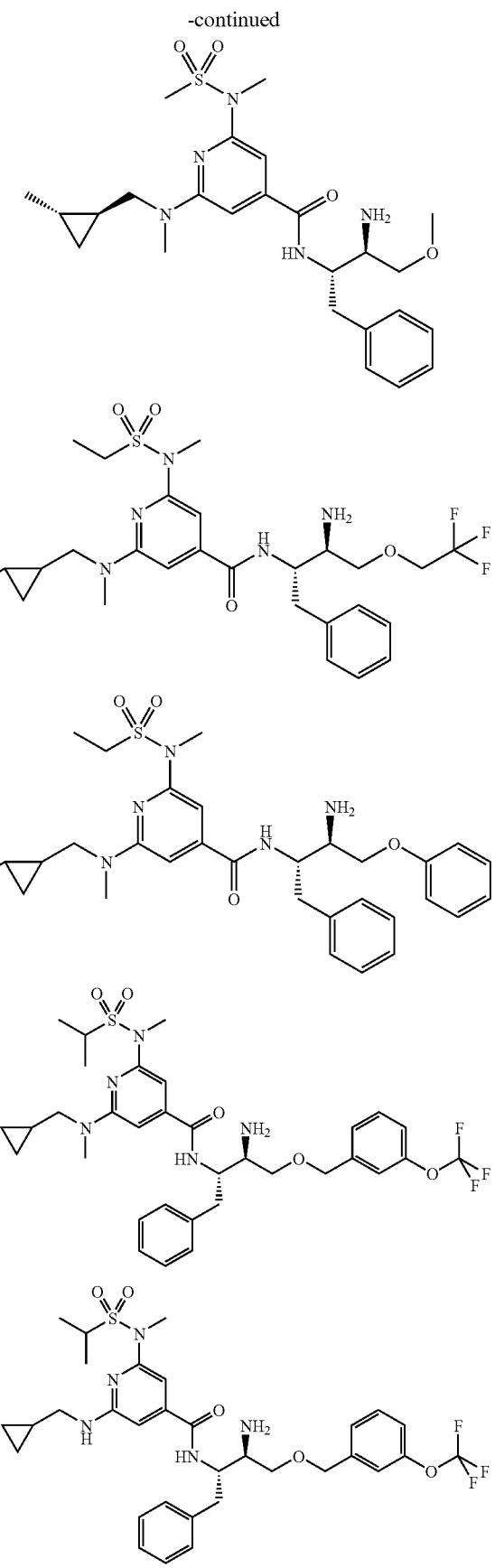

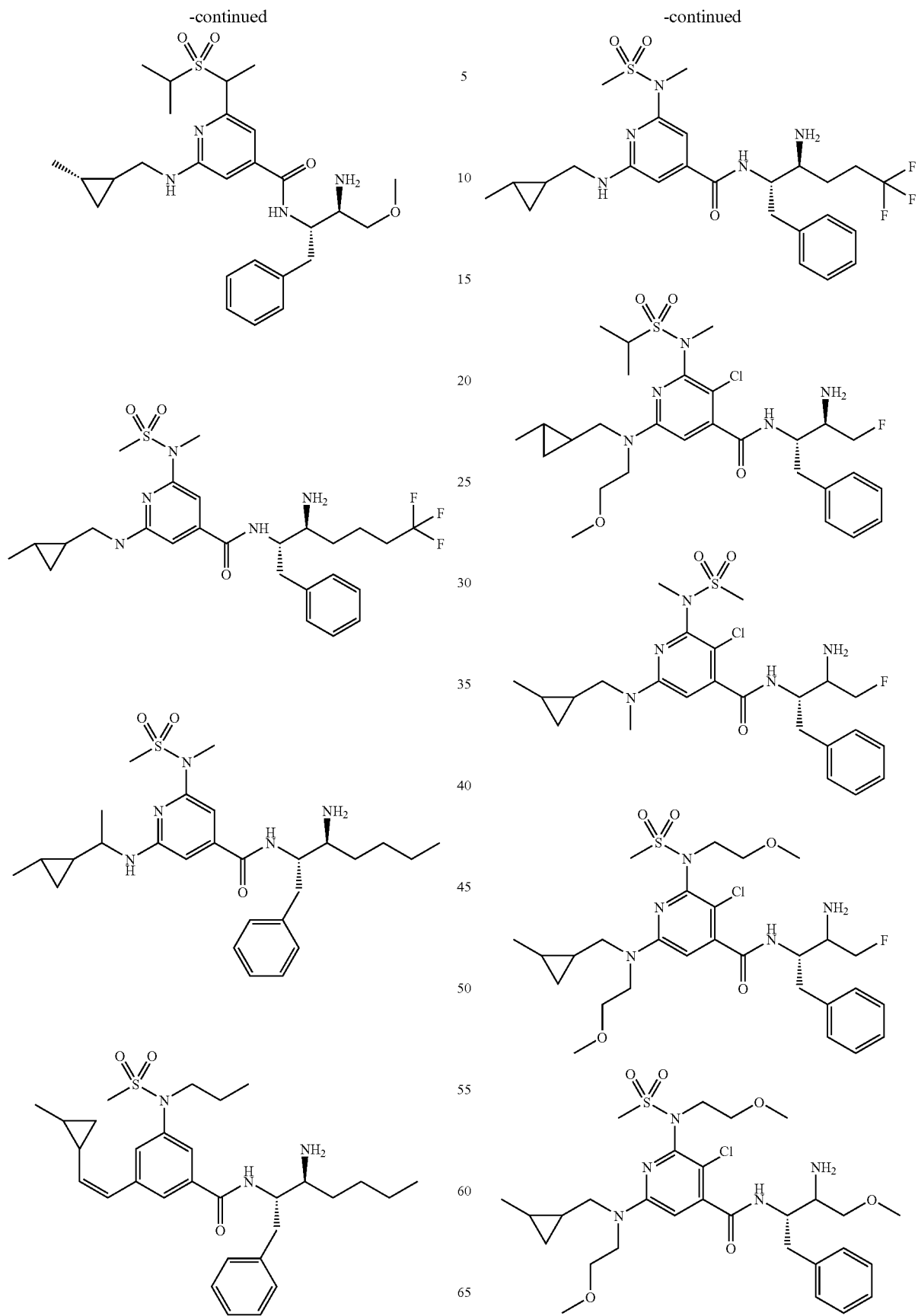

-continued
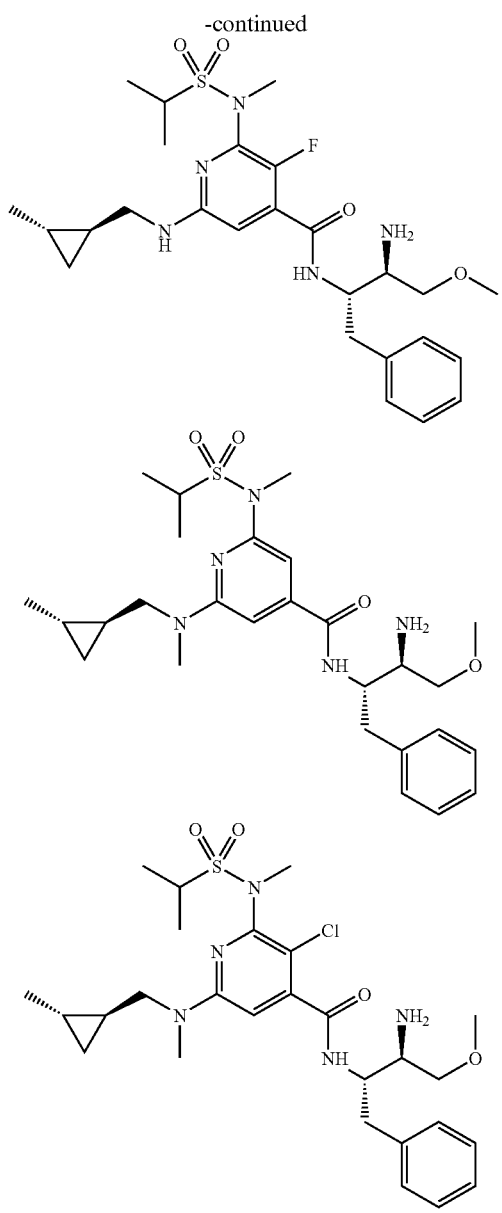
-continued
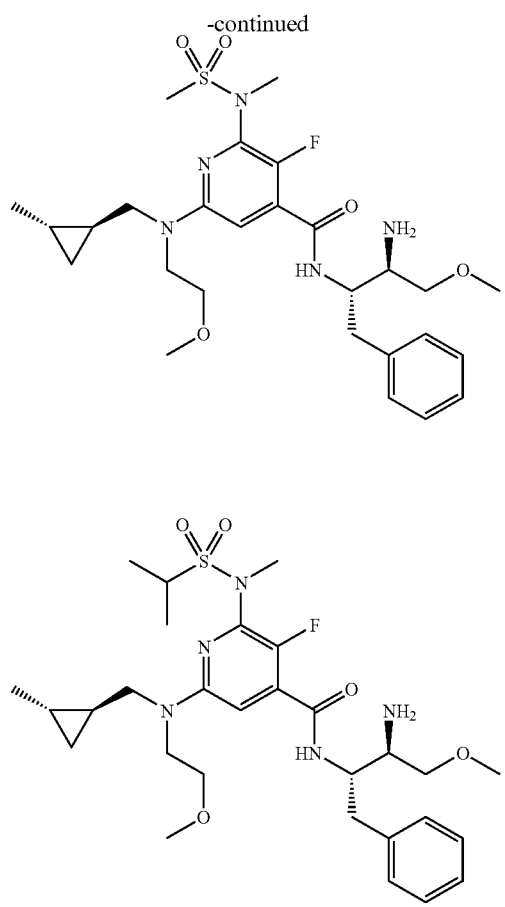
or a pharmaceutically acceptable salt thereof.
21. A pharmaceutical composition comprising a therapeutically effective amount of a compound of claim 12, or a pharmaceutically acceptable salt thereof and a pharmaceutically acceptable carrier.
* * * * *